(12) United States Patent
Wagner

(10) Patent No.: US 10,449,023 B2
(45) Date of Patent: Oct. 22, 2019

(54) ORAL CLEANSING DEVICE WITH ENERGY CONSERVATION

(71) Applicant: WATER PIK, INC., Fort Collins, CO (US)

(72) Inventor: Robert D. Wagner, Firestone, CO (US)

(73) Assignee: WATER PIK, INC., Fort Collins, CO (US)

(*) Notice: Subject to any disclaimer, the term of this patent is extended or adjusted under 35 U.S.C. 154(b) by 418 days.

(21) Appl. No.: 15/206,013

(22) Filed: Jul. 8, 2016

(65) Prior Publication Data

US 2017/0007384 A1 Jan. 12, 2017

Related U.S. Application Data

(60) Provisional application No. 62/190,094, filed on Jul. 8, 2015.

(51) Int. Cl.
| | |
|---|---|
| *A61C 17/34* | (2006.01) |
| *A46B 13/02* | (2006.01) |
| *A46B 13/04* | (2006.01) |
| *A61C 17/36* | (2006.01) |
| *A61C 17/22* | (2006.01) |

(Continued)

(52) U.S. Cl.
CPC .......... *A61C 17/3409* (2013.01); *A46B 13/02* (2013.01); *A46B 13/04* (2013.01); *A61C 17/0202* (2013.01); *A61C 17/032* (2019.05); *A61C 17/225* (2013.01);
(Continued)

(58) Field of Classification Search
CPC ..... A61C 17/02; A61C 17/0214; A61C 17/22; A61C 17/32; A61C 17/34; A61C 17/3409; A61C 17/3418; A61C 17/3427; A61C 17/3436; A61C 17/3445; A61C 17/3454; A61C 17/3463; A61C 17/3481;
(Continued)

(56) References Cited

U.S. PATENT DOCUMENTS

| | | | |
|---|---|---|---|
| 669,402 A | 3/1901 | Rose | |
| 684,951 A | 10/1901 | Rothkranz | |

(Continued)

FOREIGN PATENT DOCUMENTS

| | | |
|---|---|---|
| CH | 435553 | 10/1967 |
| CH | 609238 | 2/1979 |

(Continued)

OTHER PUBLICATIONS

Sonex International: Brushing with the Ultima—The World's Only Dual-Frequency Ultrasonic Toothbrush, Jul. 28, 1999, published at Sonipic.com.

(Continued)

*Primary Examiner* — Mark Spisich
(74) *Attorney, Agent, or Firm* — Dorsey & Whitney LLP

(57) ABSTRACT

A brushing device including a motor having an eccentric drive shaft, an output shaft operably connected to the motor, and a power train assembly coupled between the eccentric drive shaft and the output shaft. The power train converts rotation of the eccentric drive shaft into an oscillating movement of the output shaft. The power train includes one or more conservation features that absorb energy when the output shaft rotates in a first direction and reapply energy to the output shaft when it rotates in a second direction.

20 Claims, 30 Drawing Sheets

(51) Int. Cl.
  *A61C 17/40* (2006.01)
  *A61C 17/02* (2006.01)
  *A61C 17/032* (2006.01)
(52) U.S. Cl.
  CPC .......... *A61C 17/3418* (2013.01); *A61C 17/36* (2013.01); *A61C 17/40* (2013.01)
(58) Field of Classification Search
  CPC ....... A61C 17/36; A46B 13/02; A46B 13/023; A46B 13/04
  USPC ................ 15/22.1, 22.2, 22.4; 433/80–90; 601/162, 165
  See application file for complete search history.

(56) References Cited

U.S. PATENT DOCUMENTS

| | | |
|---|---|---|
| 914,501 A | 3/1909 | McEachern |
| 933,718 A | 9/1909 | Mahoney |
| 958,371 A | 5/1910 | Danek |
| 1,018,927 A | 2/1912 | Sarrazin |
| 1,033,819 A | 7/1912 | McMann |
| 1,059,426 A | 4/1913 | Barnes |
| D45,199 S | 2/1914 | McDonagh et al. |
| D45,572 S | 4/1914 | Sarrazin |
| 1,128,139 A | 2/1915 | Hoffman |
| D49,472 S | 8/1916 | Dierke |
| 1,251,250 A | 12/1917 | Libby |
| 1,268,544 A | 6/1918 | Cates |
| 1,278,225 A | 9/1918 | Schamberg |
| 1,296,067 A | 3/1919 | Fuller |
| D53,453 S | 7/1919 | Lloyd |
| 1,313,490 A | 8/1919 | Larson |
| 1,337,173 A | 4/1920 | White |
| 1,355,037 A | 10/1920 | Dziuk |
| D57,327 S | 3/1921 | Gibson |
| 1,382,681 A | 6/1921 | Segal |
| 1,424,879 A | 8/1922 | Carlstedt |
| 1,440,785 A | 1/1923 | Levis |
| 1,456,535 A | 5/1923 | Cartwright |
| 1,488,214 A | 3/1924 | Mason |
| 1,494,448 A | 5/1924 | Sookne |
| 1,497,495 A | 6/1924 | Fincke |
| 1,517,320 A | 12/1924 | Stoddart |
| 1,527,853 A | 2/1925 | Ferdon |
| 1,588,785 A | 6/1926 | Van Sant |
| 1,639,880 A | 8/1927 | Butler |
| 1,657,450 A | 1/1928 | Barnes |
| 1,676,703 A | 7/1928 | Nuyts |
| 1,696,835 A | 12/1928 | Burnett |
| 1,703,642 A | 2/1929 | Sticht |
| 1,794,711 A | 3/1931 | Jacobs |
| 1,796,641 A | 3/1931 | Zimmerman et al. |
| 1,800,993 A | 4/1931 | Funk |
| 1,832,519 A | 11/1931 | Wheat et al. |
| 1,869,991 A * | 8/1932 | White ................ A61C 17/3472 15/22.4 |
| 1,880,617 A | 10/1932 | White |
| 1,916,641 A | 7/1933 | Seeliger |
| 1,927,365 A | 9/1933 | Frolio |
| 1,943,225 A | 1/1934 | McIntyre |
| 1,992,770 A | 2/1935 | Rathbun |
| 2,016,597 A | 10/1935 | Drake |
| 2,016,644 A | 10/1935 | Luball |
| 2,042,239 A | 5/1936 | Planding |
| 2,044,863 A | 6/1936 | Sticht |
| D101,080 S | 9/1936 | Cosad |
| 2,114,947 A | 4/1938 | Warsaw |
| D113,743 S | 3/1939 | Kahn |
| D113,744 S | 3/1939 | Kahn |
| 2,158,738 A | 5/1939 | Baker et al. |
| 2,168,964 A | 8/1939 | Strasser |
| 2,206,726 A | 7/1940 | Lasater |
| 2,209,173 A | 7/1940 | Russell |
| 2,218,072 A | 10/1940 | Runnels |
| 2,226,663 A | 12/1940 | Hill et al. |
| 2,244,098 A | 6/1941 | Busick |
| 2,246,523 A | 6/1941 | Kulik |
| 2,273,717 A | 2/1942 | Millard et al. |
| 2,278,365 A | 3/1942 | Daniels |
| 2,279,355 A | 4/1942 | Wilensky |
| 2,282,700 A | 5/1942 | Bobbroff |
| 2,312,828 A | 3/1943 | Adamsson |
| D136,156 S | 8/1943 | Fuller |
| D139,532 S | 11/1944 | Trecek |
| D141,350 S | 5/1945 | Alexander et al. |
| D144,163 S | 3/1946 | Dolnick |
| 2,401,186 A | 5/1946 | Price |
| 2,405,029 A | 7/1946 | Gallanty et al. |
| D146,271 S | 1/1947 | Stavely |
| 2,414,775 A | 1/1947 | Stavely |
| 2,429,740 A | 10/1947 | Aufsesser |
| 2,450,635 A | 10/1948 | Dembenski |
| D154,598 S | 7/1949 | Gass |
| D155,668 S | 10/1949 | Zandberg et al. |
| D157,669 S | 3/1950 | Graves, Jr. |
| D160,101 S | 9/1950 | MacDonald |
| 2,533,345 A | 12/1950 | Bennett |
| 2,543,999 A | 3/1951 | Voss |
| D163,707 S | 6/1951 | Pifer |
| 2,558,332 A | 6/1951 | Artale |
| 2,567,080 A | 9/1951 | Pifer |
| 2,577,597 A | 12/1951 | Wright et al. |
| 2,583,750 A | 1/1952 | Runnels |
| 2,598,275 A | 5/1952 | Lakin |
| 2,618,003 A | 11/1952 | Robey |
| D169,131 S | 3/1953 | Fay |
| 2,651,068 A | 9/1953 | Seko |
| D170,680 S | 10/1953 | Del Mas |
| D172,693 S | 7/1954 | Wibbelsman et al. |
| D173,616 S | 12/1954 | Hernandez |
| 2,705,335 A | 4/1955 | Glassman et al. |
| 2,709,227 A | 5/1955 | Foley et al. |
| 2,722,703 A | 11/1955 | Green |
| 2,728,928 A | 1/1956 | Beeren |
| 2,734,139 A | 2/1956 | Murphy |
| 2,806,235 A | 9/1957 | Carstairs et al. |
| 2,819,482 A | 1/1958 | Applegate |
| 2,868,215 A | 1/1959 | Mechem |
| 2,875,458 A | 3/1959 | Tsuda |
| 2,917,758 A | 12/1959 | Held et al. |
| 2,931,371 A | 4/1960 | Petitta |
| 2,946,072 A | 7/1960 | Filler et al. |
| 2,962,033 A | 11/1960 | Lew |
| 2,977,614 A | 4/1961 | Demanuele |
| 2,977,682 A | 4/1961 | Flatray |
| 3,103,027 A | 9/1963 | Birch |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,160,902 A | 12/1964 | Aymar |
| 3,168,834 A | 2/1965 | Smithson |
| 3,181,189 A | 5/1965 | Leyden |
| 3,183,538 A | 5/1965 | Hubner |
| 3,195,537 A | 7/1965 | Blasi |
| D202,873 S | 11/1965 | Husted |
| 3,220,039 A | 11/1965 | Dayton et al. |
| 3,227,380 A * | 1/1966 | Pinkston ............ A61C 17/0214 239/427 |
| 3,229,318 A | 1/1966 | Clemens |
| 3,230,562 A | 1/1966 | Birch |
| D204,127 S | 3/1966 | Syvertson |
| 3,258,805 A | 7/1966 | Rossnan |
| 3,270,416 A | 9/1966 | Massa |
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush |

(56) References Cited

U.S. PATENT DOCUMENTS

| | | |
|---|---|---|
| 3,335,443 A | 8/1967 | Parisi et al. |
| 3,346,748 A | 10/1967 | McNair |
| 3,358,309 A | 12/1967 | Richardson |
| 3,358,314 A | 12/1967 | Matibag |
| 3,359,588 A | 12/1967 | Kobler |
| 3,364,576 A | 1/1968 | Kern, Jr. |
| D210,066 S | 2/1968 | Johnson |
| 3,369,265 A | 2/1968 | Halberstadt et al. |
| 3,371,260 A | 2/1968 | Jackson et al. |
| D210,349 S | 3/1968 | Boldt |
| 3,375,820 A | 4/1968 | Kuris et al. |
| 3,394,277 A | 7/1968 | Satkunas et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| 3,509,874 A | 5/1970 | Stillman |
| 3,535,726 A | 10/1970 | Sawyer |
| 3,536,065 A | 10/1970 | Moret |
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| 3,638,264 A | 2/1972 | Walton |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |
| 3,676,218 A | 7/1972 | Sawyer |
| 3,685,080 A | 8/1972 | Hubner |
| 3,722,020 A | 3/1973 | Hills |
| 3,742,549 A | 7/1973 | Scopp et al. |
| 3,759,274 A | 9/1973 | Warner |
| 3,760,799 A | 9/1973 | Crowson |
| 3,792,504 A | 2/1974 | Smith |
| 3,809,977 A | 5/1974 | Balamuth et al. |
| 3,831,611 A | 8/1974 | Hendricks |
| 3,840,932 A | 10/1974 | Balamuth et al. |
| 3,847,167 A | 11/1974 | Brien |
| 3,851,984 A | 12/1974 | Crippa |
| D234,518 S | 3/1975 | Gerlich |
| 3,882,364 A | 5/1975 | Wright et al. |
| 3,902,510 A | 9/1975 | Roth |
| 3,903,601 A | 9/1975 | Anderson et al. |
| 3,921,297 A * | 11/1975 | Vit ............................ A61C 3/00 285/148.13 |
| 3,939,599 A | 2/1976 | Henry et al. |
| 3,967,617 A | 7/1976 | Krolik |
| 3,973,558 A | 8/1976 | Stouffer et al. |
| 3,977,084 A | 8/1976 | Sloan |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,010,509 A | 3/1977 | Huish |
| 4,014,354 A | 3/1977 | Garrett |
| 4,019,522 A | 4/1977 | Elbreder |
| 4,033,008 A | 7/1977 | Warren et al. |
| 4,048,723 A | 9/1977 | Thorup |
| 4,051,571 A | 10/1977 | Ayers |
| 4,064,883 A | 12/1977 | Oldham |
| 4,133,339 A | 1/1979 | Naslund |
| 4,141,352 A | 2/1979 | Ebner et al. |
| 4,156,620 A | 5/1979 | Clemens |
| 4,173,828 A | 11/1979 | Lustig et al. |
| 4,177,434 A | 12/1979 | Ida |
| D254,162 S | 2/1980 | Barker |
| 4,192,035 A | 3/1980 | Kuris |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| RE30,536 E | 3/1981 | Perdreaux, Jr. |
| 4,255,693 A | 3/1981 | Keidl |
| 4,265,257 A | 5/1981 | Salyer |
| 4,268,933 A | 5/1981 | Papas |
| 4,271,382 A | 6/1981 | Maeda et al. |
| 4,271,384 A | 6/1981 | Beiling et al. |
| 4,271,854 A | 6/1981 | Bengtsson |
| 4,275,363 A | 6/1981 | Mishiro et al. |
| 4,288,883 A | 9/1981 | Dolinsky |
| 4,289,486 A | 9/1981 | Sargeant |
| 4,303,064 A | 12/1981 | Buffa |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| D265,698 S | 8/1982 | Roth |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D270,972 S | 10/1983 | Rosofsky |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| D274,018 S | 5/1984 | Usui |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |
| 4,490,114 A | 12/1984 | Kleesattel |
| 4,505,678 A | 3/1985 | Andersson |
| 4,517,701 A | 5/1985 | Stanford, Jr. |
| 4,519,111 A | 5/1985 | Cavazza |
| 4,522,355 A | 6/1985 | Moran |
| 4,522,595 A | 6/1985 | Selvidge |
| 4,543,679 A | 10/1985 | Rosofsky et al. |
| D281,202 S | 11/1985 | Thompson |
| 4,562,413 A | 12/1985 | Mishiro et al. |
| 4,564,794 A | 1/1986 | Kilen et al. |
| 4,571,768 A | 2/1986 | Kawashima |
| 4,576,190 A | 3/1986 | Youssef |
| 4,577,649 A | 3/1986 | Shimenkov |
| 4,578,033 A | 3/1986 | Mossle et al. |
| D283,374 S | 4/1986 | Cheuk-Yiu |
| 4,585,415 A | 4/1986 | Hommann |
| 4,586,521 A | 5/1986 | Urso |
| D284,236 S | 6/1986 | Collet |
| D284,528 S | 7/1986 | Jurado |
| 4,603,448 A | 8/1986 | Middleton et al. |
| 4,605,025 A | 8/1986 | McSpadden |
| 4,608,019 A | 8/1986 | Kumabe et al. |
| 4,610,043 A | 9/1986 | Vezjak |
| 4,617,695 A | 10/1986 | Amos et al. |
| 4,617,718 A | 10/1986 | Andersson |
| 4,619,009 A | 10/1986 | Rosenstatter |
| D287,073 S | 12/1986 | Thompson |
| 4,634,376 A | 1/1987 | Mossle et al. |

(56) References Cited

U.S. PATENT DOCUMENTS

| | | |
|---|---|---|
| 4,644,937 A | 2/1987 | Hommann |
| 4,655,198 A | 4/1987 | Hommann |
| 4,672,706 A | 6/1987 | Hill |
| D292,448 S | 10/1987 | Vianello |
| 4,698,869 A | 10/1987 | Mierau et al. |
| 4,706,322 A | 11/1987 | Nicolas |
| 4,706,695 A | 11/1987 | Urso |
| D294,885 S | 3/1988 | Mollenhoff |
| 4,729,142 A | 3/1988 | Yoshioka |
| D297,467 S | 8/1988 | McCann |
| 4,766,630 A | 8/1988 | Hegemann |
| 4,776,054 A | 10/1988 | Rauch |
| 4,787,847 A | 11/1988 | Martin et al. |
| 4,791,940 A | 12/1988 | Hirshfeld et al. |
| 4,800,608 A | 1/1989 | Key |
| 4,802,255 A | 2/1989 | Breuer et al. |
| 4,811,445 A | 3/1989 | Lagieski et al. |
| 4,820,153 A | 4/1989 | Romhild et al. |
| 4,820,154 A | 4/1989 | Romhild et al. |
| 4,827,550 A | 5/1989 | Graham et al. |
| 4,827,551 A | 5/1989 | Maser et al. |
| 4,827,552 A | 5/1989 | Bojar et al. |
| 4,832,063 A | 5/1989 | Smole |
| D301,770 S | 6/1989 | Bethany |
| 4,844,104 A | 7/1989 | Martin |
| 4,845,795 A | 7/1989 | Crawford et al. |
| 4,856,133 A | 8/1989 | Sanchez |
| 4,864,676 A | 9/1989 | Schaiper |
| D303,876 S | 10/1989 | Clemens et al. |
| 4,871,396 A | 10/1989 | Tsujita et al. |
| 4,873,496 A | 10/1989 | Ohgihara et al. |
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. |
| 4,887,052 A | 12/1989 | Murakami et al. |
| 4,892,191 A | 1/1990 | Nakamara |
| 4,908,902 A | 3/1990 | McNab et al. |
| 4,909,241 A * | 3/1990 | Burn ............ A61H 13/00 15/22.1 |
| 4,913,133 A | 4/1990 | Tichy |
| 4,913,176 A | 4/1990 | DeNiro |
| 4,922,936 A | 5/1990 | Buzzi et al. |
| D308,765 S | 6/1990 | Johnson |
| 4,974,278 A | 12/1990 | Hommann |
| 4,984,173 A | 1/1991 | Imam et al. |
| 4,989,287 A | 2/1991 | Scherer |
| 4,991,249 A | 2/1991 | Suroff |
| 4,995,403 A | 2/1991 | Beckman et al. |
| 5,000,684 A | 3/1991 | Odrich |
| 5,002,487 A | 3/1991 | Tichy |
| 5,007,127 A | 4/1991 | Paolo |
| 5,016,660 A | 5/1991 | Boggs |
| 5,020,179 A | 6/1991 | Scherer |
| 5,033,150 A | 7/1991 | Gross et al. |
| D318,918 S | 8/1991 | Hartwein |
| D319,363 S | 8/1991 | Uemura et al. |
| 5,046,212 A | 9/1991 | O'Conke |
| 5,050,625 A | 9/1991 | Siekmann |
| 5,054,149 A | 10/1991 | Si-Hoe et al. |
| D321,285 S | 11/1991 | Hirabayashi |
| 5,062,797 A | 11/1991 | Gonser |
| 5,067,223 A | 11/1991 | Bruno |
| D321,986 S | 12/1991 | Snyder et al. |
| 5,068,939 A | 12/1991 | Holland |
| 5,069,233 A | 12/1991 | Ritter |
| 5,069,621 A | 12/1991 | Paradis |
| 5,071,348 A | 12/1991 | Woog |
| 5,072,477 A | 12/1991 | Pai |
| 5,072,482 A | 12/1991 | Bojar et al. |
| 5,077,855 A | 1/1992 | Ambasz |
| 5,085,236 A | 2/1992 | Odneal et al. |
| 5,088,145 A | 2/1992 | Whitefield |
| D324,957 S | 3/1992 | Piano |
| 5,094,256 A | 3/1992 | Barth |
| 5,095,470 A | 3/1992 | Oka et al. |
| 5,100,321 A | 3/1992 | Coss et al. |
| 5,120,225 A | 6/1992 | Amit |
| 5,123,841 A | 6/1992 | Millner |
| 5,125,837 A | 6/1992 | Warrin et al. |
| 5,133,661 A | 7/1992 | Euvrard |
| 5,138,733 A | 8/1992 | Bock |
| 5,145,369 A | 9/1992 | Lustig et al. |
| 5,146,643 A | 9/1992 | Bojar et al. |
| 5,150,492 A | 9/1992 | Suroff |
| 5,151,030 A | 9/1992 | Comeaux |
| D330,116 S | 10/1992 | Crawford et al. |
| D330,286 S | 10/1992 | Curtis et al. |
| D330,458 S | 10/1992 | Curtis et al. |
| 5,152,394 A | 10/1992 | Hughes |
| 5,163,375 A | 11/1992 | Withers et al. |
| 5,165,131 A | 11/1992 | Suroff |
| 5,167,193 A | 12/1992 | Withers et al. |
| 5,169,313 A | 12/1992 | Kline |
| 5,170,809 A | 12/1992 | Imai et al. |
| 5,174,314 A | 12/1992 | Charatan |
| 5,176,157 A | 1/1993 | Mazza |
| 5,177,826 A | 1/1993 | Vrignaud et al. |
| 5,180,363 A | 1/1993 | Idemoto et al. |
| D332,873 S | 2/1993 | Hall |
| 5,183,063 A | 2/1993 | Ringle et al. |
| 5,183,156 A | 2/1993 | Bruno |
| 5,184,368 A | 2/1993 | Holland |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. |
| 5,193,678 A | 3/1993 | Janocik et al. |
| 5,198,732 A | 3/1993 | Morimoto |
| D334,472 S | 4/1993 | Curtis et al. |
| 5,201,092 A | 4/1993 | Colson |
| D335,579 S | 5/1993 | Chuang |
| 5,207,773 A | 5/1993 | Henderson |
| 5,213,434 A | 5/1993 | Hahn |
| 5,214,819 A | 6/1993 | Kirchner |
| 5,217,031 A | 6/1993 | Santoro |
| 5,224,500 A | 7/1993 | Stella |
| 5,226,206 A | 7/1993 | Davidovitz et al. |
| 5,236,358 A | 8/1993 | Sieffert |
| 5,245,117 A | 9/1993 | Withers et al. |
| 5,246,022 A | 9/1993 | Israel et al. |
| 5,247,716 A | 9/1993 | Bock |
| 5,253,382 A | 10/1993 | Beny |
| 5,261,430 A | 11/1993 | Mochel |
| 5,263,218 A | 11/1993 | Giuliani et al. |
| D341,943 S | 12/1993 | Si-Hoe |
| D342,160 S | 12/1993 | Curtis et al. |
| D342,161 S | 12/1993 | Curtis et al. |
| D342,162 S | 12/1993 | Curtis et al. |
| 5,267,579 A | 12/1993 | Bushberger |
| D343,064 S | 1/1994 | Reno |
| 5,279,314 A | 1/1994 | Poulos et al. |
| 5,289,604 A | 3/1994 | Kressner |
| 5,293,886 A | 3/1994 | Czapor |
| 5,294,896 A | 3/1994 | Kjellander et al. |
| D346,212 S | 4/1994 | Hosl |
| 5,299,723 A | 4/1994 | Hempel |
| 5,301,381 A | 4/1994 | Klupt |
| 5,305,492 A | 4/1994 | Giuliani et al. |
| D346,697 S | 5/1994 | O'Conke |
| 5,309,590 A | 5/1994 | Giuliani et al. |
| 5,309,591 A | 5/1994 | Hägele et al. |
| 5,311,632 A | 5/1994 | Center |
| 5,311,633 A | 5/1994 | Herzog et al. |
| 5,315,731 A | 5/1994 | Millar |
| D347,943 S | 6/1994 | Perry |
| 5,323,796 A | 6/1994 | Urso |
| 5,335,389 A | 8/1994 | Curtis et al. |
| 5,337,435 A | 8/1994 | Krasner et al. |
| 5,339,482 A | 8/1994 | Desimone et al. |
| 5,341,534 A | 8/1994 | Serbinski et al. |
| 5,341,537 A | 8/1994 | Curtis et al. |
| 5,351,358 A | 10/1994 | Larrimore |
| 5,353,460 A | 10/1994 | Bauman |

(56) References Cited

U.S. PATENT DOCUMENTS

| | | |
|---|---|---|
| 5,354,246 A | 10/1994 | Gotman |
| 5,355,638 A | 10/1994 | Hoffman |
| 5,358,328 A | 10/1994 | Inoue et al. |
| D352,396 S | 11/1994 | Curtis et al. |
| D352,829 S | 11/1994 | Perry |
| 5,359,747 A | 11/1994 | Amakasu |
| 5,365,627 A | 11/1994 | Jousson et al. |
| D353,490 S | 12/1994 | Hartwein |
| 5,369,831 A | 12/1994 | Bock |
| 5,371,915 A | 12/1994 | Key |
| 5,373,602 A | 12/1994 | Bang |
| D354,168 S | 1/1995 | Hartwein |
| 5,378,153 A | 1/1995 | Giuliani et al. |
| 5,381,576 A * | 1/1995 | Hwang ............... A61C 17/3481 15/22.1 |
| 5,383,242 A | 1/1995 | Bigler et al. |
| 5,392,483 A | 2/1995 | Heinzelman et al. |
| 5,393,229 A | 2/1995 | Ram |
| 5,396,678 A | 3/1995 | Bredall et al. |
| 5,398,368 A | 3/1995 | Elder |
| 5,400,811 A | 3/1995 | Meibauer |
| 5,404,608 A | 4/1995 | Hommann |
| 5,406,664 A | 4/1995 | Hukuba |
| 5,406,965 A | 4/1995 | Levine |
| D358,486 S | 5/1995 | Loew |
| D358,713 S | 5/1995 | Perry |
| D358,801 S | 5/1995 | Vos |
| 5,411,041 A | 5/1995 | Ritter |
| 5,412,827 A | 5/1995 | Muller et al. |
| 5,416,942 A | 5/1995 | Baldacci et al. |
| 5,419,346 A | 5/1995 | Tipp |
| 5,419,703 A | 5/1995 | Warrin et al. |
| D358,938 S | 6/1995 | Schneider et al. |
| 5,421,726 A | 6/1995 | Okada |
| 5,435,032 A | 7/1995 | McDougall |
| 5,438,726 A | 8/1995 | Leite |
| 5,446,940 A | 9/1995 | Curtis et al. |
| D363,605 S | 10/1995 | Kou et al. |
| 5,459,898 A | 10/1995 | Bacolot |
| 5,461,744 A | 10/1995 | Merbach |
| 5,467,494 A | 11/1995 | Muller et al. |
| 5,467,495 A | 11/1995 | Boland et al. |
| 5,482,466 A | 1/1996 | Haynes |
| 5,484,281 A | 1/1996 | Renow et al. |
| 5,496,256 A | 3/1996 | Bock et al. |
| 5,499,420 A | 3/1996 | Boland |
| 5,504,958 A | 4/1996 | Herzog |
| 5,504,959 A | 4/1996 | Yukawa et al. |
| 5,511,270 A | 4/1996 | Eliachar et al. |
| 5,511,275 A | 4/1996 | Volpenhein et al. |
| D370,125 S | 5/1996 | Craft et al. |
| 5,518,012 A | 5/1996 | Dolan et al. |
| D370,347 S | 6/1996 | Heinzelman et al. |
| 5,529,494 A | 6/1996 | Vlacancich |
| D371,242 S | 7/1996 | Shimatsu et al. |
| 5,530,981 A | 7/1996 | Chen |
| 5,544,382 A | 8/1996 | Giuliani et al. |
| 5,545,968 A | 8/1996 | Hilfinger et al. |
| 5,546,624 A | 8/1996 | Bock |
| 5,546,626 A | 8/1996 | Chung |
| 5,561,881 A | 10/1996 | Klinger et al. |
| D375,841 S | 11/1996 | Serbinski |
| 5,573,020 A | 11/1996 | Robinson |
| 5,577,285 A | 11/1996 | Drossler |
| D376,695 S | 12/1996 | Tveras |
| 5,579,786 A | 12/1996 | Wolk et al. |
| 5,584,690 A | 12/1996 | Maassarani |
| 5,588,452 A | 12/1996 | Peck |
| 5,606,984 A | 3/1997 | Gao |
| 5,609,170 A | 3/1997 | Roth |
| 5,613,258 A | 3/1997 | Hilfinger et al. |
| 5,613,259 A | 3/1997 | Craft et al. |
| 5,617,601 A | 4/1997 | McDougall |
| 5,617,602 A | 4/1997 | Okada |
| 5,618,275 A | 4/1997 | Bock |
| 5,619,766 A | 4/1997 | Zhadanov et al. |
| 5,623,746 A | 4/1997 | Ichiro |
| 5,625,916 A | 5/1997 | McDougall |
| 5,628,082 A | 5/1997 | Moskovich |
| D380,903 S | 7/1997 | Moskovich |
| D381,468 S | 7/1997 | Dolan et al. |
| 5,651,157 A | 7/1997 | Hahn |
| D382,407 S | 8/1997 | Craft et al. |
| 5,652,990 A | 8/1997 | Driesen et al. |
| 5,653,591 A | 8/1997 | Loge |
| 5,678,274 A | 10/1997 | Liu |
| 5,678,578 A | 10/1997 | Kossak et al. |
| D386,314 S | 11/1997 | Moskovich |
| 5,687,446 A | 11/1997 | Chen et al. |
| 5,689,850 A * | 11/1997 | Shekalim ............... A46B 13/02 15/145 |
| 5,697,117 A | 12/1997 | Craft |
| 5,700,146 A | 12/1997 | Kucar |
| RE35,712 E | 1/1998 | Murayama |
| 5,704,087 A | 1/1998 | Strub |
| 5,709,233 A | 1/1998 | Boland et al. |
| 5,718,667 A | 2/1998 | Sugimoto et al. |
| 5,732,433 A | 3/1998 | Göcking et al. |
| 5,735,011 A | 4/1998 | Asher |
| 5,738,575 A | 4/1998 | Bock |
| 5,742,972 A | 4/1998 | Bredall et al. |
| 5,749,380 A | 5/1998 | Zebuhr |
| 5,762,078 A | 6/1998 | Zebuhr |
| 5,775,346 A | 7/1998 | Szyszkowski |
| 5,784,742 A | 7/1998 | Giuliani et al. |
| 5,784,743 A | 7/1998 | Shek |
| D397,251 S | 8/1998 | Eguchi et al. |
| D397,254 S | 8/1998 | Moskovich |
| 5,787,908 A | 8/1998 | Robinson |
| 5,794,295 A | 8/1998 | Shen |
| 5,815,872 A | 10/1998 | Meginnis, III et al. |
| 5,816,271 A | 10/1998 | Urso |
| 5,822,821 A | 10/1998 | Sham |
| 5,827,064 A | 10/1998 | Bock |
| D400,713 S | 11/1998 | Solanki |
| 5,836,030 A | 11/1998 | Hazeu et al. |
| 5,842,244 A | 12/1998 | Hilfinger et al. |
| 5,850,655 A | 12/1998 | Göcking et al. |
| 5,851,514 A | 12/1998 | Hassan et al. |
| D403,511 S | 1/1999 | Serbinski |
| 5,855,216 A | 1/1999 | Robinson |
| 5,862,558 A | 1/1999 | Hilfinger et al. |
| 5,864,911 A | 2/1999 | Arnoux |
| 5,864,915 A | 2/1999 | Ra |
| 5,867,856 A | 2/1999 | Herzog |
| 5,875,797 A | 3/1999 | Chiang et al. |
| 5,893,175 A | 4/1999 | Cooper |
| 5,896,614 A | 4/1999 | Flewitt |
| 5,896,615 A | 4/1999 | Zaksenberg |
| 5,899,693 A | 5/1999 | Himeno et al. |
| 5,900,230 A | 5/1999 | Cutler |
| 5,901,397 A | 5/1999 | Hafele et al. |
| D410,787 S | 6/1999 | Barre et al. |
| 5,908,038 A | 6/1999 | Bennett |
| D411,769 S | 7/1999 | Wright |
| 5,921,254 A | 7/1999 | Carlucci et al. |
| 5,927,300 A | 7/1999 | Boland et al. |
| 5,927,976 A | 7/1999 | Wu |
| 5,930,858 A | 8/1999 | Jung |
| 5,931,170 A | 8/1999 | Wu |
| 5,934,908 A | 8/1999 | Woog et al. |
| 5,943,723 A | 8/1999 | Hilfinger et al. |
| 5,944,033 A | 8/1999 | Robinson |
| D413,694 S | 9/1999 | Bennett |
| D414,937 S | 10/1999 | Cornu et al. |
| D414,939 S | 10/1999 | Pedro, Jr. et al. |
| 5,974,613 A | 11/1999 | Herzog |
| 5,974,615 A | 11/1999 | Schwarz-Hartmann et al. |
| 5,980,541 A | 11/1999 | Tenzer |
| 5,987,681 A | 11/1999 | Hahn et al. |
| 5,991,957 A | 11/1999 | Watanabe |
| D417,960 S | 12/1999 | Moskovich et al. |
| 6,000,083 A | 12/1999 | Blaustein et al. |
| 6,009,589 A | 1/2000 | Driesen et al. |

(56) References Cited

U.S. PATENT DOCUMENTS

| | | |
|---|---|---|
| 6,021,538 A | 2/2000 | Kressner et al. |
| 6,026,828 A | 2/2000 | Altshuler |
| 6,032,313 A | 3/2000 | Tsang |
| 6,035,476 A | 3/2000 | Underwood et al. |
| 6,047,429 A | 4/2000 | Wu |
| 6,047,711 A | 4/2000 | Wagner |
| 6,050,818 A | 4/2000 | Boland et al. |
| RE36,699 E | 5/2000 | Murayama |
| D423,784 S | 5/2000 | Joulin |
| 6,065,176 A | 5/2000 | Watanabe et al. |
| 6,081,957 A | 7/2000 | Webb |
| 6,092,252 A | 7/2000 | Fischer et al. |
| 6,095,811 A | 8/2000 | Stearns |
| 6,102,700 A | 8/2000 | Haczek et al. |
| 6,106,294 A | 8/2000 | Daniel |
| 6,138,310 A | 10/2000 | Porper et al. |
| 6,140,723 A | 10/2000 | Matsui et al. |
| 6,148,462 A | 11/2000 | Zseng |
| D434,563 S | 12/2000 | Lim et al. |
| 6,154,912 A | 12/2000 | Li |
| 6,162,202 A | 12/2000 | Sicurelli et al. |
| 6,164,967 A | 12/2000 | Sale et al. |
| 6,165,131 A | 12/2000 | Cuse et al. |
| D437,090 S | 1/2001 | Lang et al. |
| D437,091 S | 1/2001 | Lang et al. |
| 6,178,579 B1 | 1/2001 | Blaustein et al. |
| D437,663 S | 2/2001 | Lang et al. |
| D437,976 S | 2/2001 | Narayanan et al. |
| D437,977 S | 2/2001 | Lang et al. |
| D438,306 S | 2/2001 | Narayanan |
| 6,183,254 B1 | 2/2001 | Cohen |
| 6,195,828 B1 | 3/2001 | Fritsch |
| 6,202,242 B1 | 3/2001 | Salmon et al. |
| 6,203,320 B1 | 3/2001 | Williams et al. |
| 6,220,857 B1 | 4/2001 | Abels |
| 6,230,354 B1 | 5/2001 | Sproat |
| 6,230,717 B1 | 5/2001 | Marx et al. |
| 6,233,773 B1 | 5/2001 | Karge et al. |
| 6,237,178 B1 | 5/2001 | Krammer et al. |
| D444,629 S | 7/2001 | Etter et al. |
| 6,253,404 B1 | 7/2001 | Boland et al. |
| 6,267,593 B1 | 7/2001 | Haczek et al. |
| 6,299,444 B1 | 10/2001 | Cohen |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,349,442 B1 | 2/2002 | Cohen et al. |
| 6,353,956 B1 | 3/2002 | Berge |
| 6,360,395 B2 | 3/2002 | Blaustein et al. |
| 6,360,398 B1 | 3/2002 | Wiegner et al. |
| 6,363,565 B1 | 4/2002 | Paffrath |
| 6,365,108 B1 | 4/2002 | Philyaw |
| 6,367,108 B1 | 4/2002 | Fritsch et al. |
| 6,374,448 B2 | 4/2002 | Seifert |
| 6,375,459 B1 | 4/2002 | Kamen et al. |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 | 9/2002 | Wu |
| 6,453,499 B1 | 9/2002 | Leuermann |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B2 | 6/2003 | Cheng |
| 6,581,234 B2 | 6/2003 | Lee et al. |
| 6,588,042 B2 | 7/2003 | Fritsch et al. |
| 6,599,048 B2 | 7/2003 | Kuo |
| 6,609,527 B2 | 8/2003 | Brown |
| 6,609,910 B2 | 8/2003 | Narayanan |
| 6,619,219 B2 | 9/2003 | Marcon et al. |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,659,674 B2 | 12/2003 | Carlucci et al. |
| 6,665,901 B2 | 12/2003 | Driesen et al. |
| 6,691,363 B2 | 2/2004 | Huen |
| 6,701,565 B2 | 3/2004 | Hafemann |
| 6,709,185 B2 | 3/2004 | Lefevre |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,766,807 B2 | 7/2004 | Piccolo et al. |
| 6,779,126 B1 | 8/2004 | Lin et al. |
| 6,779,215 B2 | 8/2004 | Hartman et al. |
| 6,785,926 B2 | 9/2004 | Green |
| 6,785,929 B2 | 9/2004 | Fritsch et al. |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,808,331 B2 | 10/2004 | Hall et al. |
| 6,810,550 B1 | 11/2004 | Wuelknitz et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |
| 6,827,910 B2 | 12/2004 | Chen |
| 6,829,801 B2 | 12/2004 | Schutz |
| 6,832,819 B1 | 12/2004 | Weihrauch |
| D500,599 S | 1/2005 | Callaghan |
| D501,084 S | 1/2005 | Schaefer et al. |
| 6,836,917 B2 | 1/2005 | Blaustein et al. |
| 6,845,537 B2 | 1/2005 | Wong |
| 6,848,141 B2 | 2/2005 | Eliav et al. |
| 6,851,150 B2 | 2/2005 | Chiang |
| 6,851,153 B2 | 2/2005 | Lehman |
| 6,854,965 B2 | 2/2005 | Ebner et al. |
| 6,862,771 B1 | 3/2005 | Muller |
| 6,871,373 B2 | 3/2005 | Driesen et al. |
| 6,874,509 B2 | 4/2005 | Bergman |
| 6,886,207 B1 | 5/2005 | Solanki |
| 6,889,401 B2 | 5/2005 | Fattori et al. |
| 6,889,829 B2 | 5/2005 | Lev et al. |
| 6,892,412 B2 | 5/2005 | Gatzemeyer et al. |
| 6,892,413 B2 | 5/2005 | Blaustein et al. |
| 6,895,625 B2 | 5/2005 | Lev et al. |
| 6,895,629 B1 | 5/2005 | Wenzler |
| 6,902,337 B1 | 6/2005 | Kuo |
| 6,907,636 B2 | 6/2005 | Hafemann |
| 6,918,153 B2 | 7/2005 | Gruber |
| 6,920,659 B2 | 7/2005 | Cacka et al. |
| 6,920,660 B2 | 7/2005 | Lam |
| 6,928,685 B1 | 8/2005 | Blaustein et al. |
| 6,931,688 B2 | 8/2005 | Moskovich et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |

(56) References Cited

U.S. PATENT DOCUMENTS

| | | |
|---|---|---|
| 6,945,397 B2 | 9/2005 | Brattesani et al. |
| 6,948,209 B2 | 9/2005 | Chan |
| 6,952,854 B2 | 10/2005 | Blaustein et al. |
| 6,952,855 B2 | 10/2005 | Lev et al. |
| 6,954,961 B2 | 10/2005 | Ferber et al. |
| 6,955,539 B2 | 10/2005 | Shortt et al. |
| 6,957,468 B2 | 10/2005 | Driesen et al. |
| 6,957,469 B2 | 10/2005 | Davies |
| 6,966,093 B2 | 11/2005 | Eliav et al. |
| 6,973,694 B2 | 12/2005 | Schutz et al. |
| 6,983,507 B2 | 1/2006 | McDougall |
| 6,988,777 B2 | 1/2006 | Pfenniger et al. |
| 6,990,706 B2 | 1/2006 | Broecker et al. |
| D515,318 S | 2/2006 | Chan et al. |
| 6,993,803 B2 | 2/2006 | Chan |
| 6,997,191 B2 | 2/2006 | Nudo, Sr. |
| 7,007,331 B2 | 3/2006 | Davies et al. |
| 7,008,225 B2 | 3/2006 | Ito et al. |
| 7,020,925 B1 | 4/2006 | Gitelis |
| 7,021,851 B1 | 4/2006 | King |
| 7,024,717 B2 | 4/2006 | Hilscher et al. |
| 7,024,718 B2 | 4/2006 | Chu |
| 7,036,180 B2 | 5/2006 | Hanlon |
| 7,055,205 B2 | 6/2006 | Aoyama |
| 7,059,334 B2 | 6/2006 | Dougan et al. |
| 7,065,821 B2 | 6/2006 | Fattori |
| RE39,185 E | 7/2006 | Noe et al. |
| 7,070,354 B1 | 7/2006 | Gutierrez-Caro |
| 7,080,980 B2 | 7/2006 | Klupt |
| 7,082,638 B2 | 8/2006 | Koh |
| 7,082,950 B2 | 8/2006 | Kossak et al. |
| 7,086,111 B2 | 8/2006 | Hilscher et al. |
| 7,089,621 B2 | 8/2006 | Hohlbein |
| 7,120,960 B2 | 10/2006 | Hilscher et al. |
| 7,122,921 B2 | 10/2006 | Hall et al. |
| 7,124,461 B2 | 10/2006 | Blaustein et al. |
| 7,124,462 B2 | 10/2006 | Lee |
| 7,128,492 B1 | 10/2006 | Thames, Jr. |
| 7,137,136 B1 | 11/2006 | Gatzemeyer et al. |
| 7,140,058 B2 | 11/2006 | Gatzemeyer et al. |
| 7,146,675 B2 | 12/2006 | Ansari et al. |
| 7,162,764 B2 | 1/2007 | Drossler et al. |
| 7,162,767 B2 | 1/2007 | Pfenniger et al. |
| 7,168,122 B1 | 1/2007 | Riddell |
| 7,168,125 B1 | 1/2007 | Hohlbein |
| 7,174,596 B2 | 2/2007 | Fischer et al. |
| 7,175,238 B1 | 2/2007 | Barman |
| 7,181,799 B2 | 2/2007 | Gavney, Jr. et al. |
| 7,185,383 B2 | 3/2007 | Gatzemeyer et al. |
| 7,186,226 B2 | 3/2007 | Woolley |
| D540,542 S | 4/2007 | Harada |
| 7,198,487 B2 | 4/2007 | Luettgen et al. |
| 7,207,080 B2 | 4/2007 | Hilscher et al. |
| 7,210,184 B2 | 5/2007 | Eliav et al. |
| 7,213,293 B1 | 5/2007 | Schraga |
| 7,213,995 B2 | 5/2007 | Bravo-Loubriel |
| 7,217,332 B2 | 5/2007 | Brown, Jr. et al. |
| 7,222,381 B2 | 5/2007 | Kraemer |
| 7,222,382 B2 | 5/2007 | Choi et al. |
| 7,225,494 B2 | 6/2007 | Chan et al. |
| 7,228,583 B2 | 6/2007 | Chan et al. |
| 7,234,192 B2 | 6/2007 | Barbar |
| 7,469,440 B2 | 12/2008 | Boland et al. |
| 7,554,225 B2 | 6/2009 | Kraus et al. |
| 7,732,952 B1 | 6/2010 | Taylor |
| 7,857,623 B2 | 12/2010 | Grez |
| 8,032,964 B2 | 10/2011 | Farrell et al. |
| 8,196,245 B2 | 6/2012 | Schwarz-Hartmann et al. |
| 8,256,979 B2 | 9/2012 | Hilscher et al. |
| 8,418,300 B2 | 4/2013 | Miller et al. |
| 8,453,285 B2 | 6/2013 | Dickie |
| 8,769,758 B2 | 7/2014 | Jungnickel et al. |
| 8,943,634 B2 | 2/2015 | Sokol |
| 9,468,511 B2 | 10/2016 | Garrigues et al. |
| 2001/0035194 A1 | 11/2001 | Narayanan |
| 2001/0039955 A1 | 11/2001 | Winters et al. |
| 2001/0054563 A1 | 12/2001 | Lang et al. |
| 2002/0017474 A1 | 2/2002 | Blaustein et al. |
| 2002/0029988 A1 | 3/2002 | Blaustein et al. |
| 2002/0032941 A1 | 3/2002 | Blaustein et al. |
| 2002/0039720 A1 | 4/2002 | Marx et al. |
| 2002/0059685 A1 | 5/2002 | Paffrath |
| 2002/0078514 A1 | 6/2002 | Blaustein et al. |
| 2002/0084707 A1 | 7/2002 | Tang |
| 2002/0088068 A1 | 7/2002 | Levy et al. |
| 2002/0090252 A1 | 7/2002 | Hall et al. |
| 2002/0092104 A1 | 7/2002 | Ferber |
| 2002/0095734 A1 | 7/2002 | Wong |
| 2002/0100134 A1 | 8/2002 | Dunn et al. |
| 2002/0106607 A1 | 8/2002 | Horowitz |
| 2002/0137728 A1 | 9/2002 | Montgomery |
| 2002/0138926 A1 | 10/2002 | Brown, Jr. et al. |
| 2002/0152563 A1 | 10/2002 | Sato |
| 2002/0152564 A1 | 10/2002 | Blaustein et al. |
| 2002/0152565 A1 | 10/2002 | Klupt |
| 2002/0174498 A1 | 11/2002 | Li |
| 2002/0178519 A1 | 12/2002 | Zarlengo |
| 2003/0005544 A1 | 1/2003 | Felix |
| 2003/0033679 A1 | 2/2003 | Fattori et al. |
| 2003/0033680 A1 | 2/2003 | Davies et al. |
| 2003/0041396 A1 | 3/2003 | Dickie |
| 2003/0064348 A1 | 4/2003 | Sokol et al. |
| 2003/0066145 A1 | 4/2003 | Prineppi |
| 2003/0074751 A1 | 4/2003 | Wu |
| 2003/0079305 A1 | 5/2003 | Takahata et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0097723 A1 | 5/2003 | Li |
| 2003/0099502 A1 | 5/2003 | Lai |
| 2003/0101526 A1 | 6/2003 | Hilscher |
| 2003/0106565 A1 | 6/2003 | Andrews |
| 2003/0140435 A1 | 7/2003 | Eliav et al. |
| 2003/0140437 A1 | 7/2003 | Eliav et al. |
| 2003/0140937 A1 | 7/2003 | Cook |
| 2003/0150474 A1 | 8/2003 | Doyscher |
| 2003/0154567 A1 | 8/2003 | Drossler et al. |
| 2003/0154568 A1 | 8/2003 | Boland et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182746 A1 | 10/2003 | Fattori et al. |
| 2003/0192139 A1 | 10/2003 | Fattori et al. |
| 2003/0196283 A1 | 10/2003 | Eliav et al. |
| 2003/0196677 A1 | 10/2003 | Wiseman |
| 2003/0213075 A1 | 11/2003 | Hui et al. |
| 2003/0221267 A1 | 12/2003 | Chan |
| 2003/0221269 A1 | 12/2003 | Zhuan |
| 2003/0226223 A1 | 12/2003 | Chan |
| 2004/0010870 A1 | 1/2004 | McNair |
| 2004/0010871 A1 | 1/2004 | Nishinaka et al. |
| 2004/0016068 A1* | 1/2004 | Lee .............. A61C 17/3418 15/22.1 |
| 2004/0016069 A1 | 1/2004 | Lee |
| 2004/0034951 A1 | 2/2004 | Davies et al. |
| 2004/0045106 A1 | 3/2004 | Lam |
| 2004/0045107 A1 | 3/2004 | Egeresi |
| 2004/0049867 A1 | 3/2004 | Hui |
| 2004/0049868 A1 | 3/2004 | Ng |
| 2004/0060137 A1 | 4/2004 | Eliav |
| 2004/0063603 A1 | 4/2004 | Dave et al. |
| 2004/0068809 A1* | 4/2004 | Weng .............. A61C 17/225 15/22.1 |
| 2004/0068811 A1 | 4/2004 | Fulop et al. |
| 2004/0074026 A1 | 4/2004 | Blaustein et al. |
| 2004/0083566 A1 | 5/2004 | Blaustein et al. |
| 2004/0087882 A1 | 5/2004 | Roberts et al. |
| 2004/0088806 A1 | 5/2004 | DePuydt et al. |
| 2004/0088807 A1 | 5/2004 | Blaustein et al. |
| 2004/0091834 A1 | 5/2004 | Rizoiu et al. |
| 2004/0107521 A1 | 6/2004 | Chan et al. |
| 2004/0119344 A1 | 6/2004 | Lau et al. |
| 2004/0123409 A1 | 7/2004 | Dickie |
| 2004/0128778 A1 | 7/2004 | Wong |

(56) References Cited

U.S. PATENT DOCUMENTS

| | | | |
|---|---|---|---|
| 2004/0129296 A1 | 7/2004 | Treacy et al. | |
| 2004/0134001 A1 | 7/2004 | Chan | |
| 2004/0143917 A1 | 7/2004 | Ek | |
| 2004/0154112 A1 | 8/2004 | Braun et al. | |
| 2004/0163191 A1 | 8/2004 | Cuffaro et al. | |
| 2004/0168269 A1 | 9/2004 | Kunita et al. | |
| 2004/0168272 A1 | 9/2004 | Prineppi | |
| 2004/0177458 A1 | 9/2004 | Chan et al. | |
| 2004/0187889 A1 | 9/2004 | Kemp et al. | |
| 2004/0200016 A1 | 10/2004 | Chan et al. | |
| 2005/0004498 A1 | 1/2005 | Klupt | |
| 2005/0008986 A1 | 1/2005 | Sokol et al. | |
| 2005/0081315 A1* | 4/2005 | Kwong | A61C 17/3436 15/22.1 |
| 2005/0102773 A1 | 5/2005 | Obermann et al. | |
| 2005/0144745 A1 | 7/2005 | Russell | |
| 2005/0189000 A1 | 9/2005 | Cacka et al. | |
| 2005/0255427 A1 | 11/2005 | Shortt et al. | |
| 2005/0266376 A1 | 12/2005 | Sokol et al. | |
| 2005/0284501 A1* | 12/2005 | Rehkemper | A61C 15/047 132/322 |
| 2006/0010622 A1* | 1/2006 | Naruse | A61C 17/3436 15/22.1 |
| 2006/0010624 A1 | 1/2006 | Cleland | |
| 2006/0078844 A1 | 4/2006 | Goldman et al. | |
| 2006/0101598 A1* | 5/2006 | Fujimoto | A61C 17/3445 15/22.2 |
| 2006/0168744 A1* | 8/2006 | Butler | A61C 17/222 15/22.1 |
| 2007/0151051 A1 | 7/2007 | Filsouf | |
| 2007/0209127 A1 | 9/2007 | DeVitis | |
| 2008/0115300 A1* | 5/2008 | Spooner | A61C 17/3427 15/22.1 |
| 2008/0213731 A1 | 9/2008 | Fishburne | |
| 2008/0307591 A1 | 12/2008 | Farrell et al. | |
| 2009/0019650 A1 | 1/2009 | Grez et al. | |
| 2009/0019651 A1 | 1/2009 | Dickie | |
| 2009/0178215 A1 | 7/2009 | Gall | |
| 2009/0183324 A1* | 7/2009 | Fischer | A61C 17/34 15/22.1 |
| 2010/0055634 A1 | 3/2010 | Spaulding et al. | |
| 2010/0132139 A1 | 6/2010 | Jungnickel | |
| 2010/0186179 A1 | 7/2010 | Miller | |
| 2011/0010874 A1 | 1/2011 | Dickie | |
| 2011/0041268 A1 | 2/2011 | Iwahori et al. | |
| 2011/0047729 A1 | 3/2011 | Iwahori | |
| 2011/0083288 A1 | 4/2011 | Kressner | |
| 2012/0112566 A1 | 5/2012 | Doll | |
| 2012/0192366 A1 | 8/2012 | Cobabe | |
| 2012/0198635 A1 | 8/2012 | Hilscher | |
| 2012/0216358 A1 | 8/2012 | Kloster | |
| 2012/0279002 A1* | 11/2012 | Sokol | A61C 17/3481 15/22.1 |
| 2013/0239342 A1 | 9/2013 | Hilscher et al. | |
| 2014/0157532 A1 | 6/2014 | Hilscher et al. | |
| 2014/0259469 A1 | 9/2014 | Garrigues | |
| 2014/0259474 A1 | 9/2014 | Sokol et al. | |
| 2015/0107035 A1 | 4/2015 | Sokol et al. | |
| 2015/0173874 A1* | 6/2015 | Johnson | A61C 17/3454 15/22.1 |
| 2015/0297327 A1 | 10/2015 | Miller | |
| 2015/0327965 A1 | 11/2015 | Garrigues | |
| 2016/0151133 A1 | 6/2016 | Luettgen et al. | |
| 2017/0189151 A1 | 7/2017 | Fischer et al. | |
| 2017/0319311 A1 | 11/2017 | Luettgen et al. | |
| 2018/0008388 A1 | 1/2018 | Lee | |
| 2018/0049854 A1 | 2/2018 | Hall | |
| 2018/0140404 A1 | 5/2018 | Schaefer et al. | |
| 2018/0168332 A1 | 6/2018 | Woodard et al. | |

FOREIGN PATENT DOCUMENTS

| | | |
|---|---|---|
| CN | 1658807 | 8/2005 |
| CN | 1886885 | 12/2006 |
| CN | 201223467 | 4/2009 |
| CN | 102026588 | 4/2011 |
| CN | 102111032 | 6/2011 |
| DE | 243224 | 4/1910 |
| DE | 2019003 | 11/1971 |
| DE | 1766651 | 12/1981 |
| DE | 3431481 | 2/1986 |
| DE | 3512190 | 10/1986 |
| DE | 8626725 | 5/1987 |
| DE | 3736308 | 7/1989 |
| DE | 4142404 | 7/1991 |
| DE | 4003305 | 8/1991 |
| DE | 4223195 | 1/1994 |
| DE | 4223196 | 1/1994 |
| DE | 4226658 | 2/1994 |
| DE | 4226659 | 2/1994 |
| DE | 4241576 | 6/1994 |
| DE | 4309078 | 9/1994 |
| DE | 29715234 | 12/1997 |
| DE | 29919053 | 12/2000 |
| DE | 19961447 | 7/2001 |
| DE | 20319996 | 3/2004 |
| DE | 102006061381 | 6/2008 |
| DE | 102007063150 | * 12/2008 |
| EP | 0210094 | 1/1987 |
| EP | 0354352 | 2/1990 |
| EP | 0661025 | 7/1995 |
| EP | 0704180 | 4/1996 |
| EP | 0968686 | 1/2000 |
| EP | 1072233 | * 1/2001 |
| FR | 429447 | 9/1911 |
| FR | 1171337 | 1/1959 |
| GB | 477799 | 1/1938 |
| GB | 500517 | 2/1939 |
| GB | 838564 | 6/1960 |
| GB | 899618 | 6/1962 |
| GB | 1583558 | 8/1977 |
| GB | 2175494 | 12/1986 |
| GB | 2250428 | 6/1992 |
| GB | 2399492 | * 9/2004 |
| JP | 53029847 | 3/1978 |
| JP | 53033753 | 3/1978 |
| JP | 3222905 | 10/1991 |
| JP | 2001-198145 | * 7/2001 |
| JP | 2006-55178 | * 3/2006 |
| SE | 324221 | 5/1970 |
| WO | WO 91/13570 | 9/1991 |
| WO | WO 91/19437 | 12/1991 |
| WO | WO 92/10146 | 6/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | 96/03900 | * 2/1996 |
| WO | 96/38100 | * 12/1996 |
| WO | WO 98/47443 | 10/1998 |
| WO | WO 01/28452 | 4/2001 |
| WO | WO 01/45582 | 6/2001 |
| WO | WO 02/071970 | 9/2002 |
| WO | WO 02/071971 | 9/2002 |
| WO | WO 05/063143 | 7/2005 |
| WO | 2006/012974 | * 2/2006 |
| WO | WO 2006/012974 | 2/2006 |
| WO | WO 2008/070730 | 6/2008 |
| WO | WO 2014/145890 | 9/2014 |
| WO | WO 2014/150418 | 9/2014 |

OTHER PUBLICATIONS

Teledyne Water Pik "Plaque Control 3000" plaque removal instrument (Jul. 1991).

American Dentronics Incorporated "Soniplak" sonic plaque removal system (May 1993).

Teledyne Water Pik "Sensonic" Toothbrush, sales brochure (at least as early as Sep. 1994).

(56) References Cited

OTHER PUBLICATIONS

International Search Report and Written Opinion, PCT Application No. PCT/US2012/036092, 7 pages, dated Jul. 10, 2012.

\* cited by examiner

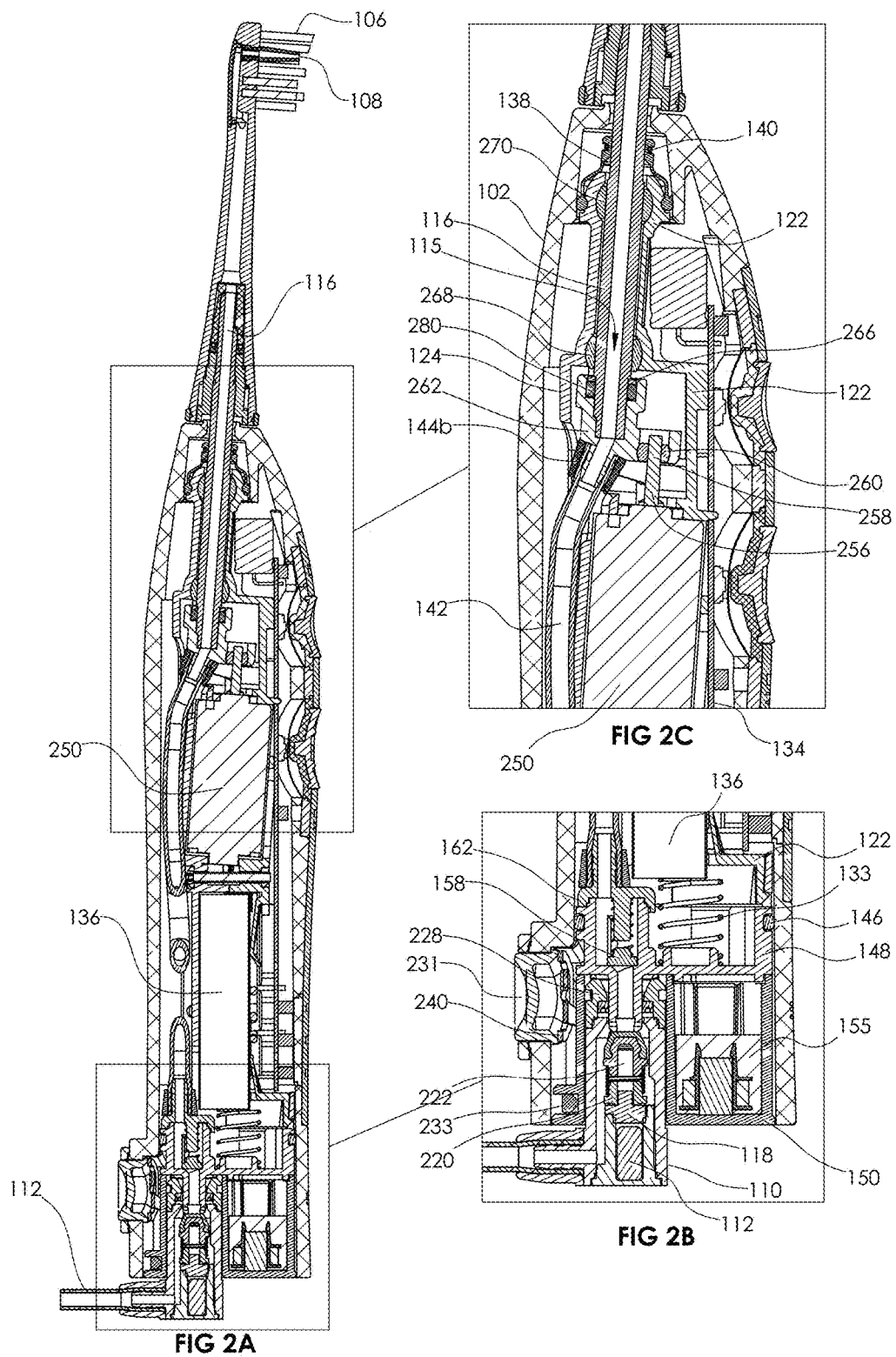

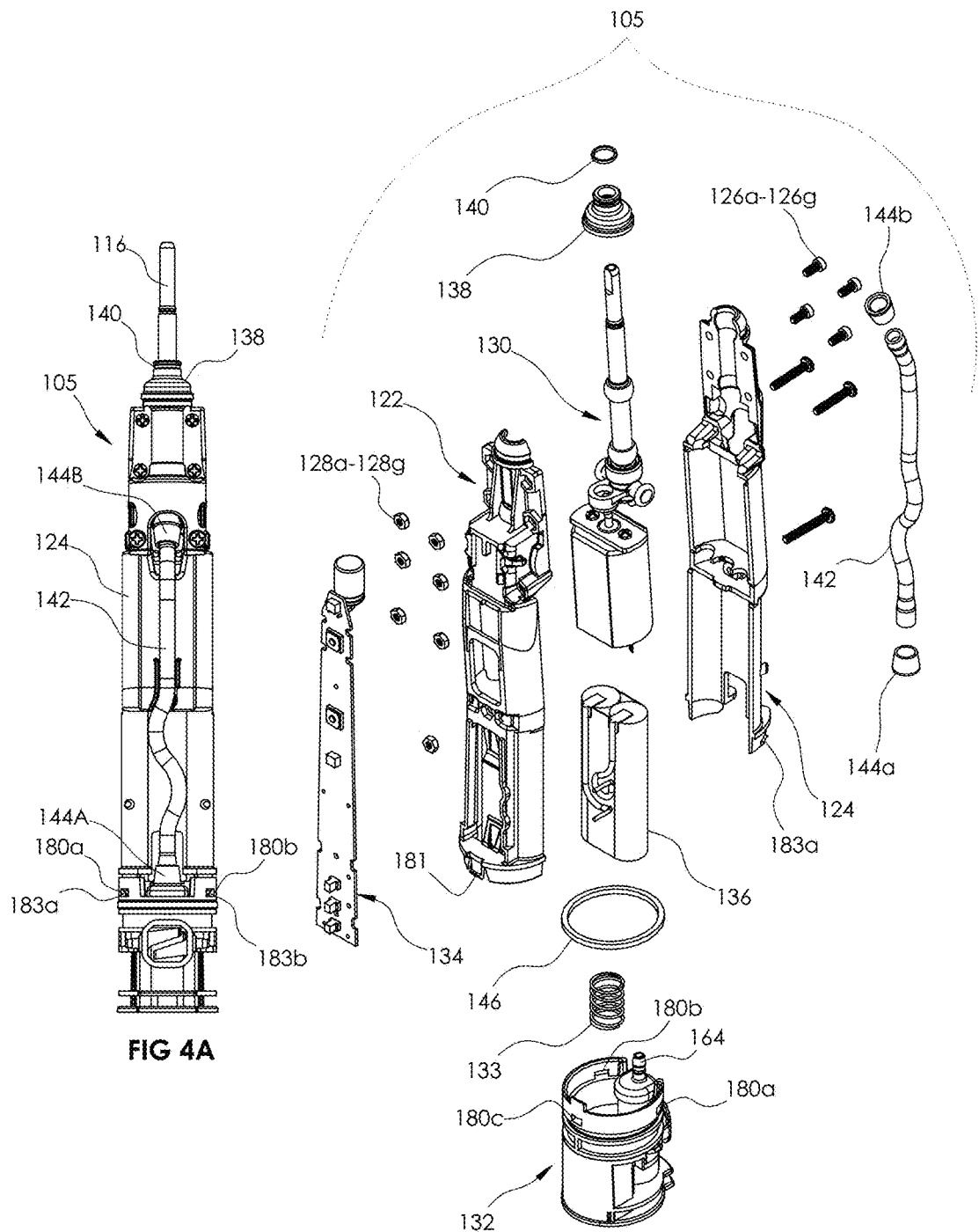

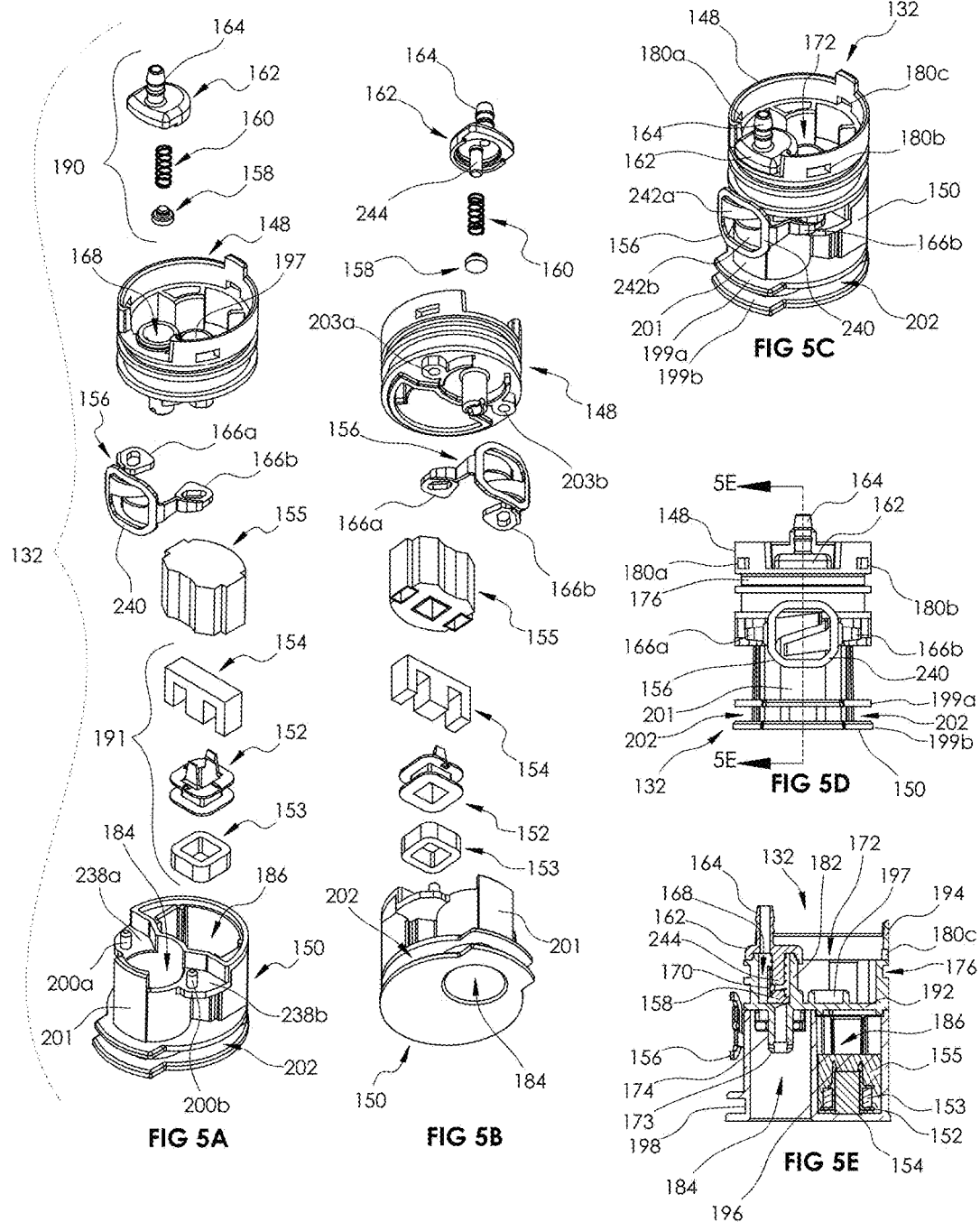

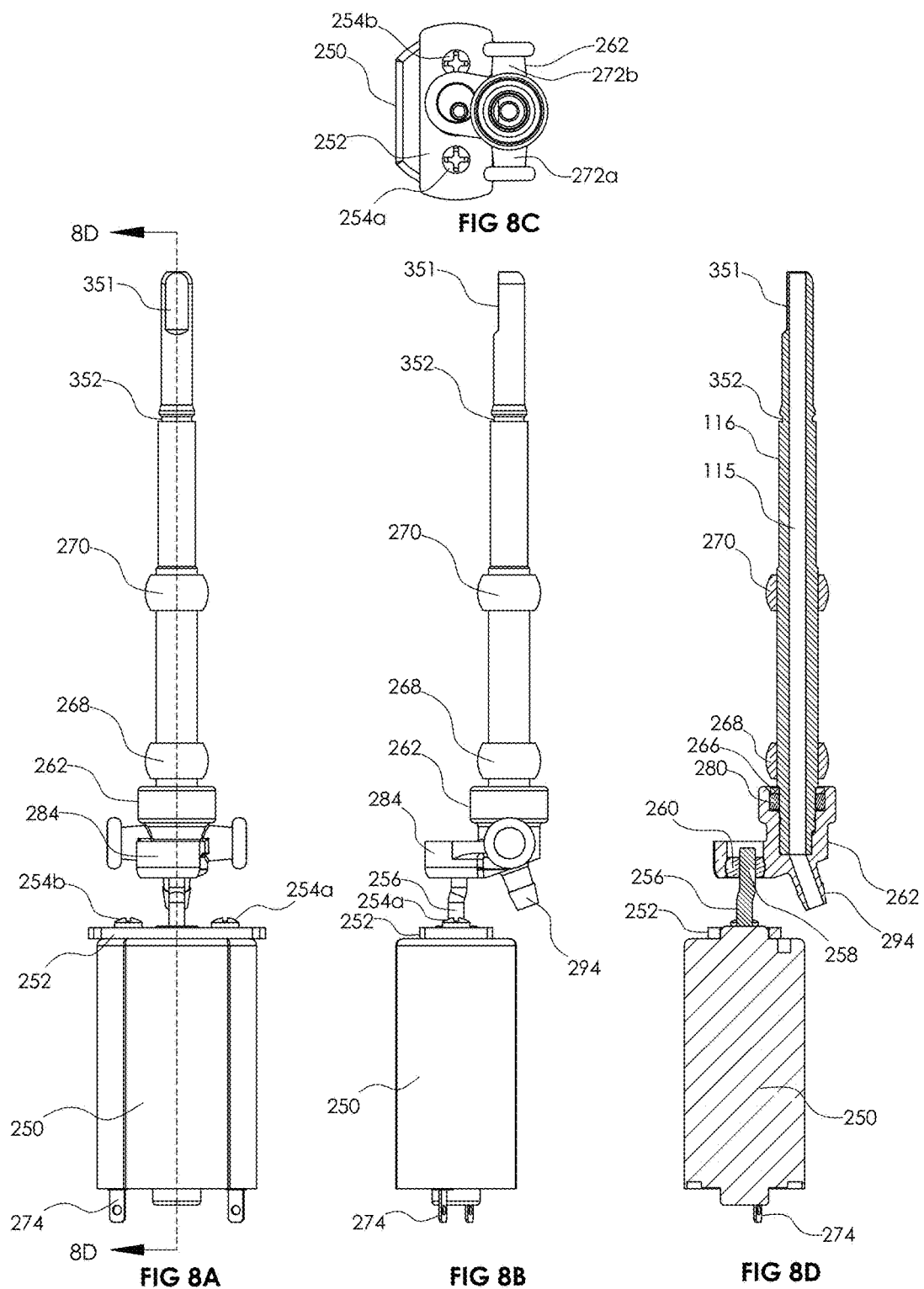

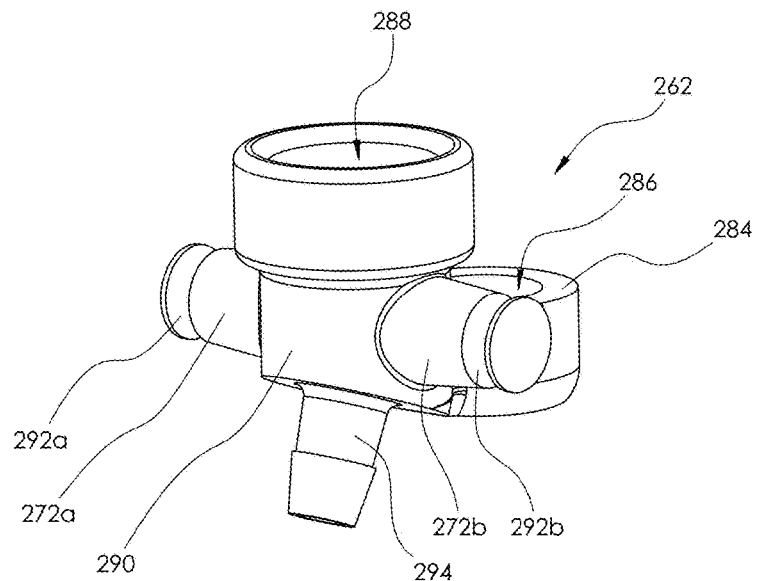
FIG 9A
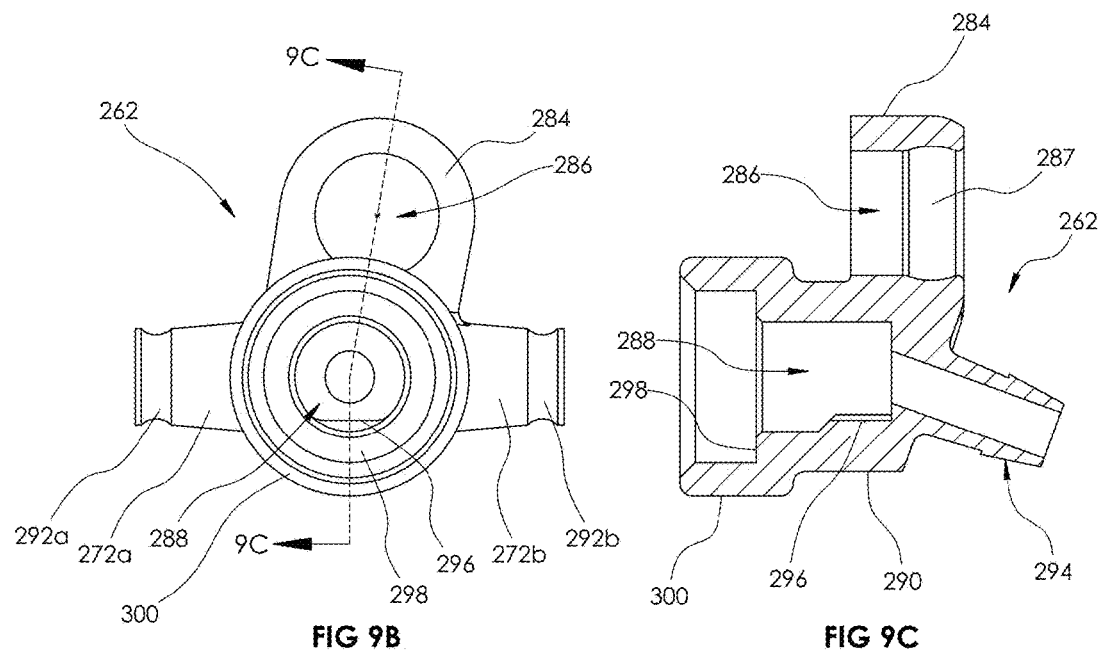
FIG 9B
FIG 9C

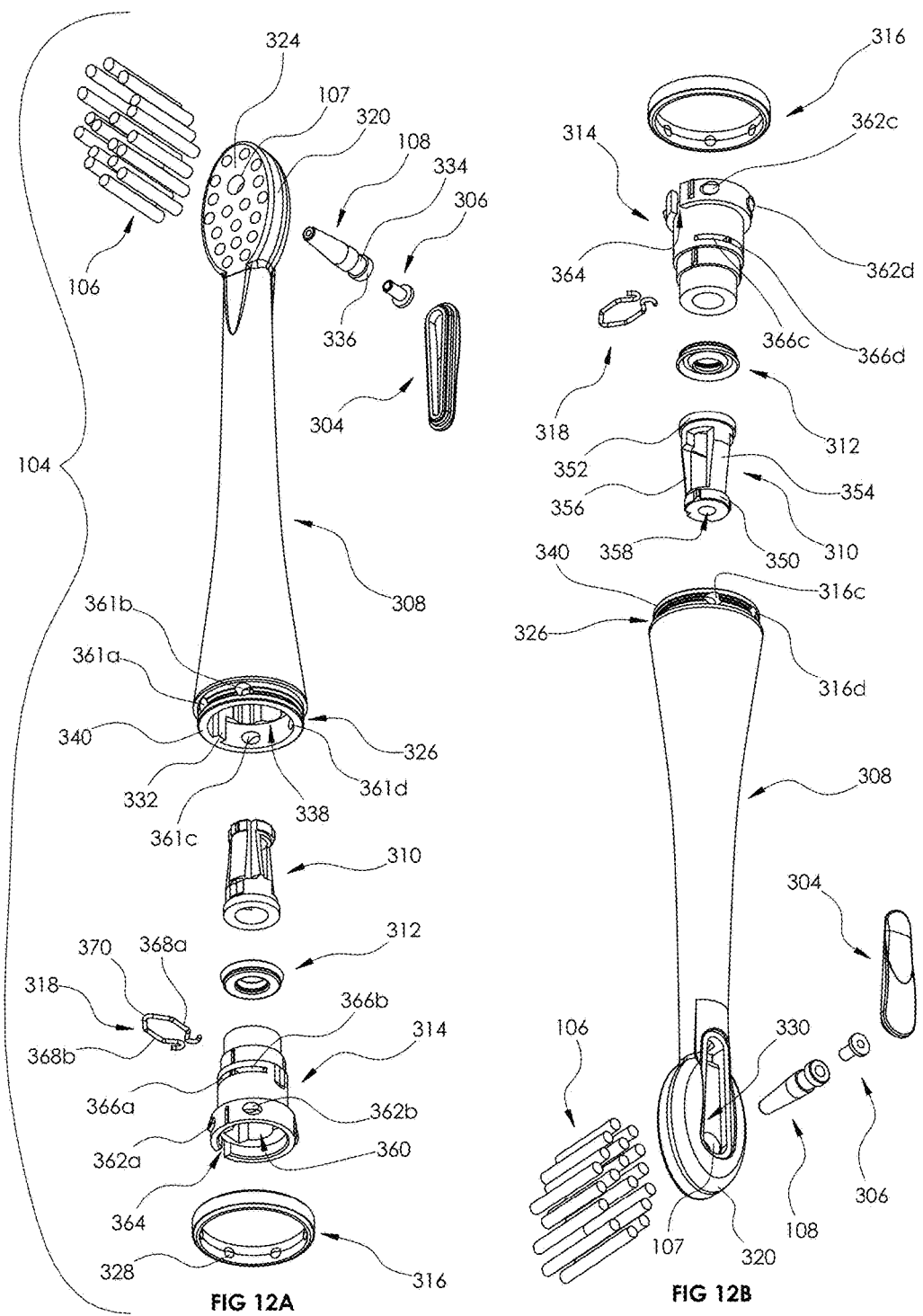

LATCHED

UNLATCHED

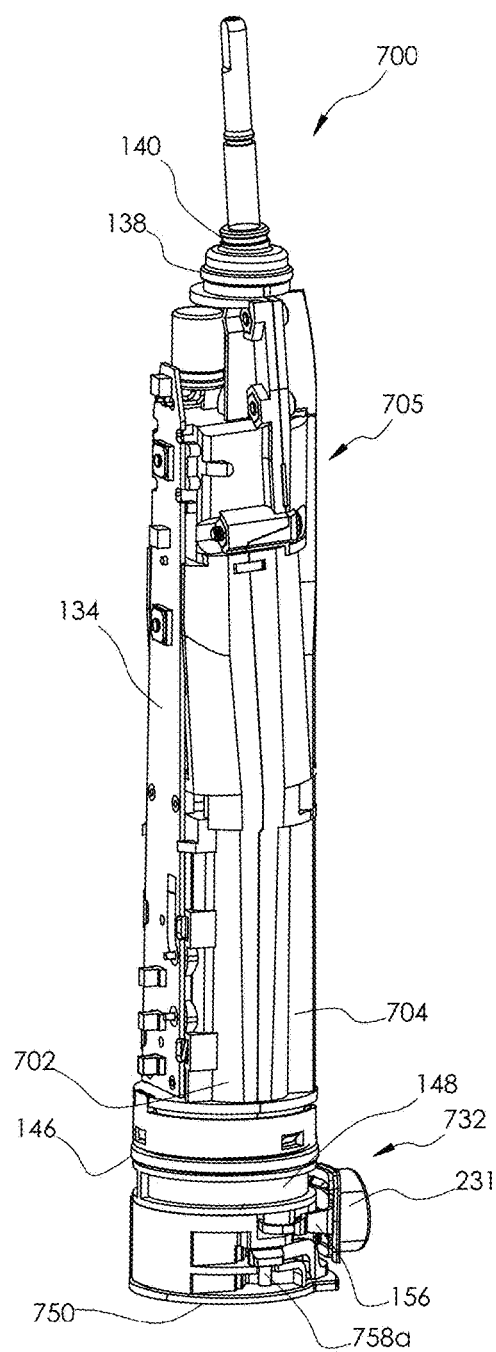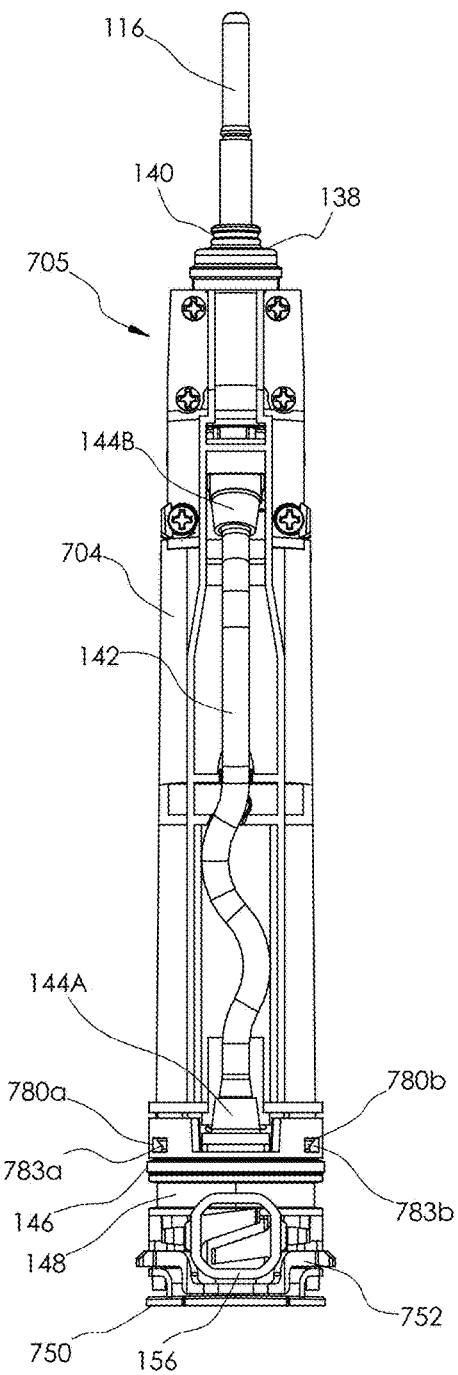
FIG 20A
FIG 20B

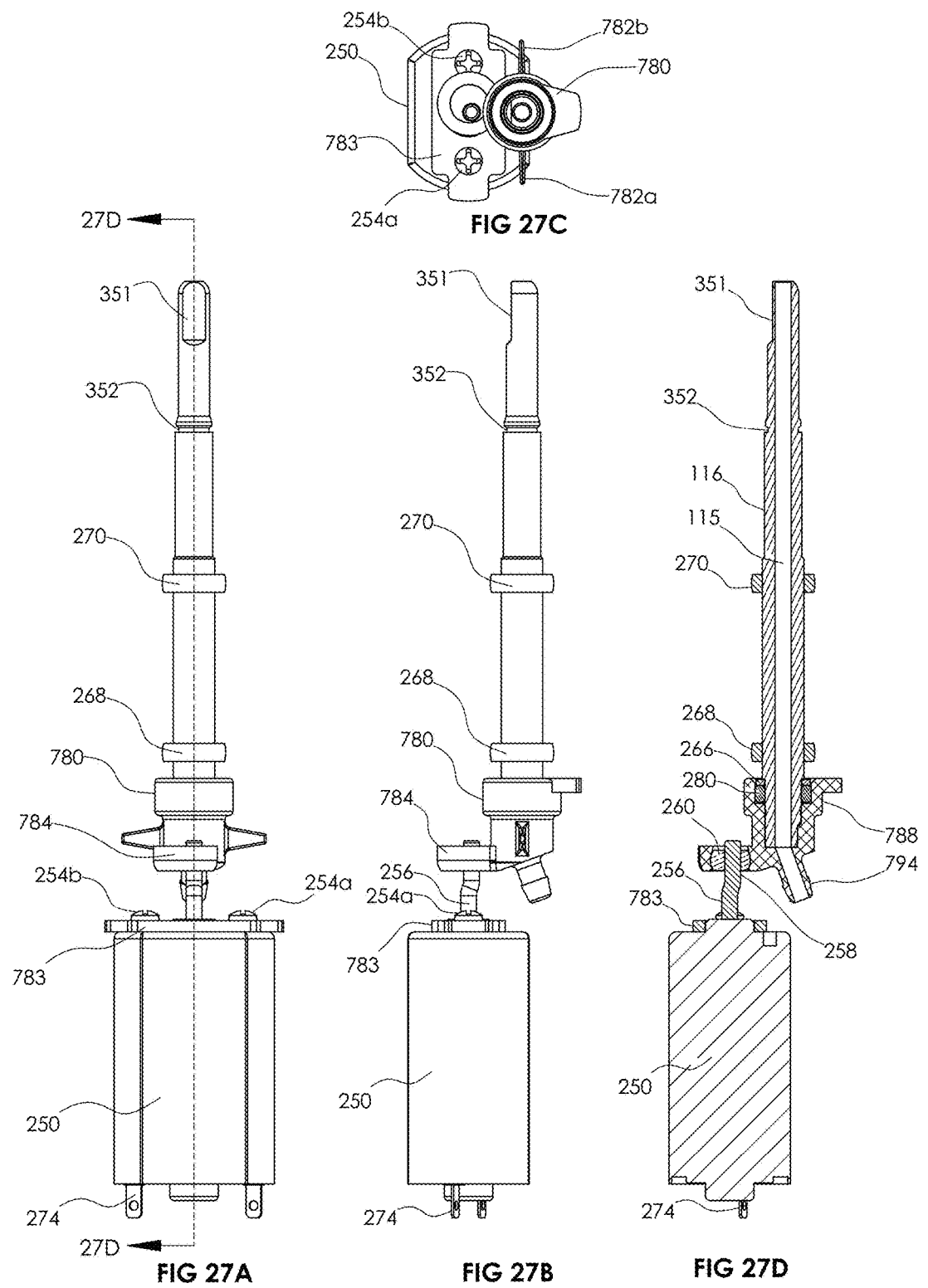

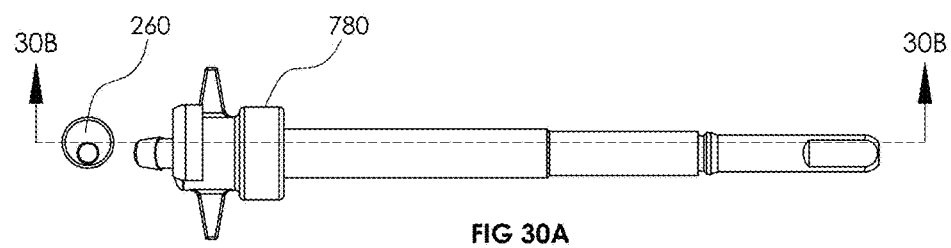
FIG 30A
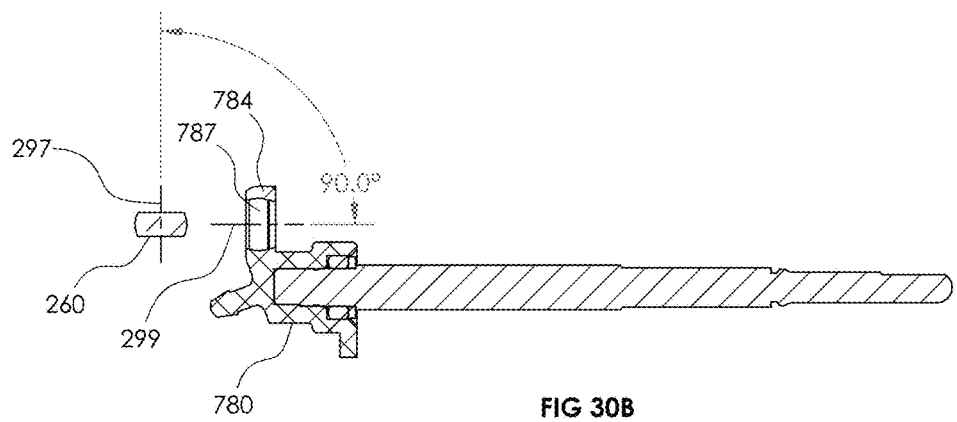
FIG 30B
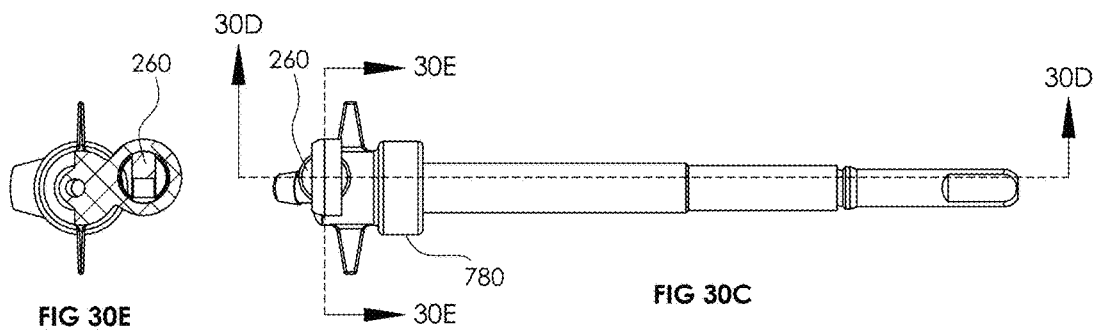
FIG 30E
FIG 30C
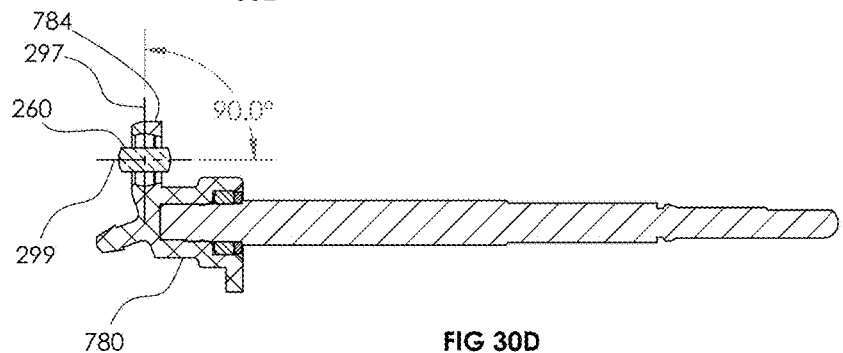
FIG 30D

ORAL CLEANSING DEVICE WITH ENERGY CONSERVATION

CROSS REFERENCE TO RELATED APPLICATIONS

The present application claims priority to U.S. Provisional Application No. 62/190,094 filed 8 Jul. 2015 entitled "Irrigating Toothbrush," the disclosure of which is hereby incorporated by reference in its entirety.

TECHNICAL FIELD

The present disclosure relates to oral health products. More specifically, the present disclosure relates to toothbrush and oral irrigating brushing devices.

BACKGROUND

The state of the art in sonic toothbrush technology centers around drive systems that create a desired oscillating toothbrush output motion by using electro-magnetic drivers and centering return springs to directly create oscillating motion. No continuous input rotation or drivers are involved in these electro-magnetic systems and such electro-magnetic systems have a relatively high production cost.

There are also currently many toothbrushes that provide oscillating output brush motion from continuously rotating input drivers. Such mechanically-driven toothbrushes typically have a reduced manufacturing cost as compared to toothbrushes employing electro-magnetic drivers. However, such rotating systems all perform the oscillating function at lower speeds.

Present oral irrigator devices are standalone units that provide a pulsing water jet stream using a dedicated, unique handle and an irrigating tip. There are some devices known as "combo" units that provide toothbrush function along with an irrigating function from a single unit. These devices essentially take an oral irrigation base unit with a handle and tip assembly, enlarge the base unit, and add a separate toothbrush handle that sits on the enlarged base. Two handles are required to provide each of irrigation and toothbrush functions.

The information included in this Background section of the specification, including any references cited herein and any description or discussion thereof, is included for technical reference purposes only and is not to be regarded subject matter by which the scope of the invention as defined in the claims is to be bound.

SUMMARY

In one embodiment, a brushing device including a motor having an eccentric drive shaft, an output shaft operably connected to the motor, and a power train assembly coupled between the eccentric drive shaft and the output shaft is disclosed. The power train assembly converts rotation of the eccentric drive shaft into an oscillating movement of the output shaft. In some embodiments, the power train assembly includes one or more conservation features that absorb and reapply energy to the output shaft while the output shaft is oscillating.

In another embodiment, a toothbrush is disclosed. The toothbrush includes a chassis assembly and an output shaft configured to connect to a brush head and extending at least in part through a portion of the chassis assembly. The toothbrush also includes a power train assembly operably connected to the output shaft and configured to oscillate the output shaft and a fluid connector operably coupled to the chassis assembly and fluidly coupled to the output shaft via the power train assembly. The fluid connector rotates 360 degrees relative to the chassis assembly when moved by a user or due to movement of the chassis assembly.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 2A is cross-section view of the irrigating toothbrush of FIG. 1A taken along line 2A-2A in FIG. 1A.

FIG. 2B is an enlarged view of the lower section of FIG. 2A.

FIG. 2C is an enlarged view of the upper section of FIG. 2A.

FIG. 4A is a rear elevation view of a chassis assembly for the irrigating toothbrush handle of FIG. 1A.

FIG. 4B is an exploded view of a chassis assembly for the irrigating toothbrush of FIG. 1A FIG. 5A is a top isometric exploded view of an end cap assembly for the irrigating toothbrush of FIG. 1A.

FIG. 5B is a bottom isometric exploded view of an end cap assembly for the irrigating toothbrush of FIG. 1A.

FIG. 5C is a top isometric view of the end cap assembly of FIG. 5A.

FIG. 5D is a rear elevation view of the end cap assembly of FIG. 5A.

FIG. 5E is a cross-section view of the end cap assembly of FIG. 5A taken along line 5D-5D in FIG. 5D.

FIG. 8A is a front elevation view of the power train assembly of FIG. 7A.

FIG. 8B is a side elevation view of the power train assembly of FIG. 7A.

FIG. 8C is a top plan view of the power train assembly of FIG. 7A.

FIG. 8D is a cross-section view of the power train assembly of FIG. 7A taken along line 8D-8D in FIG. 8A.

FIG. 9A is a rear isometric view of a rocker arm for the power train assembly of FIG. 7A.

FIG. 9B is a top plan view of the rocker arm of FIG. 9A.

FIG. 9C is a cross-section view of the rocker arm of FIG. 9A taken along line 9C-9C in FIG. 9B.

FIG. 12A is a front bottom exploded view of the brush head of FIG. 11A.

FIG. 12B is a top rear exploded view of the brush head of FIG. 11A.

FIG. 20A is an isometric view of a second example of an irrigating toothbrush.

FIG. 20B is a rear elevation view of the irrigating toothbrush of FIG. 20A.

FIG. 27A is a front elevation view of the power train assembly of FIG. 7A.

FIG. 27B is a side elevation view of the power train assembly of FIG. 7A.

FIG. 27C is a cross-section view of the power train assembly of FIG. 26A taken along line 27C-27C in FIG. 27A.

FIG. 27D is a top plan view of the power train assembly of FIG. 26A.

FIG. 30A is a front elevation view of select components of the power train assembly of FIG. 26B illustrating the orientation of the eccentric prior to installation.

FIG. 30B is a cross-section view of select components of the power train assembly of FIG. 7B taken along line 30B-30B.

FIG. 30C is a front elevation view of select components of the power train assembly of FIG. 26B illustrating the orientation of the eccentric after installation but before rotating into the operating position.

FIG. 30D is a cross-section view of select components of the power train assembly of FIG. 26B taken along line 30D-30D.

FIG. 30E is a cross-section view of select components of the power train assembly of FIG. 26B taken along line 30E-30E.

DETAILED DESCRIPTION

Figures 1A, 1B, 1C:
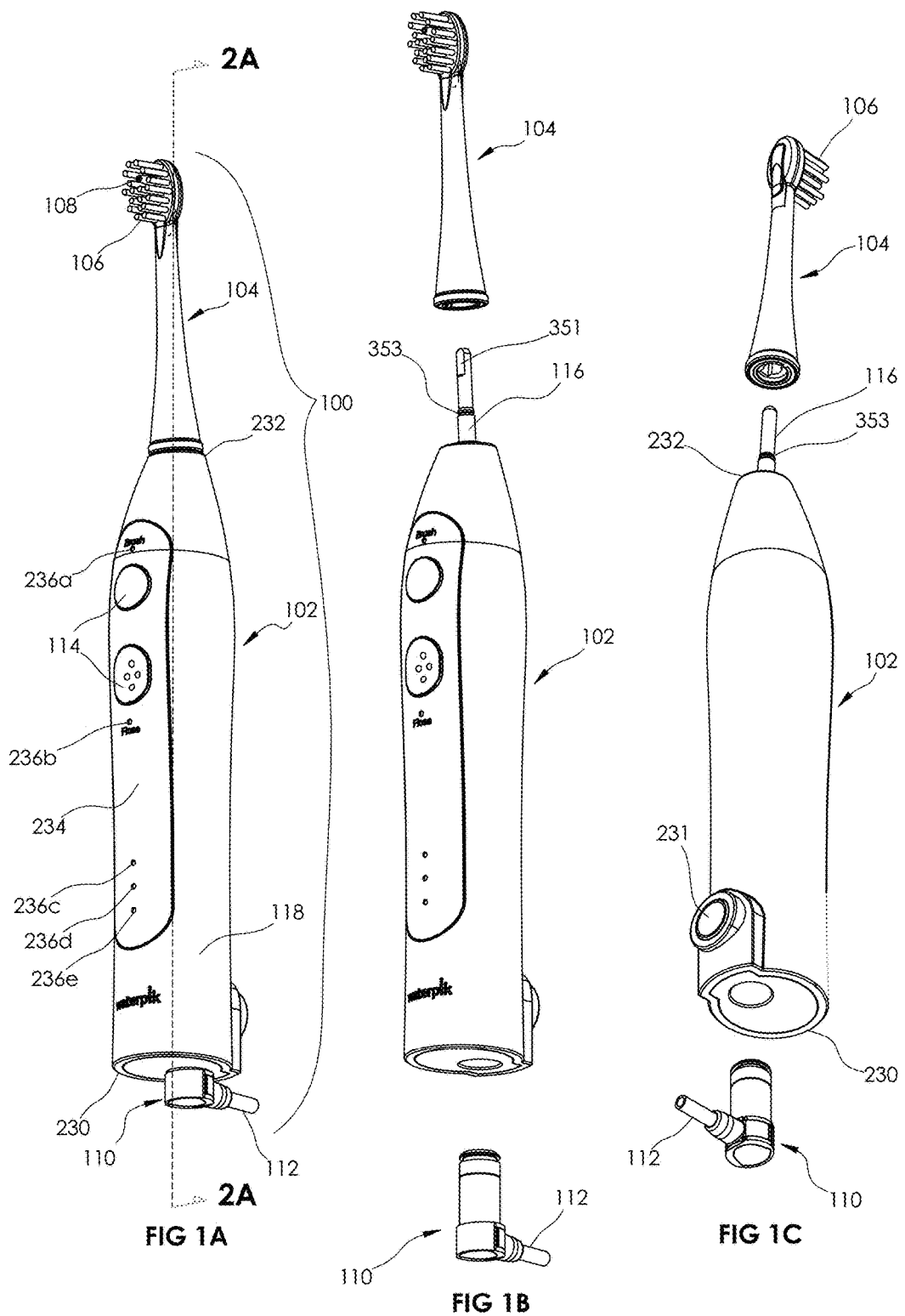
FIG. 1A is an isometric view of an irrigating toothbrush.
FIG. 1B is an isometric partially exploded view of the irrigating toothbrush of FIG. 1A.
FIG. 1C is a rear isometric partially exploded view of the irrigating toothbrush of FIG. 1A.

The present disclosure is generally related to an irrigating, electrically driven toothbrush. The brushing device provides a flow path for fluids, as well as drives an oscillating toothbrush to allow a user to irrigate his or her mouth and/or brush his or her teeth. The present system provides a power train that converts constant rotary motion into oscillating rotary motion. The power train also helps to conserve energy by including conservation features that absorb rotational momentum and return momentum in the opposite direction, which act to reduce the electrical power required to operate the motor by reversing the rotational momentum at the end of travel. The reduction in electrical power increases the number of cycles per battery charge for the system and the conservation members also act to reduce stress on the components of the power train, extending the operational life of the system.

In one embodiment, the conservation features may include spindles including compressible bumpers, such as O-rings or other rubber elements that compress to absorb momentum and expand to reapply the momentum back to the power train components.

In another embodiment, the conservation features are flexible wings that are operably connected to the power train and are secured to an inner housing or chassis. In this embodiment, the flexible wings deform as the output shaft rotates in a first direction to absorb energy and return to their original shape as the output shaft rotates in a second direction. In this manner, the flexible wings, which may function as beams or leaf springs, increase the efficiency of the system and reduce the electrical power required to drive the brush head. Specifically, the wings deflect in a first direction to absorb momentum and straight or return to their original shape to reapply momentum back to the output shaft in the second direction. As the output shaft may be oscillated, the first and second directions may be along an arc and the wings may reapply/absorb momentum at the beginning/end of the two directions or along the entire pathway. Additionally, in some embodiments, the conservation features may be positioned on opposite sides of the output shaft to act to absorb or reapply energy in opposite directions simultaneously.

In some embodiments, the conversation features may have a cross section that tapers in one or two directions as it approaches the terminal end. For example, in embodiments where the conservation features are wings, the wings may taper in thickness (e.g., along the Y axis) from a first end to a second end and may also vary in width (e.g., along the Z axis) from the first end to the second end. The variation in two directions reduces stress concentrations on the wings, as well as helps to evenly distribute the load. In these embodiments, the wings may function as beams that absorb and distribute stress and the load is evenly applied along the length.

In embodiments where the conservation features include flexible wings, a terminal end of the wings may be pinched between to chassis components or within a gap defined by an integral chassis. For example, a front chassis and a second chassis may connect together to define two opposing slots positioned on opposite sides of the output shaft. In this example, the terminal end of each wing is received and pinched within the slot. However, the slot is configured to allow the wings to move slightly within the slot. In other words, the slot provides some additional space that still pinches the wings to force the wings to deform (rather than rotate), but does not overly constrict the wings in such a manner that would cause the wings to crack or snap, as well as provides some "slop" to allow easier manufacturing and assembly. The size of the slot and the amount of gap between the edges defining the slot and the terminal end of the wings may be varied as desired and as the wing changes shape the size and configuration of the slot may vary correspondingly.

The system may also include a removable brush head that includes a fluid path that delivers fluid from a drive shaft of the power train (fluidly connected to an irrigating countertop unit) to a user's mouth via a flexible nozzle on the brush head face. The removable brush head allows different users to use the system, as each user can use a specific brush head.

The system also includes a removable water connection at the base of the toothbrush that fluidly connects the toothbrush to a reservoir and pumping source. The water connection or fluid connector may be configured to swivel 360 degrees so that the hose between the reservoir and the device moves to allow a user to use the irrigating brushing device without tangling the hose. The removable water connection also includes a valve that closes when the hose is removed, to prevent water from the irrigating countertop unit from leaking out. The removable water connection further allows the toothbrush to be used separately from the rest of the system, e.g., while a user is traveling.

In some embodiments, the irrigating brushing device may use a continuously rotating input driver (e.g., a direct current or alternating current motor) that operates a balanced power train assembly to change the continuous rotation of the input driver into a desired oscillating output motion, which drives the attached toothbrush head at a sonic speed or speeds.

Use of direct current (DC) drive motors for input drive motion may result in a lower production cost of the irrigating brushing system than the current electro-magnetic sonic toothbrush systems as well as the use of relatively inexpensive molded plastic components.

The irrigating brushing disclosed herein may provide a continuously rotating input drive system that provides oscillating, sonic-speed toothbrush output motion with an extremely low level of mechanical vibration and noise. Also, the exemplary systems disclosed herein provide a sonic toothbrush system at a reduced production cost.

Some embodiments of a toothbrush may be configured for attachment to a dental irrigating base unit. In these embodiments, the toothbrush may include a fluid inlet for connection with a fluid tube from the base unit. A fluid flow conduit is provided through the handle of the sonic toothbrush and also through a portion of the oscillation drive motion mechanism. The fluid flow conduit exits through a replaceable brush tip that carries an irrigator nozzle mounted within the bristles on the brush head. When the brush tip is attached to the output shaft of the handle, the internal water path of the brush tip is sealed with the outlet of the fluid flow conduit through the output shaft. This provides a continuous, sealed water path through the power handle up to and out of the water jet nozzle located between the toothbrush bristles.

An external, dental irrigating base system that generates a pulsed water jet is attached to an inlet port on the handle via a hose. When activated, this water jet generating system supplies a stream of pulsed or constant water which passes through the handle, through the brush tip, and exits from the nozzle within the toothbrush head bristle pattern. This water jet can be directed along the gum line to provide the water flossing effect of a standard, standalone water flosser. The base unit pumps water or other fluids from a reservoir in the base unit, through the connection hose, through the fluid pathway in the sonic toothbrush, and out the irrigator tip in the brush head to provide an irrigating brushing device in combination with the benefits of a toothbrush.

The handheld device disclosed herein provides a much more compact, efficient, and less costly "combination" toothbrush/water irrigation unit. With only one handheld device, considerable space is saved by not having to accommodate a second handle, and the space utilization can be more efficient. In addition, a single handle affords the potential for the combined system to be more economical. The detachable water source also allows the power handle to function untethered as a toothbrush for travel or when the brushing function is desired to be more portable. The single handle has the capability to control both the toothbrush function as well as the water jet function. In addition, a single, replaceable toothbrush head provides for both the brushing function as well as a directable nozzle for the water jet function without the requirement for separate, dedicated attachments to provide each of the two functions.

Turning now to the figures, an illustrative irrigating toothbrush will now be discussed in more detail. FIG. 1A illustrates an isometric view of the irrigating toothbrush. FIG. 1B illustrates an isometric view of the irrigating toothbrush with the fluid connector and brush head removed. 10 illustrates a rear isometric view of the irrigating toothbrush with the fluid connector and brush head removed. With reference to FIGS. 1A-2, the irrigating toothbrush 100 may be in the form of a handheld device and include a handle 102 with a brush assembly 104 and fluid connector 110 removably connected thereto. The removability of the brush assembly 104 allows a user to replace the brush assembly 104 as desired and allows multipole users to hygienically use the same irrigating toothbrush 100. The brush assembly 104 includes a plurality of bristles 106 and in embodiments where the device 100 includes an irrigating mode, a nozzle 108 is connected to the brush assembly 104 and is embedded within the bristles 106.

The irrigating brushing device 100 also includes one or more control buttons 114 that selectively activate and deactivate the various functions and/or modes of the irrigating toothbrush 100. The control buttons 114 may be connected to the handle 102 or any other convenient location for the user. As discussed below with reference to FIG. 16, the control buttons 114 can control the brushing functions of the irrigating brushing device 100, such as activating the oscillation of the brush assembly 104, as well as control the irrigating functions, such as the water pressure and pulse length by communicating with a base unit. The number and function control of the control buttons 114 may be varied based on the desired functionality of the system.

The handle 102 is defined by a housing 118 that extends between a base end 230 and a brush end 232. The housing 118 may be generally cylindrical in shape to ergonomically fit in the hand of a user, but it may be formed in any other desirable ergonomic shapes. The cylindrical shape may taper in the direction of the brush end 232 approximately one third the length of the housing 118 from the brush end 232. A face plate 234 may be supported on the housing 118 in a region extending about the control buttons 114 as either a separate plate or as an overmolded surface on the housing 118. The housing 118 may further expose one or more status indicators 236a-236e e.g., one or more light emitting diodes, for indicating a mode or status of operation of the irrigating brushing device 100. Exemplary modes may be low speed, high speed, or water flosser mode. Exemplary status indications may be low battery, charging, and fully charged battery.

With reference to FIGS. 1A-1C, the irrigating toothbrush 100 may include an irrigating function and in these embodiments includes a fluid connector 110 for connecting the handle 102 to a fluid source. Typically, the fluid connector 110 includes a hose 112 that is in fluid communication with a reservoir and/or pumping system for pumping fluid through the hose 112 to the nozzle 108. An example of a pumping system that may be fluidly connected to the hose 112 is shown in U.S. Pat. No. 8,641,649 entitled "Pump for Dental Water Jet," filed on Jun. 25, 2010. However, in other embodiments, the hose 112 may be connected directly to a pressurized water source, such as a faucet or J-pipe. The fluid connector 110 is removable from the handle 102 to allow the device 100 to be used without a fluid source, e.g., in brush only mode, and allow easier storage and traveling. Additionally, as will be disused in more detail below, the fluid connector 110 can be configured to rotate relative to the handle 102.

With reference to FIGS. 1C and 3, the handle 102 includes a handle housing assembly 103, a chassis assembly 105, a latch button 231, and a retainer 233. Generally, the retainer 233 retains the chassis assembly 105 inside the handle housing assembly 103. The latch button 231 actuates the fluid connector latch 156 to release the fluid connector 110.

With reference to FIGS. 2A-2C and 4A-4B, the chassis assembly 105 includes a power train assembly 130, a circuit board assembly 134, a battery assembly 136, an end cap assembly 132, a front chassis 122, a back chassis 124, a fluid tube 142, a boot seal 138, as well as various fittings, fasteners, and other connectors that assist in securing various components together. Generally, the battery assembly 136 provides power to the circuit board assembly 134, which operates the power train assembly 130 to oscillate the brush assembly 104 connected thereto, with the chassis 122, 124 providing support for the internal components of the chassis assembly 105 and the tube 142 providing a fluid pathway from the fluid connector 110 to the nozzle 108. The power train assembly 130 may also include one or more of the conservation features. The conversation features may be operably connected to or form a part of the power train assembly. Each of the various components of the irrigating toothbrush 100 will be discussed in turn below.

The end cap assembly 132 forms a bottom end of the irrigating toothbrush device 100 and fluidly connects the device 100 to the fluid connector 110, and also serves as a charging device for the battery assembly 136. FIGS. 5A and 5B are exploded views of the end cap assembly 132. FIGS. 5C and 5D illustrate various views of the end cap assembly 132. FIG. 5E is a cross-section of the end cap assembly 132 taken along line 5D-5D in FIG. 5 D. With reference to FIGS. 5A-5E, the end cap assembly 132 includes an upper end cap 148, a lower end cap 150, a charging assembly 191, a charging assembly encapsulation 155, a fluid connector latch 156, and a cap valve assembly 190.

The bobbin 152 and core 154 are configured to define an electromagnet that induces current in response to magnetic fields to charge the battery assembly 136. For example, a charge coil 153, such as copper wire, may be wrapped around the bobbin 152 and core 154 to create an induction charging assembly. Other charging assemblies may be used as well, and the induction assembly is just one example.

The upper end cap 148 is a generally cylindrical member that includes an upper cavity 172 defined on its upper end by an outer wall 194. The outer wall 194 may include an annular groove 176, as well as one or more securing apertures 180*a*, 180*b*, 180*c* defined through. A valve wall 182 extends upward from a bottom surface 192 of the upper end cap 148 to define a valve cavity 168 positioned within the upper cavity 172. For example, the valve cavity 168 may be a cylindrically shaped cavity nested within the upper cavity 172.

One or more ribs 170 may be defined along an interior surface of the valve wall 182 and may be defined as one or more longitudinal ribs extending along a length or a portion thereof of the valve wall 182. A tube connector 174 including a slot 173 defined in an outer wall extends downward from the bottom surface 192 of the upper end cap 148. The tube connector 174 may be a generally cylindrical protrusion that defines a fluid pathway therethrough. The fluid pathway of the tube connector 174 is fluidly connected to the valve cavity 168. For example, the tube connector 174 may be positioned on an opposite side of the bottom surface 192 from the valve cavity 168 and an aperture may be defined through the bottom surface 192 to fluidly connect the valve cavity 168 and tube connector 174.

The lower end cap 150 is somewhat similar to the upper end cap 148 and may be a generally cylindrically shaped member defining a fitting cavity 184 and a bobbin cavity 186. The two cavities 184, 186 are separated by a dividing wall 196. The dividing wall 196 helps to prevent fluid from the fitting cavity 184 from entering into the bobbin cavity 186 (which includes the charging components). A top end of the fitting cavity 184 may be surrounded on two sides by planar surfaces 238*a*, 238*b*, each surface 238*a*, 238*b* including a peg 200*a*, 200*b* extending upwards therefrom.

With reference to FIGS. 5C and 5D, the lower end cap 150 may also include a latch engagement wall 201 defined on an outer surface thereof. The latch engagement wall 201 may be formed as a relatively smooth surface that curves around a portion of the exterior of the lower end cap 150 defining the fitting cavity 184. Beneath the latch engagement wall 201, two arm compartments 202 are defined by outwardly extending flanges 199*a*, 199*b* that are separated by a portion 198 of the outer wall.

With reference again to FIG. 5A, the latch 156 is used to selectively secure the fluid connector 110 to the end cap assembly 132. For example, with brief reference to FIGS. 2B and 3, a latch button 231 accessible on the outside of the housing 118 allows a user to activate the latch 156. With reference again to FIG. 5A-5C, the latch 156 includes two latch arms 166*a*, 166*b* connected to a latch body 240. The terminal ends of the latch arms 166*a*, 166*b* may include an aperture defined through a center of the ends of the arms 166*a*, 166*b* and a beveled shaped engagement end. The latch arms 166*a*, 166*b* include a wedge shaped leaf spring 242*a*, 242*b* extending inwardly in opposing directions section, with a first leaf spring 242*a* being positioned closer to a top end of the latch body 240 and the second leaf spring 242*b* positioned closer to a bottom end of the lateral body. The leaf springs 242*a*, 242*b* provide flexibility for the latch 156 and are configured to flex. In one configuration, the tail sections 242*a*, 242*b* curve away from the latch body 240 inward between the latch arms 166*a*, 166*b* to interface with the latch engagement wall 201.

With reference to FIGS. 5A, 5B and 5E, the valve assembly 190 for the end cap assembly 132 includes a valve cap 162, a poppet spring 160, and a poppet 158. The valve cap 162 includes a connection nipple 164 formed on a top surface towards a first end of the cap 162 and a spring post 244 formed on a bottom surface towards a second end of the cap 162, such that the nipple 164 and the spring post 244 are offset from one another and formed on opposite surfaces of the cap 162. The nipple 164 is hollow and defines a fluid pathway therethrough, whereas the spring post 244 may be solid. The spring 160 wraps around the spring post 244 and engages with a top end of the poppet 158.

Figure 6A:
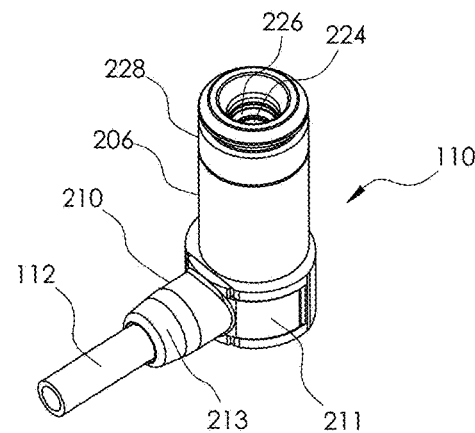
FIG. 6A is a top isometric view of a removable fluid connector for the irrigating toothbrush of FIG. 1.
Figure 6B:
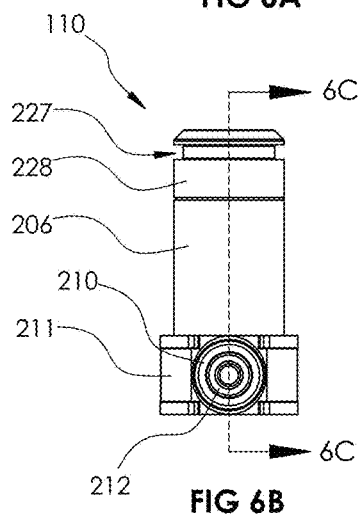
FIG. 6B is a rear elevation view of the removable fluid connector of FIG. 6A.
Figure 6C:
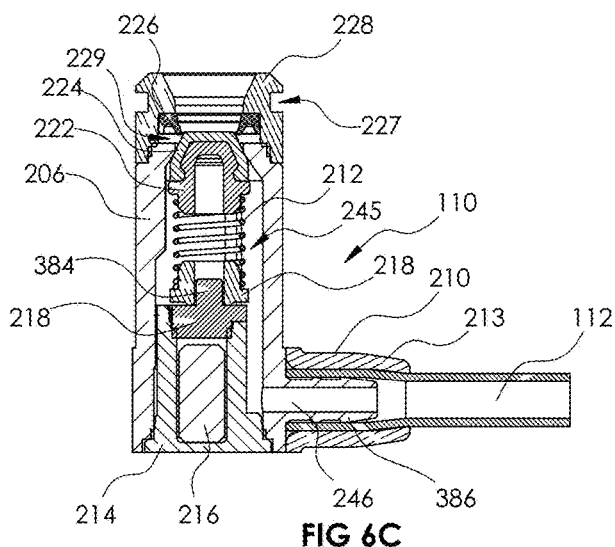
FIG. 6C is a cross-section view of the fluid connector of FIG. 6A taken along line 6C-6C in FIG. 6B.
Figure 6D:
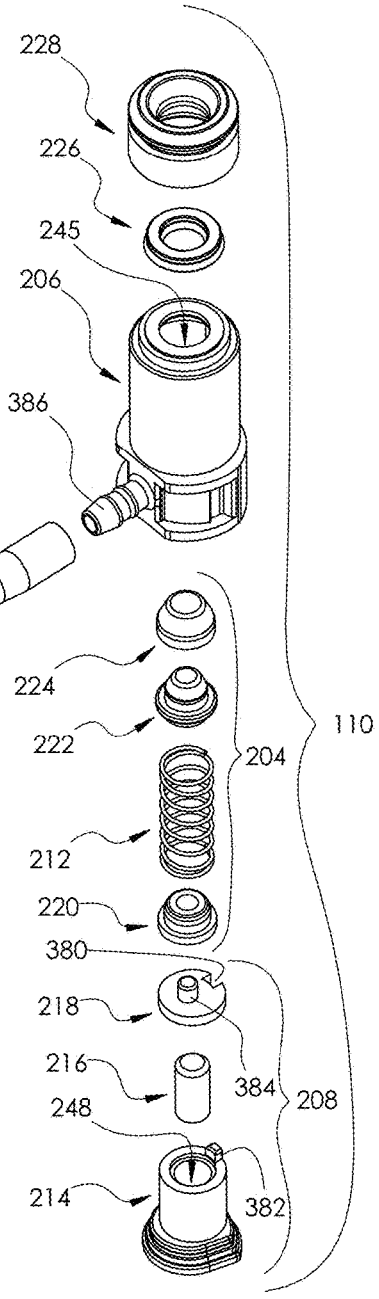
FIG. 6D is an exploded view of the fluid connector of FIG. 6A.
Figures 7A, 7B:
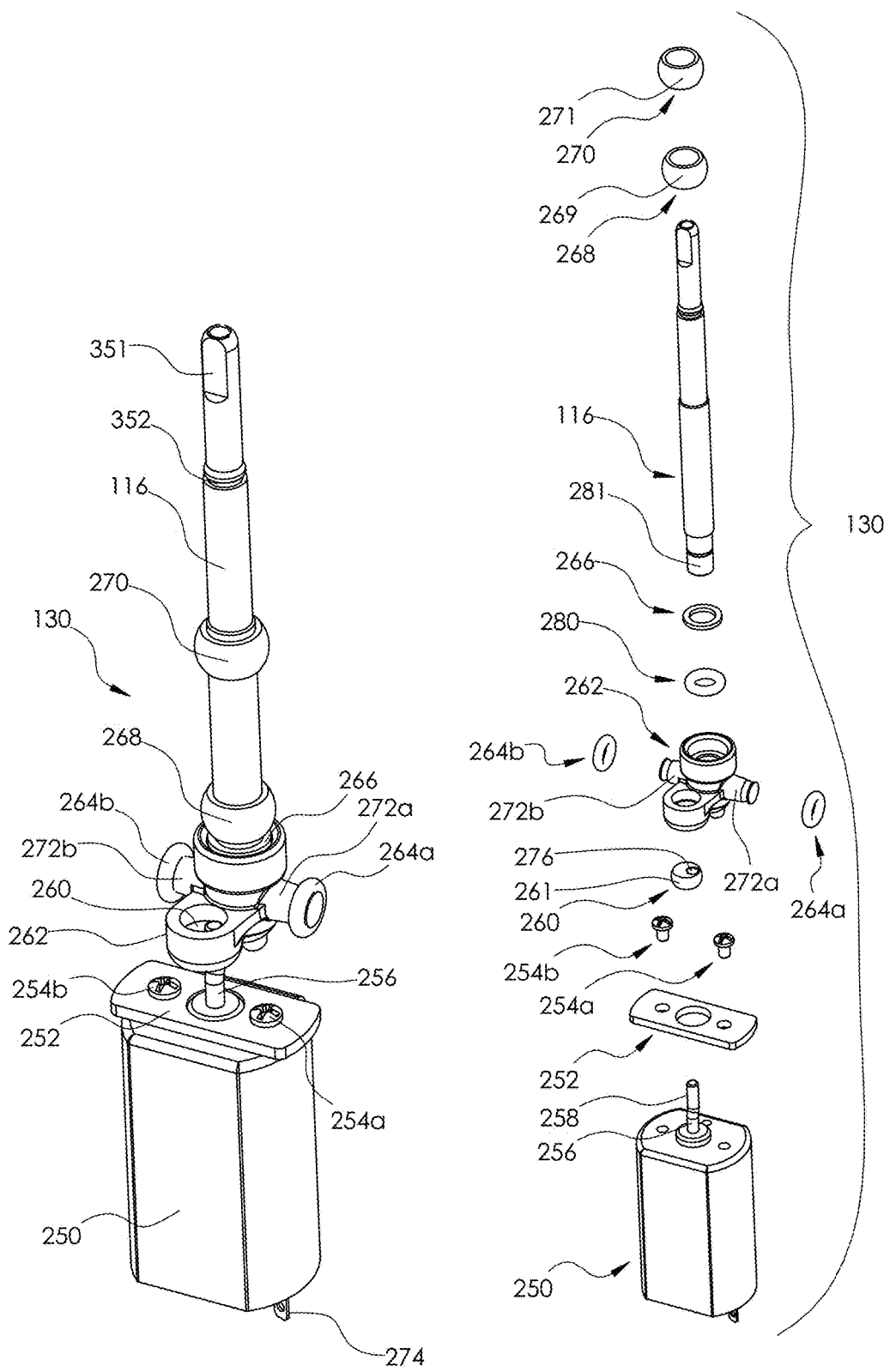
FIG. 7A is a top isometric view of a power train assembly of the irrigating toothbrush of FIG. 1A.
FIG. 7B is a top isometric exploded view of a power train assembly of the irrigating toothbrush of FIG. 1A.
Figure 10A:
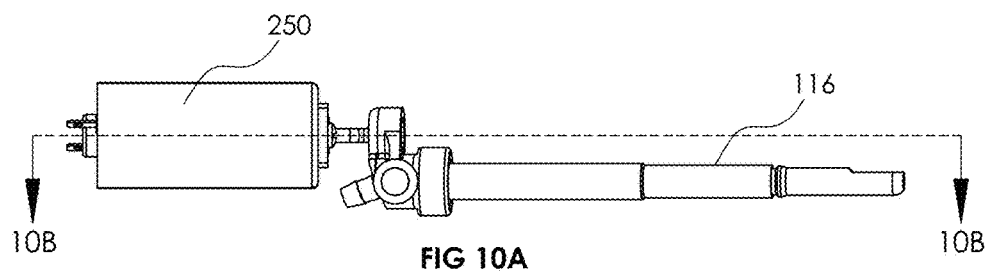
FIG. 10A is a side view of the power train assembly of FIG. 7A illustrating a misaligned output shaft axis in the front plane.
Figure 10B:
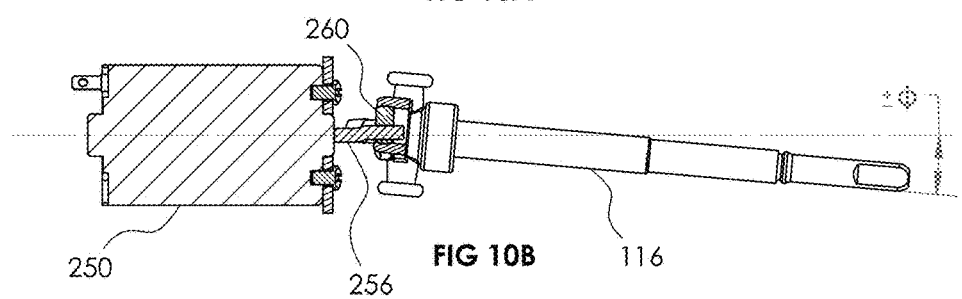
FIG. 10B is a cross-section view of the power train assembly of FIG. 7A illustrating a misaligned output shaft axis in the front plane taken along line 10B-10B in FIG. 10A.
Figure 10C:
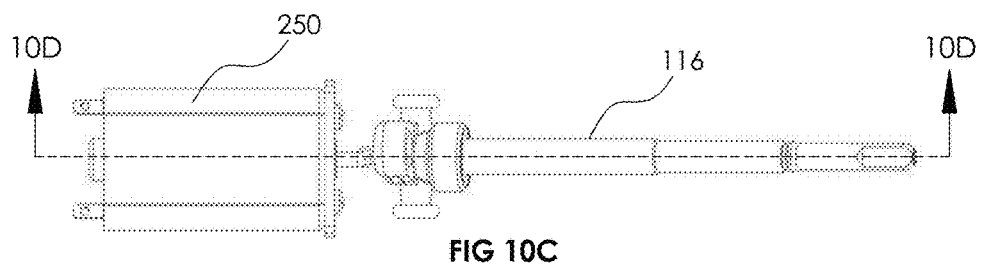
FIG. 10C is a front view of the power train assembly of FIG. 7A illustrating a misaligned output shaft axis in the side plane.
Figure 10D:
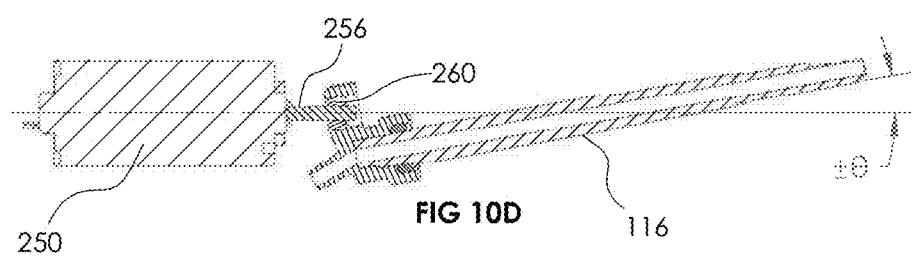
FIG. 10D is a cross-section view of the power train assembly of FIG. 7A illustrating a misaligned output shaft axis in the side plane taken along line 10D-10D in FIG. 10C.
Figure 10E:
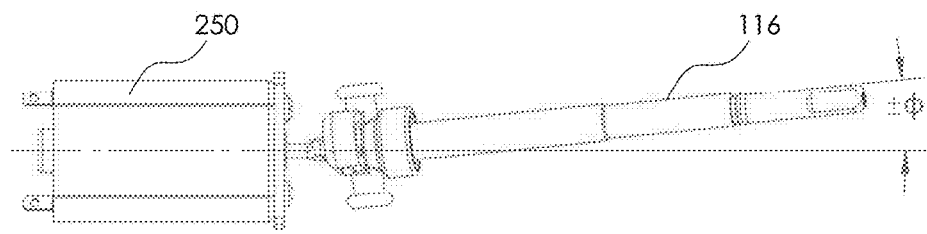
FIG. 10E is a front view of the power train assembly of FIG. 7A illustrating a misaligned output shaft axis in both the front and the side plane.
Figure 10F:
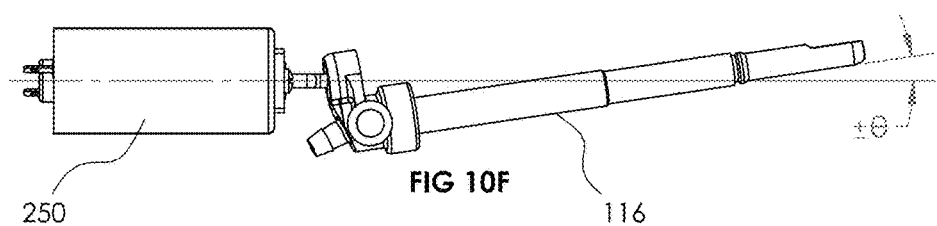
FIG. 10F is a side view of the power train assembly of FIG. 7A illustrating a misaligned output shaft axis in both the front and the side plane.
Figure 11A:
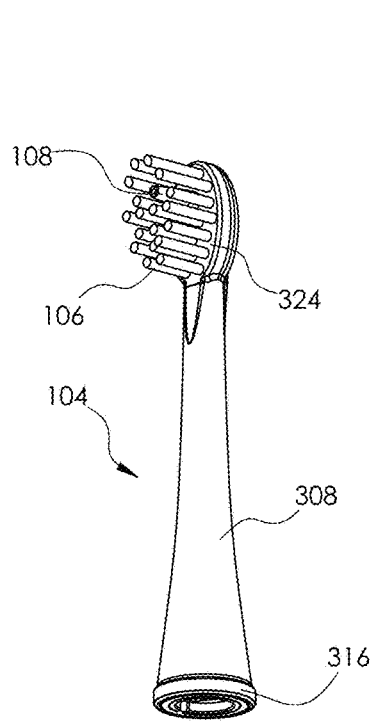
FIG. 11A is a front bottom isometric view of a brush head for the irrigating toothbrush of FIG. 1A.
Figure 11B:
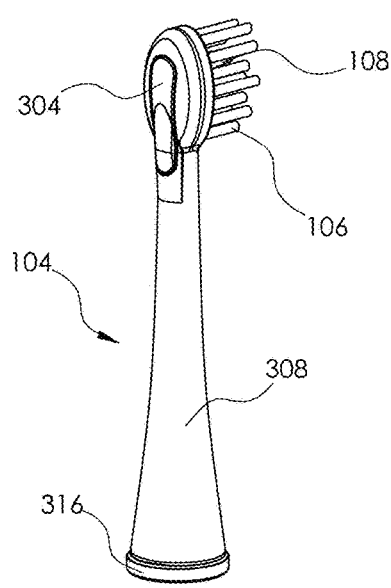
FIG. 11B is a top rear isometric view of the brush head of FIG. 11A.
Figure 11D:
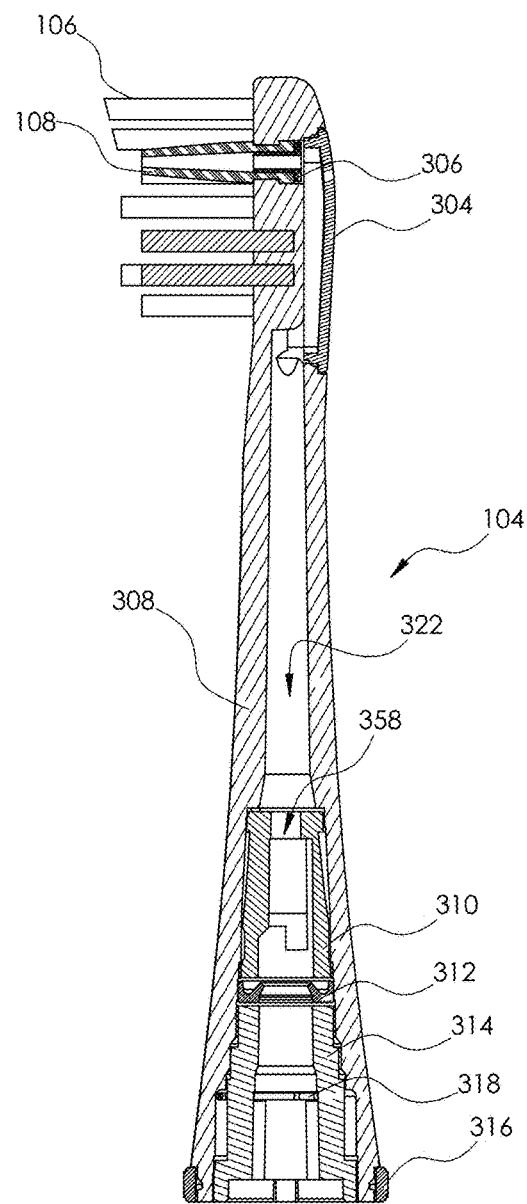
FIG. 11D is a cross-section view of the brush head of FIG. 11A taken along line 11D-11D in FIG. 11O.
Figure 11C:
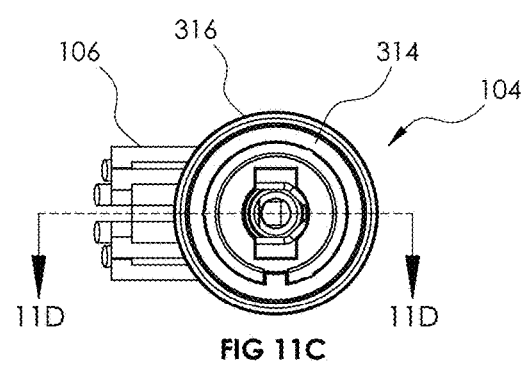
FIG. 11C is a bottom plan view of the brush head of FIG. 11A.

The fluid connector 110 will now be discussed in more detail. FIGS. 6A-6C illustrate various views of the fluid connector 110. FIG. 6D is an exploded view of the fluid connector 110. The fluid connector 110 fluidly connects the tube 142 with the hose 112 fluidly connected to a fluid source (e.g., dental irrigator base unit with a reservoir, etc.). With reference to FIGS. 6A-6D, the fluid connector 110 includes a fitting 206, a hose 112, a tube collar 210, a sealing member 226, a fitting top cap 228, a bottom cap assembly 208, and a valve assembly 204. The bottom cap assembly includes a bottom cap 214, a pin 216, and a retainer 218. The valve assembly 204 includes a spring bearing 220, a spring 212, a poppet 222, and a poppet cap 224.

The pin 216 is used to provide a magnetic attraction to a base unit to support the fluid connector 110 on a base unit, described below. The pin 216 may be any type of material having magnetic properties, including, for example, steel, iron, nickel, or the like.

The fitting 206 defines a housing that houses and retains the valve assembly 204 within a cavity 245 defined therein. The fitting 206 may be L-shaped defining a fluid passageway 246 there through. The fitting bottom cap assembly 208 is fitted within a bottom end of the fluid pathway 245 to seal the bottom end of the fitting 206. The bottom cap assembly 208 may be sonically welded or otherwise adhered to the fitting 206 to provide a fluid tight seal. The bottom cap 214 may include a pin cavity 248 defined therein that receives the pin 216. The retainer 218 may be sonically welded or otherwise adhered to the bottom cap 214 to provide a fluid tight seal for the pin cavity 248. The fitting top cap 228 includes an annular groove 227 within an outer wall thereof and connects to a top end of the fitting 206. The top cap 228 may also define an internal annular recess 229 in which the sealing member 226 (e.g., a U-cup) seats. The tube collar 210 may include a U-shaped clip bracket 211 and a tube clamp 213 that fit over a hose 112 and around an outer surface of the fitting 206 to secure the hose 112 to the fitting 206.

The power train assembly 130 will now be discussed in more detail. FIGS. 7A-8D illustrate various views of the power train 130. The power train assembly 130 powers the output shaft 116 and defines the output motion of the brush assembly 104. The power train 130 includes a motor 250, a mount plate 252, an eccentric 260, a rocker arm 262, bumpers 264a, 264b, the output shaft 116, and one or more sleeve bearings 268, 270. In this embodiment, the rocker arm 262 and/or bumpers 264a, 264 b may together define the conservation features. However, as discussed in more detail below, in other embodiments, the rocker arm 262 alone or in combination with other elements may define the conservation features for the device. Additionally, the power train 130 may include one or more fasteners 254a, 254b an O-ring seal 280, and a seal retainer 266.

The motor 250 may be substantially any type of device that converts electrical energy into mechanical energy. In some embodiments, the motor 250 may be a direct current motor. The motor 250 includes a drive shaft 256 with an eccentric portion 258 integrally formed therewith. In other words, a single drive shaft 256 includes two separate longitudinal axes, a first axis aligned with approximately a central region of the motor 250 and a second axis offset from the first axis.

Figure 18B:
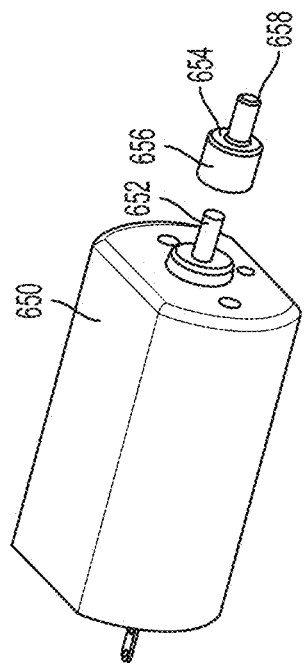
FIG. 18B is an exploded view of the motor and eccentric assembly of FIG. 18A.
Figure 19B:
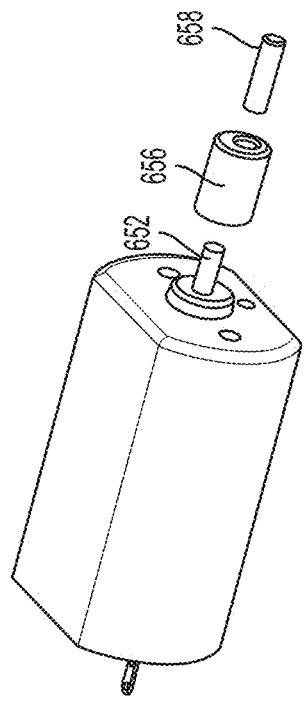
FIG. 19B is an exploded view of the motor and eccentric assembly of FIG. 19A.
Figure 18A:
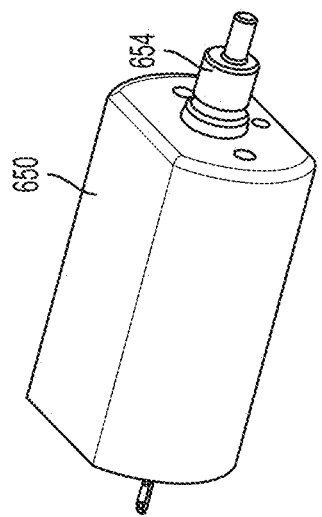
FIG. 18A is a top isometric view of a motor and eccentric assembly including a one-piece eccentric component.
Figure 19A:
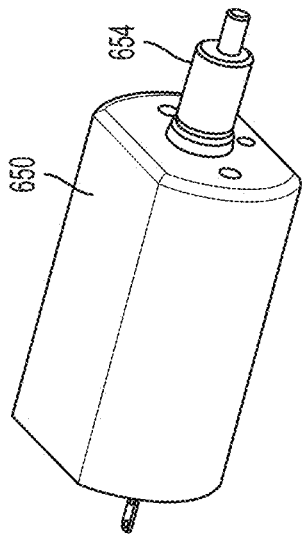
FIG. 19A is a top isometric view of a motor and eccentric assembly including a two-piece eccentric component.

It should be noted that in other examples, the eccentric portion 258 may be formed in other manners. For example, FIGS. 18A and 18B illustrate various views of a motor 650 including a drive shaft 652 with an eccentric component connected thereto, rather than being formed integrally with the drive shaft. With reference to FIGS. 18A and 18B, in this example, the eccentric 654 includes a base portion 656 and a post 658 extending from a top surface of the base 656. The eccentric 654 connects to the drive shaft 652 and the post 658 forms an output shaft for the motor 650 and is eccentric relative to an output axis of the motor 650. As another example, FIGS. 19A and 19B illustrate an example of a motor 650 including a two-piece eccentric 654. In this example, the base portion 656' is received around the drive shaft 652 and the post 658' is received into an aperture or cavity defined in the base portion 656 and extends out from the base portion 656 to form the output shaft of the motor 650. However, in embodiments, where the motor includes an integral drive shaft with a bent or eccentric portion, the number of components for the device can be reduced, reducing manufacturing costs, reducing complexity of the product, and increasing reliability.

With reference again to FIGS. 7A-8D, the eccentric 260 of the power train assembly 130 connects to the drive shaft 256 and includes a drive shaft aperture 276 for receiving the drive shaft 256. The eccentric 260 may be a disc shaped member and the drive shaft aperture 276 is offset from the center of the eccentric 260. In one example, the drive shaft aperture 276 is adjacent an outer perimeter edge of the eccentric 260. The eccentric may have a spherical outer surface 261.

The sleeve bearings 268, 270 are configured to be received around a portion of the output shaft 116. The sleeve bearings 268, 270 help to cushion the output shaft 116 and reduce friction with the chassis 122, 124 as the output shaft 116 oscillates. The sleeve bearings 268, 270 may have a spherical outer mounting surface 269, 271 that is configured to be received within a corresponding mounting feature within the chassis. Although the bearings 268, 270 are discussed as sleeve bearings, in other embodiments other types of cushioning elements can be used, such as ball bearings.

The rocker arm 262 defines the oscillating movement of the output shaft 116 and helps to conserve energy for the power train and the brush. FIGS. 9A-9B illustrate various views of the rocker arm 262. With reference to FIGS. 9A-9B, the rocker arm 262 includes a main body 290 including two spindles 272a, 272b or arms extending laterally outward from a right side and a left side, respectively, of the main body 290. The two spindles 272a, 272b are axially aligned with each other and each may include an annular groove 292a, 292b within an outer surface on a terminal end thereof for receiving a bumper element 264a, 264b, which may be a compressible component, such as an O-ring or other rubber component. In some embodiments, the spindles 272a, 272b may be flexible and may engage a sidewall or interior surface of the housing or chassis to conserve energy. In other embodiments, the spindles 227a, 272b may include an additional deformable member, such as a rubber O-ring that deforms against the interior surface to absorb and reapply energy to the rocker arm 262. Another example of the rocker arm and spindles is shown in FIGS. 26A-26D.

The rocker arm 262 also includes a fluid connector 294 extending downward from the main body 290. The fluid connector 294 is configured to connect to a fluid tube and may include a male or female connector, and in one embodiment includes a barb as shown in FIG. 9A. Depending on the configuration of the housing and size of the irrigating toothbrush 100, the fluid connector 294 may be arranged at various angles relative to the main body 290. For example, as shown in FIG. 9A, the fluid connector 294 may extend downward at an angle relative to the main body 290, rather than being perpendicularly oriented relative to the spindles 272a, 272b. However, in other embodiments, the fluid connector 294 can be otherwise arranged.

With continued reference to FIGS. 9A-9B, a cylindrical outer wall 300 extends upwards from the top end of the main body 290. The outer wall 300 defines a shaft cavity 288 formed on the top end of the main body 290. The shaft cavity 288 is in fluid communication with the fluid connector 294 via a fluid passage defined through the main body 290. The diameter of the shaft cavity 288 may be varied to assist in retaining the output shaft 116 and other components. For example, the rocker arm 262 may include a locking feature 296 extending into the shaft cavity 288 from an interior surface and optionally an annular shelf 298 extending into the shaft cavity 288 from an interior surface arranged closer to the top end of the outer wall 300 from the locking feature 296. The shaft cavity 288 includes interior surfaces that contact the seal 280. The seal retainer 266 helps to secure the seal 280 within the shaft cavity 288 and provides support on the outside portion of the seal 280. In other configurations the seal retainer 266 can be integrated into the output shaft 116 in a one-piece design. In some embodiments, the rocker arm 262 can be overmolded onto the output shaft 116 to form a watertight seal without additional seal elements. Other features and configurations are also envisioned.

The rocker arm 262 also includes a cam follower 284 that extends from a front surface of the main body 290. The cam follower 284 is a hollow bracket structure that defines an eccentric cavity 286. With reference to FIGS. 7B and 9A-9C, the eccentric cavity 286 may have a socket 287 to receive the outer surface 261 of the eccentric 260. In embodiments where the outer surface of the eccentric 260 is spherically shaped, the socket 287 may be correspondingly spherically shaped. The socket 287 of the cam follower 284 allows the axis of the eccentric 260 to rotate such that the axis of the motor drive shaft 256 and the axis of the output shaft 116 can have an angular misalignment in one of two planes or both planes simultaneously as shown in FIGS. 10A-10F. Due to the angular misalignment allowed between the axis of the motor drive shaft 256 and the axis of the output shaft 116, when the handle 102 experiences an impact event that causes the chassis 122, 124 to flex, the motor 250 can move with respect to the output shaft 116, allowing the power train assembly 130 to be less susceptible to damage. In addition, less precise motor mounting tolerances can be used because parallel mounting of the motor drive shaft 256 and the output shaft 116 is not required. Further, the position of the motor 250 can be angled in the handle 102 to optimize space for other components, while maintaining the desired orientation of the output shaft 116.

Various tips can be used with the irrigating toothbrush device 100. One example of a brush tip that can be used with the irrigating toothbrush device is disclosed in U.S. Publication No. 2014/0259474 entitled "Mechanically-Driven, Sonic Toothbrush and Water Flosser" filed Mar. 17, 2014, which is incorporated by reference herein in its entirety. Another example is shown in FIGS. 11A-12B, which illustrate various views of one example of a tip. With reference to FIGS. 11A-12B, the brush assembly 104 includes a tip shaft 308 with a brush head 320. The tip shaft 308 defines a tip fluid passage 322 therethrough to the brush head 320. The brush head 320 defines a bristle base 324 composed of a plurality of recesses into which a plurality of bristle tufts 106 may be inserted and secured in place. In addition, the brush head 320 defines a nozzle aperture 107 that opens in the bristle base 324 in an area surrounded by bristle tufts 106. A trim ring 316 may be attached to the base 340 of the tip shaft 308 to allow for multiple users of the device 100 to easily identify their personal brush assembly 104 for attachment to the handle 102. For example, the trim ring 316 may be various colors to identify different user's brushes. The base 340 of the tip shaft 308 may define a recess with a retention groove 326. The inner wall of the colored trim ring 316 may define a number of retention detents 328 that may snap into the retention groove 326 to retain the colored trim ring 316 around the base of the brush assembly 104.

An elastomeric jet nozzle 108 is positioned within the nozzle aperture 107 and extends normal to the bristle base 324 approximately the same distance as the bristle tufts 106. The nozzle 108 defines a fluid lumen, is generally conical, and tapers in diameter from its base to its tip. A cavity 330 is formed in the back of the brush head 320 to provide access to the nozzle aperture and a fluid flow connection between the nozzle aperture and the tip fluid passage 322. The cavity 330 may be enclosed by a brush head plug 304 that snaps into the sidewalls defining the cavity 330 and is ultrasonically welded or otherwise adhered to provide a fluid-tight seal in the brush head 320.

A cylindrical recessed band 334 is formed in a sidewall of the nozzle 108 adjacent the base, which thus appears as a raised band 336. The outer diameter of the recessed band 334 is generally congruent with the diameter of the nozzle aperture while the outer diameter of the recessed band 334 is larger than the diameter of the nozzle aperture. When the nozzle 108 is inserted into the nozzle aperture from the cavity 330 in the rear of the brush head 320, the recessed band 334 fits snugly within the nozzle aperture 107 and the raised band 336 abuts the back of the bristle base 324, preventing the nozzle 108 from being pushed through the nozzle aperture when under pressure. In addition, a nozzle insert 306, e.g., a brass tube with a rear flange, may be inserted into the base of the nozzle 108 to prevent the nozzle 108 from bending or collapsing under high water pressure and contact with teeth and thereby dislodging from the nozzle aperture.

A retainer 310 may be inserted into and permanently affixed within the tip fluid passage 322 from the base end 340 of the tip shaft 308. In the exemplary implementation shown, the retainer 310 may be generally formed as a frustum with open sidewalls. A top ring 350 is joined to a larger diameter bottom ring 352 by an alignment rib 354 on one side and a support rib 356 laterally opposed thereto. The top ring 350 defines an outlet aperture 358.

A sealing element 312, such as a U-cup, may be inserted into the tip fluid passage 322 of the tip shaft 308 after the retainer 310 and may be held in place against the retainer 310 by an end cap 314. In this exemplary implementation, the end cap 314 is formed as a series of stacked cylinders with decreasing diameters as they extend toward the brush head 320. The end cap 314 defines a lumen 360 through which the output shaft 116 passes when the brush assembly 104 is placed on the handle 102. The retainer posts 362a-362d extend outward from the sidewall of the bottom end of the end cap 314. When the end cap 314 is inserted into the lumen 338 of the tip shaft 308, the base end 340 deflects and deforms to allow installation of the retainer posts 362a-362d of the end cap 314. The alignment slot 364 of the end cap 314 nests onto the alignment rib 332 inside the lumen 338 of the tip shaft 308 ensuring alignment of the retainer posts 362a-362d of the end cap 314 to the retainer apertures 361a-361d of the tip shaft 308.

Clip slots 366a-366d are also formed in the sidewall of the end cap 314. The clip slots 366a-366d extend transversely through the end cap 314. The clip slots 366a-366d are configured to retain a spring retainer clip 318 therein to secure the output shaft 116 to the brush assembly 104. The spring retainer clip 318 may be formed from a piece of stiff wire to have a pair of clip arms 368a, 368b that oppose each other and are joined at a clip arch 370. The free ends of the clip arms 368a, 368b each form a reverse curve that opens away from the other. When the retainer clip 318 is installed in the clip slots 366a-366d, the clip arch 370 extends outside the end cap 314, the middle sections of the clip arms 368a, 368b are retained within the clip slots 366a-366d in the front wall, and the free ends of the clip arms 368a, 368b are exposed outside of the end cap 314.

Assembly of the Irrigating and Brushing Device

Assembly of the irrigating toothbrush device 100 will now be discussed. It should be noted that although the below discussion outlines examples of an ordering assembly, many other assembly orders and manufacturing techniques and ordering are anticipated and the below discussion is meant as illustrative only.

With reference to FIGS. 6A-6D for assembly of the removable fluid connector 110, the bottom cap assembly 208 is assembled by inserting the steel pin 216 into the pin cavity 248 of the fitting bottom cap 214. The retainer 218 is then positioned on the top end of the fitting bottom cap 214 and secured into place when the slot 380 fits around the nub 382 on the top end of the fitting bottom cap 214. The valve assembly 204 is assembled by pressing the poppet cap 224 onto the top end of the poppet 222. The top end of the spring 212 is then sleeved over a portion of the lower section of the poppet 222. The lower section of the spring 212 is then sleeved over a portion of the spring bearing 220 such that the spring spans between the bearing 220 and the poppet 222. The spring bearing 220 is seated on top of the retainer 218 with the post 384 of the retainer 218 extending into a cavity defined by the spring bearing 220 to secure the spring bearing 220 to the retainer 218. The valve assembly 204 and the bottom cap assembly 208 are then inserted within the cavity 245 of the fitting 206, and the bottom cap 214 is secured to the fitting 206 by a sonic weld or by another bonding method to form a fluid tight seal. The sealing element 226 is received within the fitting top cap 228 and the fitting top cap 228 is secured to the top end of the fitting 206 by a sonic weld or by another bonding method to the top end of the fitting 206 to form a fluid tight seal. The hose 112 is received around the barb 386 extending from a sidewall of the fitting 206 and the tube collar 210 is slipped over the hose 112 so that a friction fit against the hose 112 in the location of the tube clamp 213 is formed. The arms of the U-shaped clip bracket 211 snap around an outer surface of the fitting 206, such as within a predefined groove or recession around the outer surface of the fitting 206.

Assembly of the end cap assembly 132 will now be discussed. With reference to FIGS. 5A-5E, conductive wiring is wrapped around the bobbin 152 multiple turns to form a conductive charge coil 153, and then the core 154 is positioned on the bobbin 152 with a middle section of the core 154 being positioned between the two upwardly extending prongs of the bobbin 152 and the outer sections of the core 154 being positioned outside two of the outer edges of the bobbin 152 such that the conductive charge coil 153 that wraps around an outer surface of the bobbin 152 will extend between the two outer sections of the core 154. The charging assembly 191 is then received in the bobbin cavity 186 of the lower end cap 150 and secured therein by submersing or encapsulating the charging assembly 191 with an adhesive or potting material 155 to form a waterproof encapsulation. A non-encapsulating attachment method using a mechanical fastener or an adhesive bond may also be used; however the encapsulation method provides better protection for the components in the charging assembly 191 if the handle 102 experiences an impact event or a water leak.

With continued reference to FIGS. 5A-5E, the latch 156 is connected to the lower end cap 150 with apertures in each of the latch arms 166a, 166b being received around pegs 200a, 200b of the planar surfaces 238a, 238b and the latch body 240 and the leaf springs 242a, 242b interfacing against the outer surface of the latch engagement wall 201.

After the latch 156 is connected to the lower end cap 150, the upper end cap 148 is connected to the lower end cap 150 by a sonic weld or by another bonding method to form a fluid tight seal between the bobbin cavity 186 and the upper end cap 148. In particular, the tube connector 174 is aligned with the fitting cavity 184 of the lower end cap 150, and the latch holes 203a, 203b are positioned over the pegs 200a, 200b of the lower end cap 150. In this manner, the upper end cap 148 seats on the top end of the lower end cap 150. Before or after the upper end cap 148 is connected to the lower end cap 150, the valve assembly 190 is inserted into the upper end cap 148. Specifically, the poppet 158 is positioned in the valve cavity 168 of the upper end cap 148 and the spring 160 is seated on the top end of the poppet 158 between the one or more ribs 170. The cap 162 is then connected to the spring 160 with the spring post 244 being received into the center of the spring 160, such that the spring 160 wraps around the spring post 244. The cap 162 seats on the top edge of the valve wall 182 by a sonic weld or by another bonding method to form a fluid tight seal.

The assembled removable fluid connector 110 and the end cap assembly 132 may be connected together to fluidly connect the irrigating toothbrush 100 with the base unit, as described below. FIGS. 13A-14D illustrate various views of the fluid connector 110 connected to the end cap assembly 132. With reference to FIGS. 14C and 14D, the top end of the removable fluid connector 110, specifically, the fitting top cap 228 and top end of the fitting 206 are inserted into the fitting cavity 184 of the lower end cap 150. Before the fluid connector 110 is inserted into the end cap assembly 132 and pressurized fluid flows into the end cap assembly, the poppet 158 seals against the outlet of the tube connector 174 to prevent fluid remaining within the device 100 from a prior use from leaking out of the device 100 via the tube connector 174.

As the fluid connector 110 is inserted into the end cap assembly, the tube connector 174 of the upper end cap 148 is inserted into the center of the fitting top cap 228 and extends into the fitting 206 to press against the poppet cap 224. The force of the tube connector 174 compresses the spring 212 moving the poppet cap 224 and poppet 222 downward towards the spring bearing 220 and retainer 218. In this configuration, the poppet cap 224 and poppet 222 are pressed downward away from the top end of the fitting 206 to allow fluid to flow around the poppet cap 224 and poppet 222 through the slot 173 defined in the outer wall of the tube connector 174 and into the internal flow path in the tube connector 174.

Figure 13A:
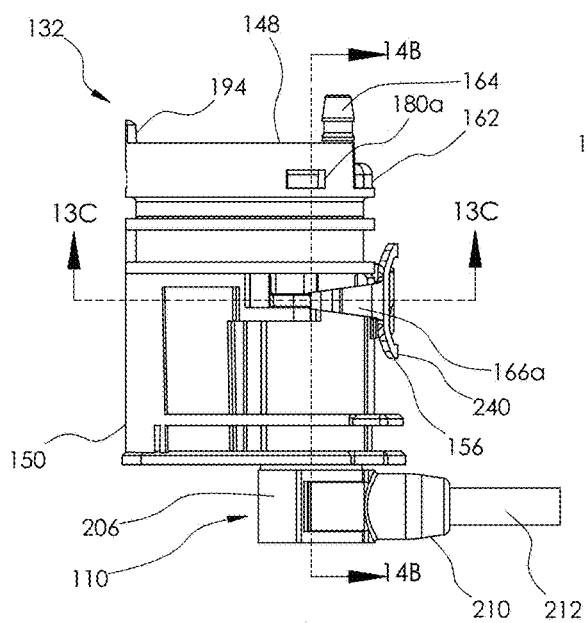
FIG. 13A is a side elevation view of the fluid connector connected to the end cap assembly of the irrigating toothbrush of FIG. 1A.
Figure 13B:
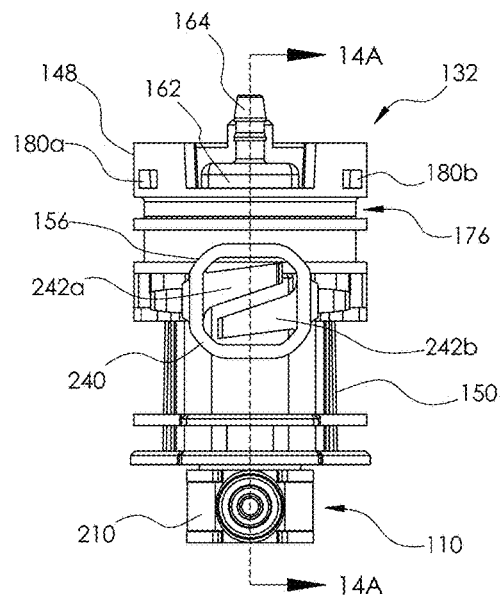
FIG. 13B is a rear elevation view of the fluid connector connected to the end cap assembly of FIG. 13A.
Figure 13C:
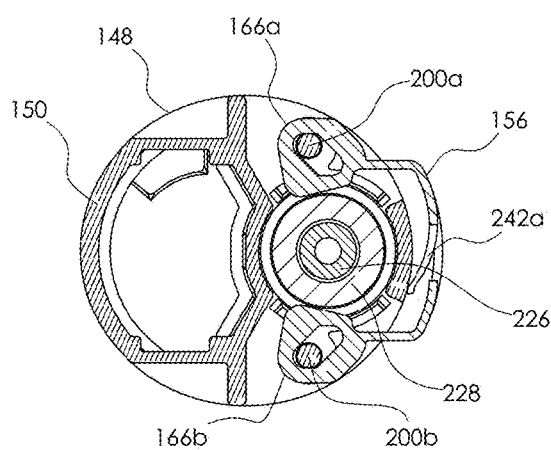
FIG. 13C is a cross-section view of the fluid connector connected to the end cap assembly of FIG. 13A taken along line 13C-13C in FIG. 13A illustrating the fluid connector latch in the latched position.
Figure 13D:
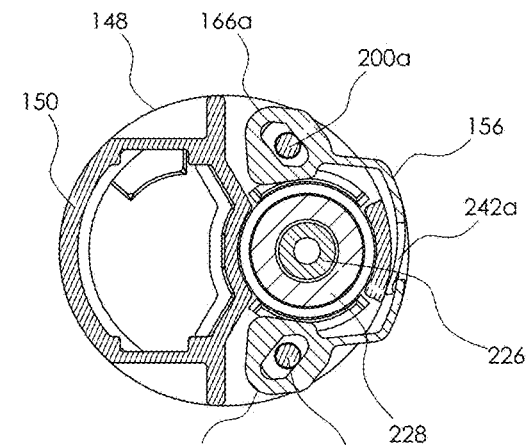
FIG. 13D is a cross-section view of the fluid connector connected to the end cap assembly of FIG. 13A similar to 13C illustrating the fluid connector latch in the unlatched position.
Figure 14A:
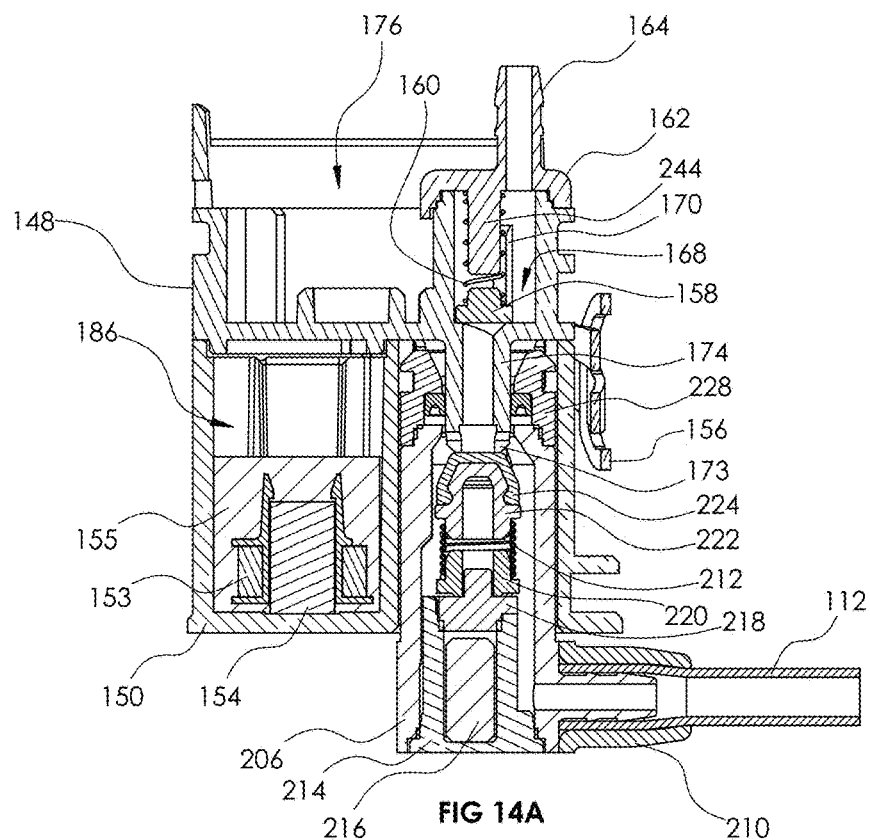
FIG. 14A is a cross-sectional view of the fluid connector connected to the end cap assembly of FIG. 13A taken along line 14A-14A in FIG. 13B.
Figure 14B:
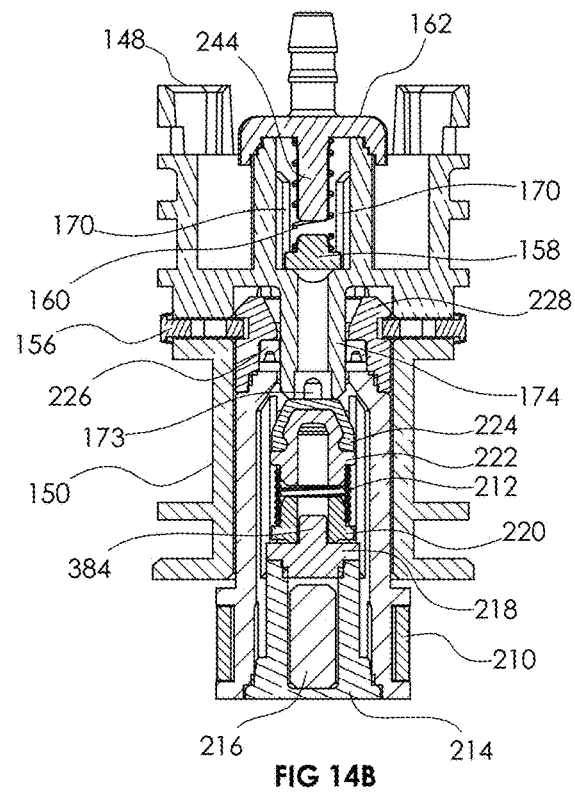
FIG. 14B is a cross-sectional view of the fluid connector connected to the end cap assembly of FIG. 13A taken along line 14B-14B in FIG. 13A.
Figure 15A:
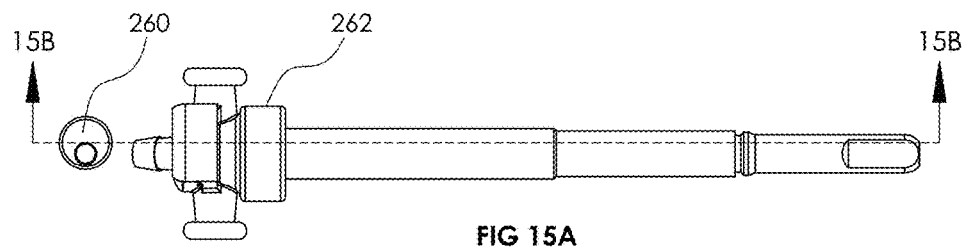
FIG. 15A is a front elevation view of select components of the power train assembly of FIG. 7B illustrating the orientation of the eccentric prior to installation.
Figure 15B:
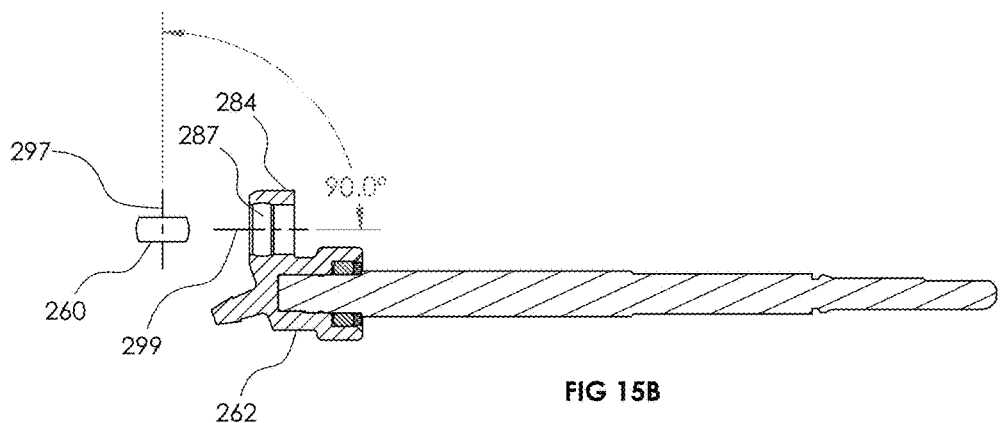
FIG. 15B is a cross-section view of select components of the power train assembly of FIG. 7B taken along line 15B-15B.
Figures 15C, 15E:
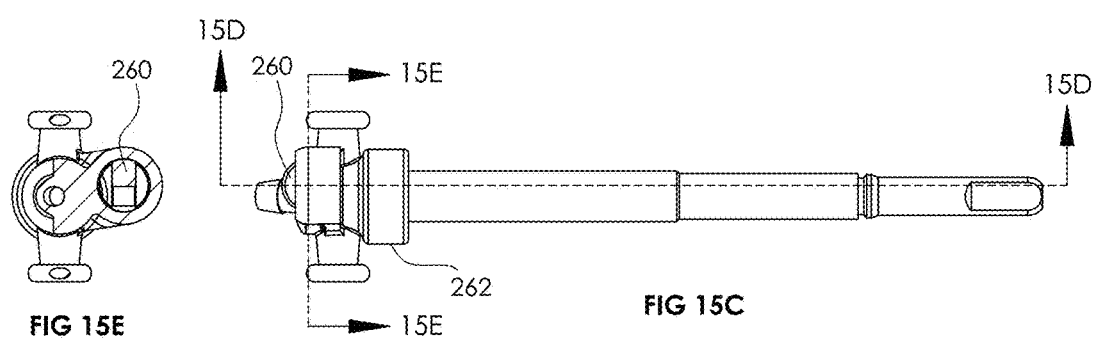
FIG. 15C is a front elevation view of select components of the power train assembly of FIG. 7B illustrating the orientation of the eccentric after installation but before rotating into the operating position.
FIG. 15E is a cross-section view of select components of the power train assembly of FIG. 7B taken along line 15E-15E in FIG. 15C.
Figure 15D:
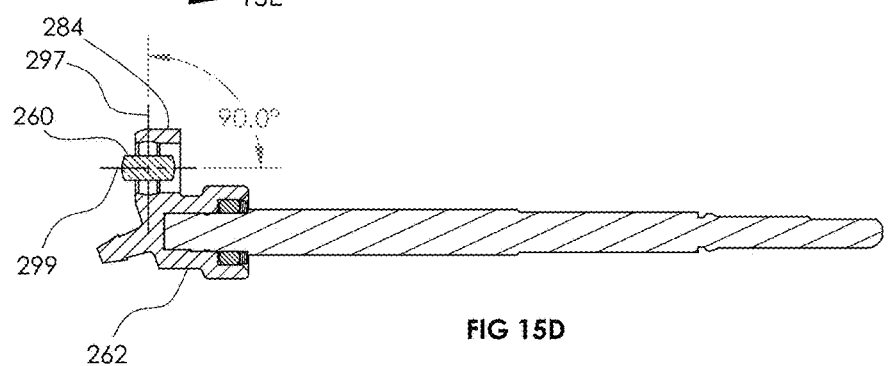
FIG. 15D is a cross-section view of select components of the power train assembly of FIG. 7B taken along line 15D-15D.

With reference to FIGS. 13C, 13D, and 14D, when the fluid connector 110 is initially inserted into the end cap assembly 132, the latch arms 166a, 166b of the latch 156 are forced outwards and slide on the pegs 200a, 200b. To insert the fluid connector 110 a user is not required to compress the latch button 231 on the housing, but rather due to the beveled configuration of the fitting top cap, the fitting connector 110 can insert directly into the end cap assembly 132 and the latch 156 will clip automatically to the fitting 110. In particular, as the user continues to insert the fluid connector 110 into the fitting cavity 184, the leaf springs 242a, 242b deform to allow the latch arms 166a, 166b to move outward in this manner.

Once the fluid connector 110 is in position, the leaf springs 242a, 242b spring back to the original configuration, forcing the latch arms 166a, 166b to move inwards and engage with the annular groove 227 on the fitting top cap 228 to secure the fluid connector 110 to the end cap assembly 132. As the annular groove 227 extends around the entire outer perimeter of the fitting top cap 228, the latch arms 166a, 166b can maintain their engagement with the fitting top cap 228, while still allowing the fluid connector 110 to rotate. In other words, as the fluid connector 110 swivels, the latch arms 166a, 166b travel along the groove 227, continuing to secure the fluid connector 110 to the end cap assembly 132, while allowing the fluid connector 110 to rotate relative thereto. This allows the fluid connector 110 and hose 112 to rotate relative to the handle 102, such that as a user is using the device 100, the hose 112 can move to stay out of the user's way, and the hose 112 is less likely to tangle.

Similarly, to release the fluid connector 110 from the end cap assembly 132, a user presses against a button 231 connected to the housing 118, which compresses the latch body 240, compressing the leaf springs 242a, 242b, deforming them and causing the latch arms 166a, 166b to pivot outwards, disengaging from the groove 227 of the fitting top cap 228, allowing the fluid connector 110 to be removed.

Assembly of the power train assembly 130 will now be discussed. With reference to FIGS. 7A-9C, the O-ring seal 280 and the seal retainer 266 are received around the shaft 281 on the bottom end of the output shaft 116. The terminal end of the output shaft 116, including the O-ring seal 280 and the seal retainer 226 are received into the shaft cavity 288 of the rocker arm 262. With reference to FIG. 8D, once the output shaft 116 is inserted into the shaft cavity 288, the fluid passageway 115 defined through the longitudinal length of the output shaft 116 is fluidly connected to the fluid connector 294 of the rocker arm 262.

The output shaft 116 includes a locking feature, key, or surface, such as a locking groove, flat surface, or the like, which is aligned with the locking feature 296 of the rocker arm 262 to prevent the output shaft 116 from moving relative to the rocker arm 262 so that the output shaft 116 will move with the rocker arm 262. The sleeve bearings 268, 270 are received at spatially discrete locations along the length of the output shaft 116. The location of the sleeve bearings 268, 270 may be varied based on the configuration, size, motor speed, housing configuration, and other design configurations.

With continued reference to FIGS. 7A-9C and reference to FIGS. 15A-15E, the eccentric 260 is then positioned so that the eccentric axis 297 is perpendicular to the cam follower axis 299 of the rocker arm 262. The eccentric 260 is then inserted into the eccentric cavity 286 of the rocker arm 262 such that the installation force applied to the eccentric 260 causes the cam follower structure 284 to deflect into an elongated oval shape to allow the installation of the eccentric 260. The eccentric 260 is then rotated so that the eccentric axis 297 is collinear with the cam follower axis 299. The mounting plate 252 is secured to the motor 250 by the fasteners 254a, 254b. The eccentric portion 258 of the drive shaft 256 is inserted into the aperture 276 of the eccentric 260. Each of the bumpers 264a, 264b are received in the grooves 292a, 292b on the spindles 272a, 272b of the rocker arm 262.

With reference to FIGS. 2A-2C and 4B, once the power train assembly 130 is connected, the battery assembly 136 and the motor 250 are electrically connected to the circuit board assembly 134. For example, the prongs 274 of the motor 250 may be connected via wires or contacts to the circuit board assembly 134 and, similarly, contacts on the battery assembly 136 may be connected via wires to the circuit board assembly 134.

The front chassis 122 and back chassis 124 are then connected around the battery assembly 136 and power train assembly 130. Each of the chassis 122, 124 include specifically designed compartments for each of the components of the battery assembly 136 and power train assembly 130. For example, front and back chassis 122, 124 together define a rocker arm cavity that allows the rocker arm 262 to oscillate, but provides a surface for the bumpers 264a, 264b to engage with and exert a force against the surfaces of the chassis 122, 124. As another example, each of the front and back chassis 122, 124 may include a slot for receiving a portion of the mounting plate 252 to secure the power train assembly 130 in a desired location relative to the front and back chassis 122, 124. The front chassis 122 and back chassis 124 may be connected together via fasteners 126a-126g and corresponding nuts 128a-128 g.

With reference to FIGS. 4A, 4B, 5A, 5E and 8B, after the front chassis 122 and back chassis 124 are secured together, the O-ring seal 146 is installed in the annular groove 176 of the lower end cap 150. The battery retention spring 133 is then fitted around the spring locating rib 197 of the upper end cap 148. The end cap assembly 132 is then fitted onto the lower sections of the connected chassis 122, 124 so that the prong 181 of the front chassis 122 and the prongs 183a, 183b of the back chassis 124 engage the securing apertures 180a-180c of the end cap assembly 132. The collars 144a, 144b are slid on the tube 142. The tube 142 is then connected to the fluid connector 294 of the rocker arm 262. Specifically, a first end of the tube 142 is press fit onto the fluid connector 294 and the collar 144b is secured around the fluid connector 294 and tube 142, securing the tube 142 to the rocker arm 262. The second end of the tube 142 is then inserted onto the nipple 164 of the cap 162 of the end cap assembly 132. Collar 144a is then received around the nipple 164 and tube 142 to secure the tube 142 to the cap 162. In this manner the tube 142 fluidly connects the valve assembly 190 and fluid connector 110 to the rocker arm 262 and output shaft 116. The boot ring 140 is then fitted in the annular groove of the boot 138. The boot 138 is then slid over the output shaft 116 and fitted to the top end of the connected chassis 122, 124 so that the boot ring 140 clamps the top end of the boot 138 onto the output shaft 116 to form a watertight seal.

Figure 3A:
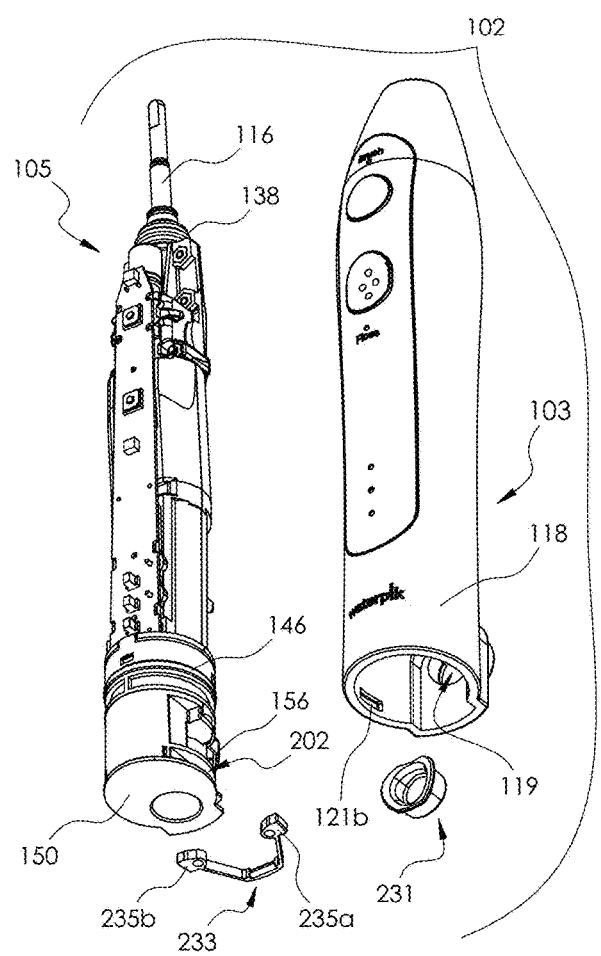
FIG. 3A is an exploded view of an irrigating toothbrush handle.
Figure 3B:
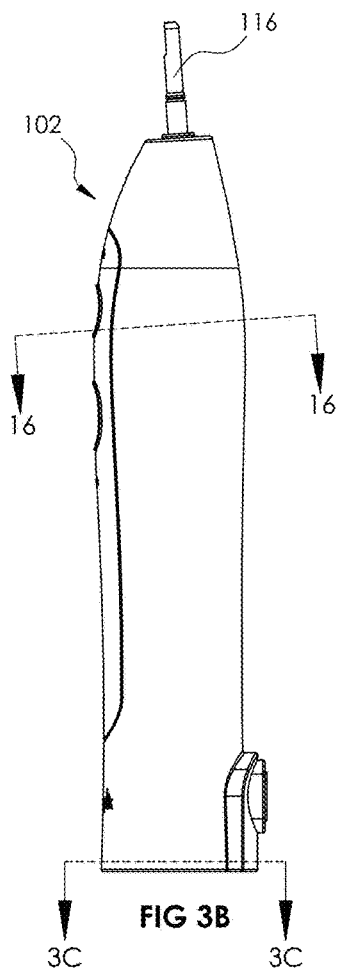
FIG. 3B is a side elevation view of an irrigating toothbrush handle.
Figure 3C:
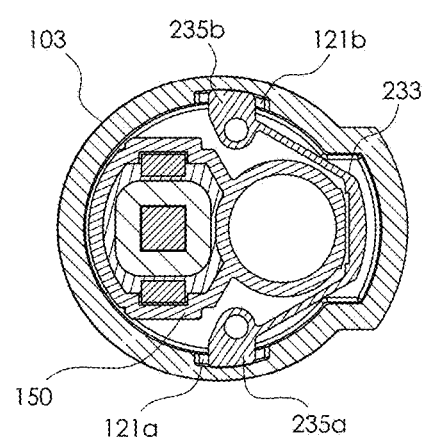
FIG. 3C is a cross-section view of an irrigating toothbrush handle taken along line 3C-3C in FIG. 3B.

With reference to FIGS. 3A-3C, the handle 102 is assembled by sliding the retainer 233 into the two arm compartment 202 of the lower end cap 150. The latch button 231 is fitted into the aperture 119 of the handle housing assembly 103. The handle housing assembly 103 is then received over the chassis assembly 105 while compressing the retainer nubs 235a, 235b inwardly so that they provide clearance to the handle housing assembly 103. The chassis assembly 105 is fitted inside the handle housing assembly 103 such that the retainer nubs 235a, 235b spring outwardly into the retention pockets 121a, 121b and so that the output shaft 116 is the only component that extends out of the handle housing assembly 103. The retainer nubs 235a, 235b of the retainer 233 assist in securing the various internal components in a desired position in the handle housing assembly 103 and help to prevent movement of the components during operation of the irrigating and brushing device 100. The boot seal 135 and the O-ring seal 146 of the chassis assembly 105 are compressed by the inside walls of the handle housing assembly 103 to provide an upper and lower water tight seal for the internal components of the handle 102.

Once the device 100 is assembled, the brush assembly 104 may be connected to the output shaft 116. The user places the brush assembly 104 onto the output shaft 116 and rotates the brush assembly 104 until an alignment flat 351 (see FIG. 1B) of the output shaft 116 mates with a keyed surface of the retainer 310. Then, the user presses the brush assembly 104 onto the output shaft 116 until the lateral arms 368a, 368b of the spring retainer clip 318 seat within the clip recess 353 (see FIG. 1B). The diameter of the output shaft 116 increases along a beveled edge immediately adjacent the clip recess 353. The clip arms 368a, 368b of the spring retainer clip 318 expand laterally outward along this edge and then, when past the beveled edge, the clip arms 368a, 368b contract laterally inward to lodge within the clip recess 353. Typically, an audible "click" can be heard by the user when the clip arms 368a, 368b lodge within the clip recess 353 so that the user knows that the brush assembly 104 is securely attached to the handle 102. The gauge, material strength, and elasticity of the wire forming the spring retainer clip 318 are specifically chosen to ensure retention of the brush assembly 104 on the output shaft 116 under the operating pressures of the water jet function and further to reliably expand during engagement and disengagement of the brush assembly 104 over an appropriate number of cycles equivalent to or greater than an estimated life of the bristles 106.

To disconnect a brush assembly 104 from the output shaft 116, the user pulls the brush assembly 104 away from the handle 102 with a sufficient force to overcome the force exerted by the clip arms 368a, 368b, which causes the arms to deform and slide out of the clip recess 353, allowing the brush assembly 104 to be removed.

Operation of the Irrigating Brushing Device

To operate the irrigating toothbrush device 100 with an irrigating function the user first connects the fluid connector 110 to the handle 102 (if not already connected) by inserting the fitting 206 into the end cap assembly 132 as discussed above to open the valve assembly of the fluid connector 110. The user then activates a pumping assembly, such as one connected to a countertop or base oral irrigation unit to pump fluid from a reservoir to the hose 112. With reference to FIGS. 2A-2B and 14A-14B, the fluid flows into the fitting 206 from the hose 112 and flows around the fitting bottom cap 214 and around the poppet 222 and poppet cap 224 into the tube connector 174 of the end cap assembly 312. The fluid force pushes against the poppet 158 in the valve assembly 190, overcoming the biasing force exerted by the poppet spring 160, allowing fluid to exit the tube connector 174 and enter the valve cavity 168.

With continued reference to FIGS. 2A-2B and 14A-14B, the fluid flows around the poppet 158 and into the nipple 164 of the cap 162. With reference to FIGS. 2A-2B and 4A, fluid flows from the nipple 164 of the cap 162 into the tube 142. The fluid flows through the tube 142 into the fluid connector 294 of the rocker arm 262. From the fluid connector 294, the fluid flows into the fluid passageway 115 of the output shaft 116 via the aperture shaft cavity 288. With reference to FIGS. 2A-2B, 11D and 12B, the fluid flows through the passageway 115 and exits through the aperture 358 and sidewall openings of the retainer 310 and enters into the fluid passageway 322 of the tip shaft 308. From the fluid passageway 322, the fluid flows into the end of the brush assembly 104 and into the nozzle 108 and exits into a user's mouth.

With reference to FIGS. 1A and 2A-2B, during or after irrigation, to activate the brush function, the user selects one of the control buttons 114, such as an off/on switch, to activate the brush function. In particular, when the on/off control button is selected a contact on the circuit board assembly 134 is activated and power from the battery assembly 136 is provided to the motor 250, causing the drive shaft 256 to rotate.

Figure 16A:
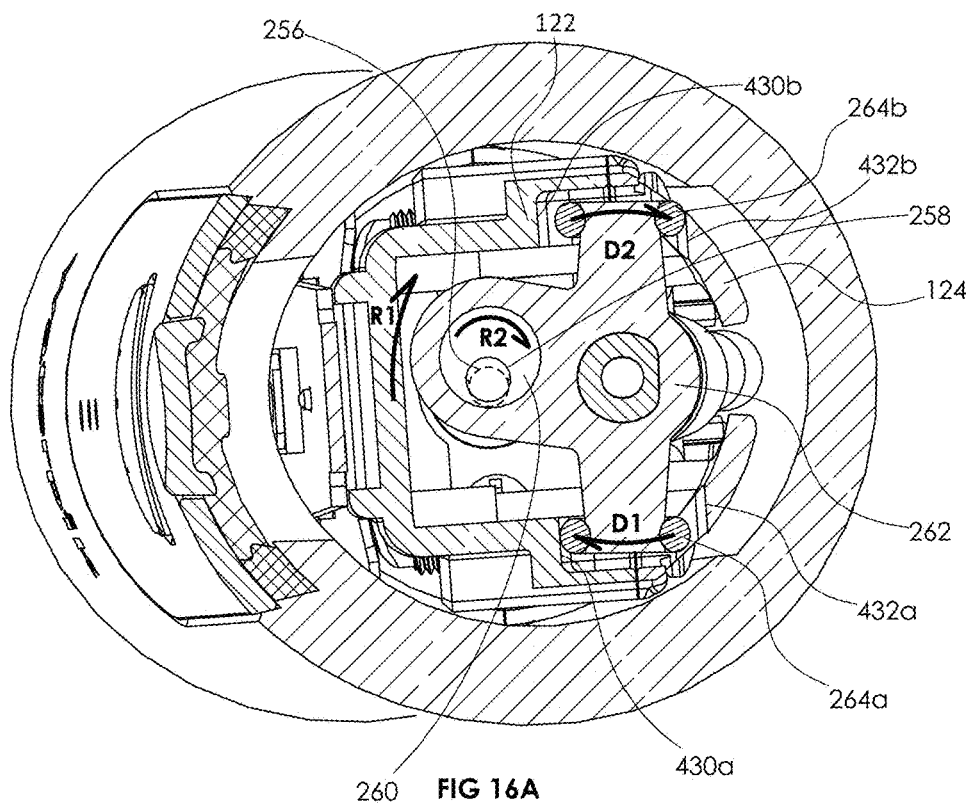
FIG. 16A is a cross-section view of the irrigating toothbrush taken along line 16-16 in FIG. 3B illustrating the power train assembly in a first position.
Figure 16B:
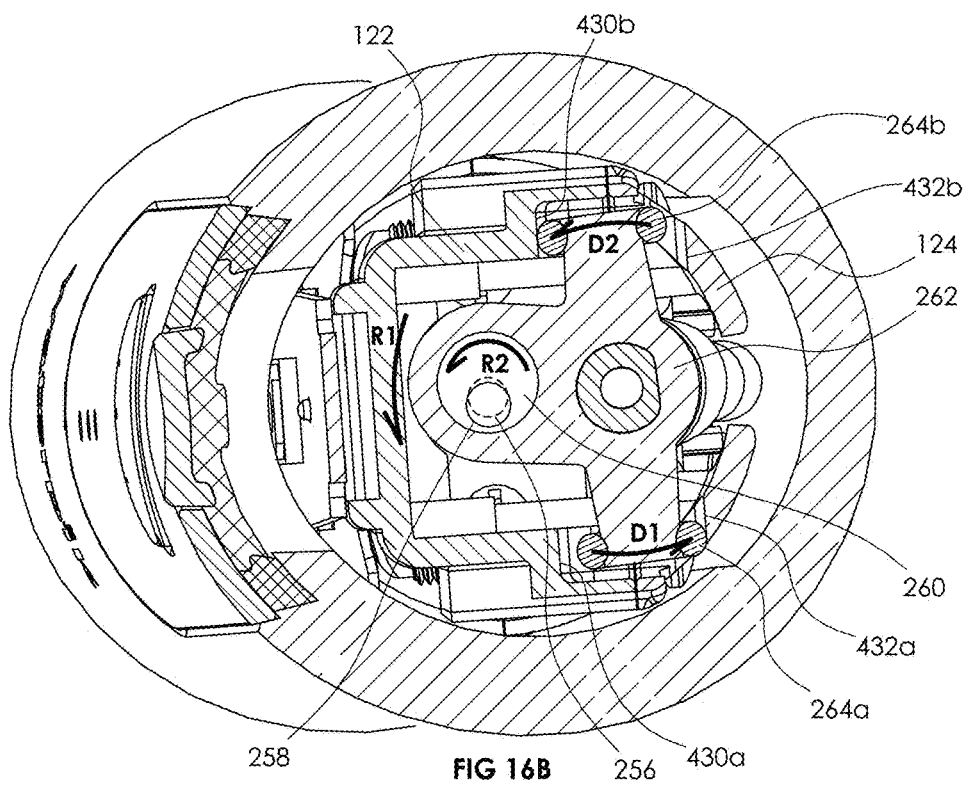
FIG. 16B is a cross-section view of the irrigating toothbrush similar to FIG. 16A illustrating the power train assembly in a second position.

FIGS. 16A and 16B illustrate a cross-section view of the irrigating brushing device 100 taken along line 16 in FIG. 3B. FIG. 16A illustrates the power train assembly 130 in a first position and FIG. 16B illustrates the power train assembly 130 in a second position. As the drive shaft 256 rotates, the eccentric portion 258 connected to the drive shaft 256 rotates, due to the mounting constraints of the output shaft 116, this creates an oscillating rotary motion in the eccentric 260 centered about the axis of the eccentric 260 within the eccentric cavity 286 of the cam follower 284. This causes the cam follower 284 to move correspondingly in an oscillating rotary motion centered about the axis of the output shaft 116. Additionally, due to the constraints of the front and back chassis 122, 124, the movement of the rocker arm 262 is restricted. Specifically, as the cam follower 284 moves with the eccentric 260, the rocker arm 262 rotates, causing the spindles 272a, 272b to move back and forth. With reference to FIG. 16A, as the first spindle 272a moves in a first direction D1, the second spindle 272b moves in an opposite second direction D2. In other words, the rocker arm 262 rocks back and forth within the cavity defined by the front and back chassis 122, 124 with the degrees of movement being defined by the continuous rotational motion of the eccentric portion 258 of the drive shaft 256 and by the mounting restraints of the bearings 268, 270 on the output shaft 116.

With reference to FIG. 16A, when the spindles 272a, 272b reach the end of their rotational travel in the respective first and second directions D1, D2, the bumpers 264a, 264b engage the bumper surface 430a of the front chassis 122 and bumper surface 432b of the back chassis 124 respectively and compress, absorbing rotational momentum. With reference to FIG. 16B, as the rocker arm 262 continues to move the spindles 272a, 272b begin to reverse their rotational directions and the bumpers 264a, 264b expand, returning momentum to the spindles 272a, 272b as they do so. In this manner, the bumpers 264a, 264b assist in reducing the electrical power required to operate the motor 250 by reversing the rotational momentum at the end of travel, which in turn increases the number of cycles per battery charge that the motor 250 can be operated. Further, the bumpers 264a, 264b help to reduce the stress on the component parts of the device 100, such as the components of the power train 130, to further extend the life of the device 100. In embodiments, where the spindles 272a, 272b themselves form the deformable members (e.g., are made of flexible materials), the ends of the spindles 272a, 272b may directly engage the interior surfaces of the front chassis 122 and back chassis 124 in order to absorb and reapply energy. In these instances, the O-rings or other deformable materials may be omitted.

As the rocker arm 262 oscillates, with the movement constrained by the front and back chassis 122, 124, the output shaft 116 connected thereto oscillates with the rocker arm 262. The bearings 268, 270 cushion the output shaft 116 as it rotates within the chassis 122, 124 to help reduce vibrations from being transmitted to the user holding the handle 102. The oscillations of the output shaft 116 cause the brush assembly 104, which is connected thereto by the end cap 314 and retainer 310, to oscillate as well. Because the entire brush assembly 104 oscillates and the fluid flows through the output shaft 116, the brush mechanism can be used simultaneously with the irrigating operation. However, while both the brushing and irrigating functions can be used simultaneously, each of these functions can also be used independently from each other.

As the brush assembly 104 is oscillating the user may place the bristles 106 against surfaces within his or her mouth, such as teeth, gums, etc. As the user moves the irrigating toothbrush 100 to reach different locations in his or her mouth, the fluid connector 110 can rotate to ensure that the hose 112 does not get tangled or inadvertently pulled from the handle 102. Due to the connection features of the fluid connector 110, as described above, the fluid connector 110 can rotate 360 degrees. Additionally, as the end cap assembly 132 includes a sealing valve that seals the tube connector 174 when the fluid connector 110 is removed, the irrigating toothbrush 100 can be used without the fluid connection to the base unit, i.e., in a brushing only mode, allowing multiple uses of the same device and allowing a user to travel with only the handle 102 portion of the system.

Communication with Base Unit

Figure 17:
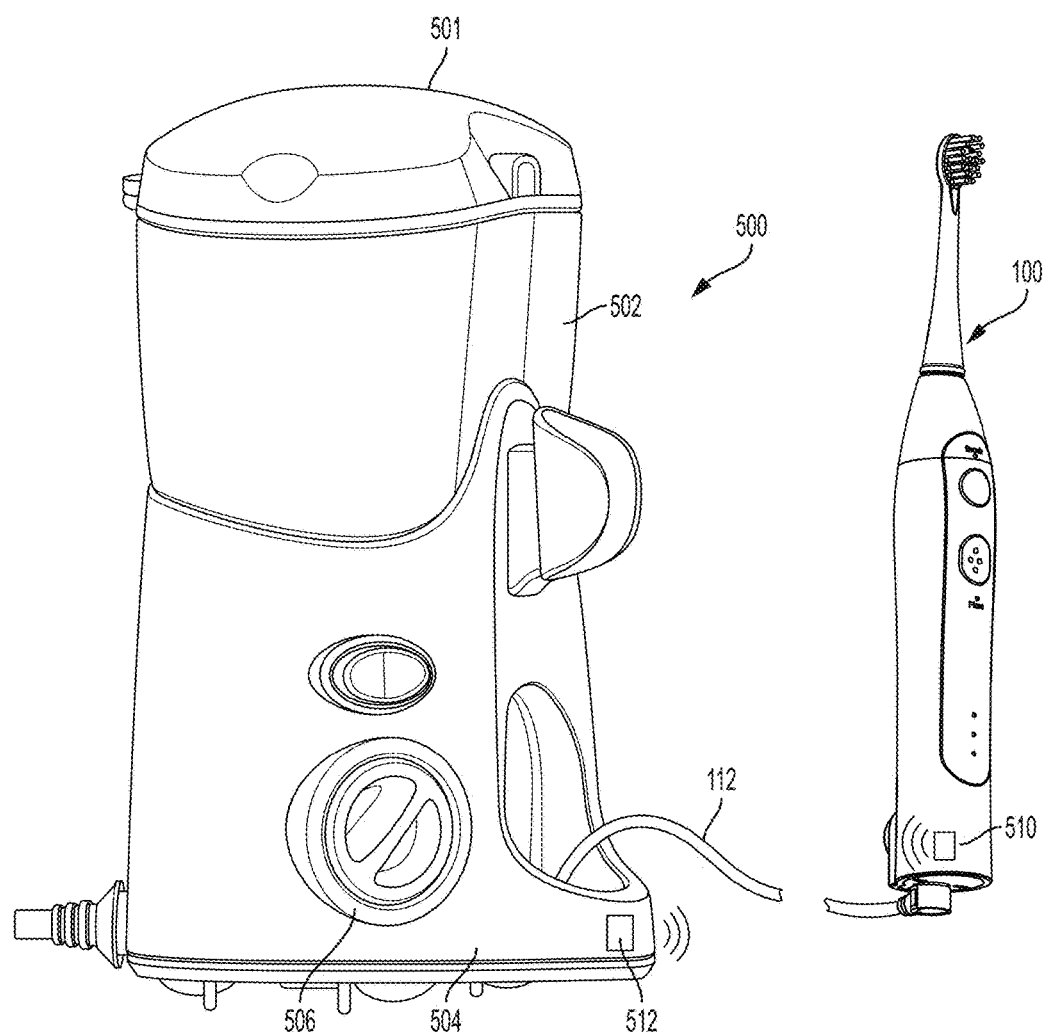
FIG. 17 is a side isometric view of an irrigating system including an irrigating toothbrush and a base unit.

As mentioned above, the irrigating toothbrush 100 may be in fluid communication with a reservoir and base unit. FIG. 17 illustrates a perspective view of an irrigating system 500 including the irrigating toothbrush 100 and a base unit 501. The base unit 501 may be an oral irrigating countertop unit and includes a reservoir 502, a base 504 housing a pumping system (not shown), and one or more base controls 506. The base unit 501 also includes a communication module 512 for communicating with a corresponding communication module 510 on the device 100. In one embodiment, the communication modules 510, 512 may be radio wave communication modules, using short distance communication protocols, such as Bluetooth, WiFi, ZigBee, or the like, that transmit and receive radio wave signals. For example, a user may activate one or more of the control buttons 114 on the device 100 in order to change the fluid pressure output by the pumping system of the base unit 501 and/or activate or deactivate the irrigating function. In this example, the communication module 510 on the device 100 transmits the pressure control signal to the communication module 512, which then provides the signal to the pumping system. In this manner, the user can dynamically adjust the pressure, selectively turn on/off the system 500, and/or control other characteristics of the system 500 such as activating a massage mode feature, etc.

In other embodiments, the irrigating brushing device 100 may communicate with the base unit 501 in other manners, such as a wired connection. For example, the hose 112 may include wires extending between the two devices that are connected to and/or embedded within the hose 112. In these instances the communication wires may be shielded from the fluid within the hose 112.

Alternative Embodiments

Other examples of the irrigating toothbrush will now be discussed. It should be noted that in the discussion below elements that are the same between embodiments have the same numbering. Additionally, any of the features described with respect to any particular embodiment may be used with any other embodiment.

Figure 21:
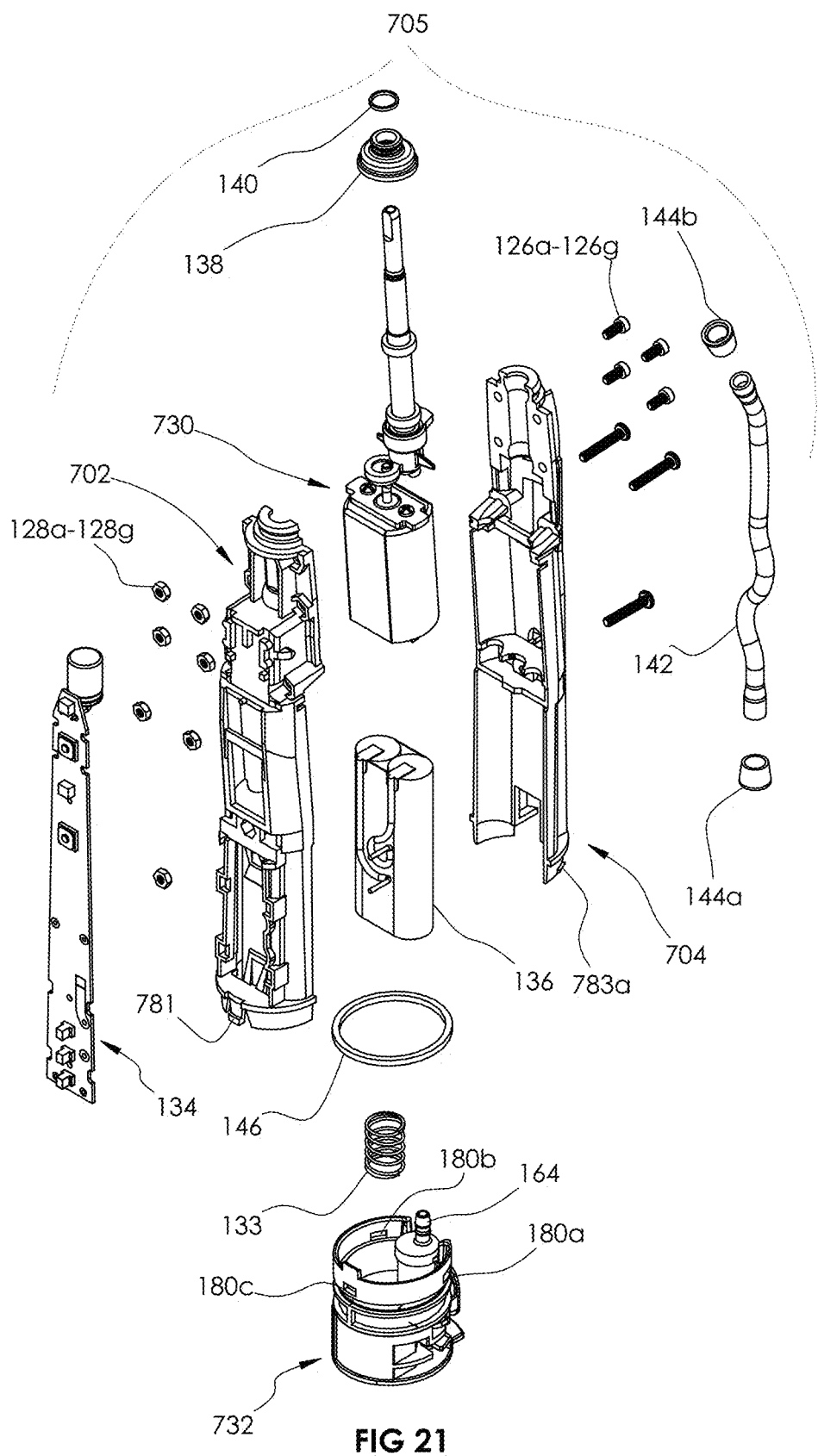
FIG. 21 is an exploded view of the irrigating toothbrush of FIG. 20A.

FIGS. 20A-21 illustrate various views of another embodiment of the irrigating toothbrush with certain features hidden. With reference to FIGS. 20A-21, in this embodiment, the irrigating toothbrush 700 may be substantially similar to the irrigating toothbrush 100 but may include a modified power train assembly 730, end cap assembly 732, and fluid connector. Additionally, due to changes with the power train assembly 730, a chassis assembly 705 including a front chassis 702 and rear chassis 704 (or first chassis and second chassis) may be varied as compared to the first embodiment. Each of these components will be discussed in turn below.

Figures 22A, 22B:
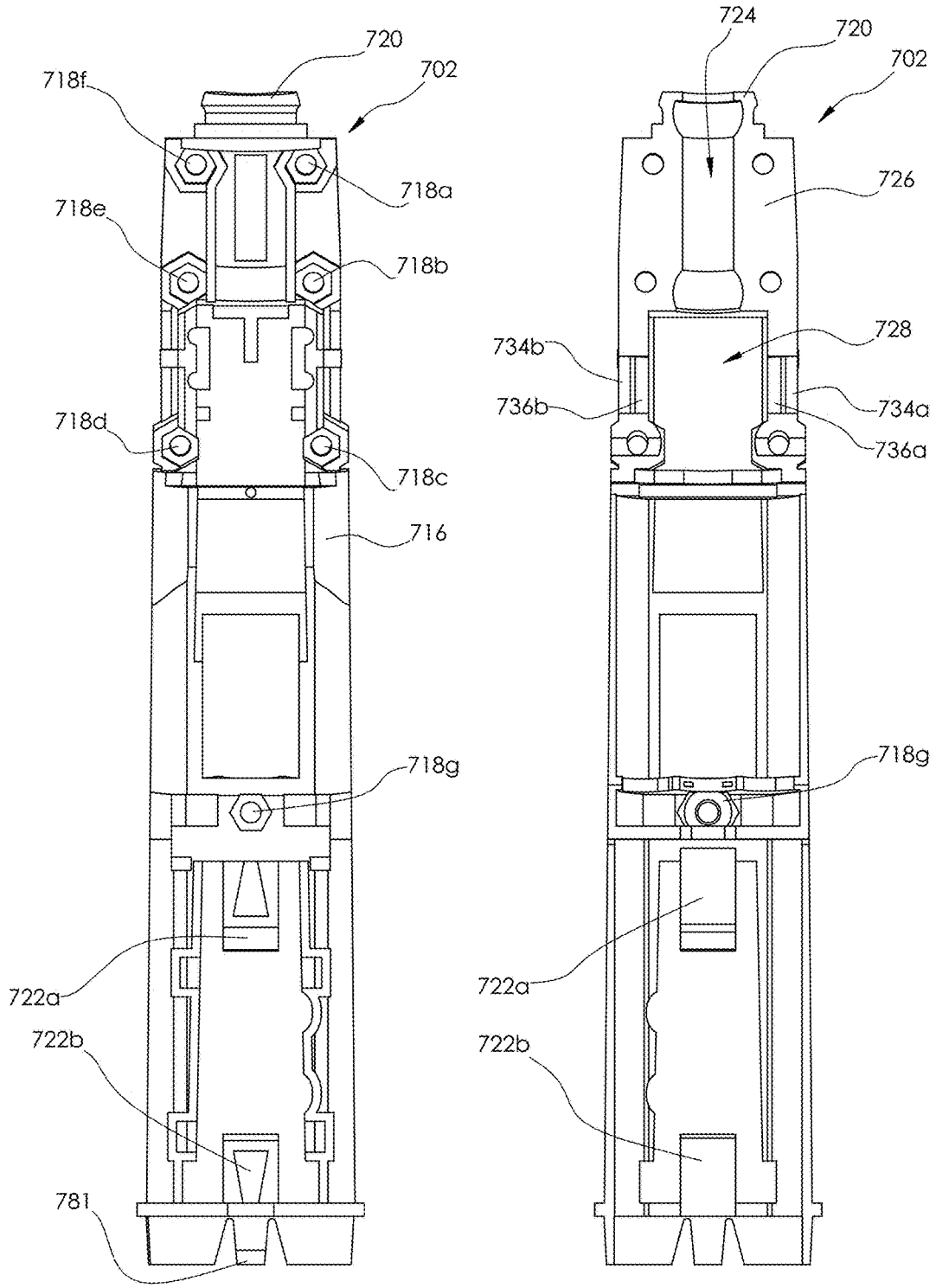
FIG. 22A is a front elevation view of a front chassis for the irrigating toothbrush of FIG. 20A.
FIG. 22B is a rear elevation view of the front chassis of FIG. 22A.

With reference to FIGS. 22A and 22B, the front or first chassis 702 is configured to define an internal structure that houses and defines a scaffold for the power train assembly 730. The front chassis 702 includes an outer surface 716 and an interior surface 726, where the interior surface 726 is configured to mate with the rear chassis 704 as discussed below. A top end 720 of the front chassis 702 defines a cylindrical outer surface that optionally includes one or more grooves to receive a sealing member, such as a boot seal or O-ring. The front chassis 702 may also include one or more openings defined therein. These openings are configured to receive various components of the power train assembly 730 (e.g., drive assembly, motor, and/or batteries). Additionally, the openings are hollow and so reduce the overall weight of the device 700. In some embodiments, the front chassis 702 may include two brackets 722a, 722b that extend into a bottom cavity. The brackets 722a, 722b may be used to secure the batteries (or other component) in a desired position relative to the internal components secured to the front chassis 702. A shaft channel 724 may be defined through a central portion of the front chassis 702 on the rear surface. The shaft channel 724 may vary in width along its length to accommodate bearings or other features that may be received around the drive or output shaft 116.

With reference to FIG. 22B, a power train cavity 728 is defined on the interior surface 726 towards the top end 720. The power train cavity 728 includes a back surface and is recessed from the interior surface 726 (i.e., extends outwards towards the outer surface 716). The power train cavity 728 is configured to receive and support components of the power train assembly 730, such as the conservation features (e.g., rocker arm).

A first engagement surface 734a and a second engagement surface 734b are defined on the two side edges of the power train cavity 728. The two engagement surfaces 734a, 734b are recessed below the interior surface 726 but raised above the power train cavity 728. In some embodiments, the two engagement surfaces 734a, 734b are defined as planar surfaces that extend longitudinally along a portion of the length of the power train cavity 728 and the depth of the recess may vary along their length. As will be discussed below, the recessed depth of the engagement surfaces 734a, 734b defines, in part, the width of a slot for receiving wings of the power train assembly 730. Two angled walls 736a, 736b extend at an angle between the engagement surfaces 734a, 734b and the lateral sidewall of the power train cavity 728.

A bottom end of the front chassis 702 may include one or more retaining features 781, such as prongs or nubs, that are configured to connect to the end cap assembly 732 in a similar manner as described with respect to the irrigating toothbrush 100 of FIG. 1A. The retaining features 781 may be spaced around the outer surface of the front chassis 702.

With continued reference to FIGS. 22A and 22B, the front chassis 702 may also include a plurality of fastening apertures 718a-718g that are used to receive fasteners to secure the front chassis 702 to the rear chassis 704 in a similar way as the front chassis 122 and rear chassis 124 for the irrigating toothbrush 100 are connected together.

Figure 23A:
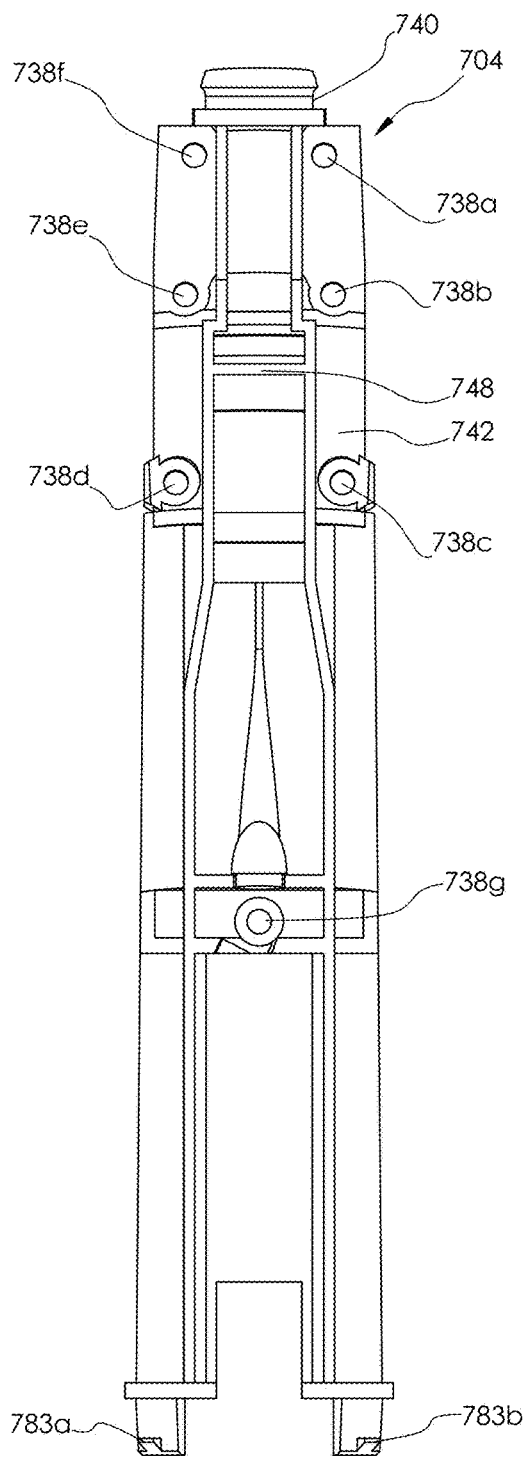
FIG. 23A is a front elevation view of a rear chassis for the irrigating toothbrush of FIG. 20A.
Figure 23B:
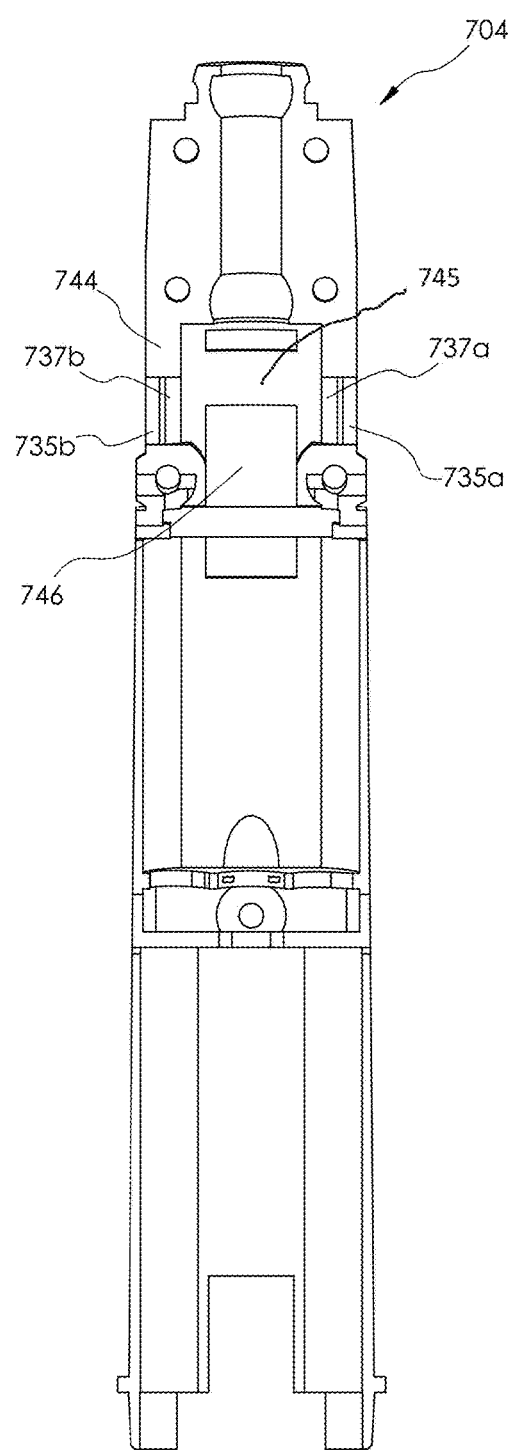
FIG. 23B is a rear elevation view of the rear chassis for the irrigating toothbrush of FIG. 20A.

With reference to FIGS. 23A and 23B, the rear chassis 704 may be somewhat similar to the front chassis 702 and is configured to connect to the front chassis 702. The rear chassis 704 includes an outer surface 742 and interior surface 744. A top end 740 includes a similar shape as the top end 720 of the front chassis 702 and is configured to mate with the top chassis 702 to define the shaft channel 724. Similar to the front chassis 702, the rear chassis 704 includes a plurality of fastening apertures 738a-738g positioned so as to align with the corresponding fastening apertures 718a-718g of the front chassis 702 to allow the two chassis 702, 704 to be secured together with fasteners.

A plurality of retaining features 783a, 783b may be defined on the bottom end of the rear chassis 704 and are similar to the retaining features 781 on the front chassis 702. These retaining features 783a, 783b are configured to connect to the end cap assembly 732 and secure it to the chassis 704.

The rear chassis 704 may define a power train cavity 745 having an access aperture 746 defined through the front wall thereof. The power train cavity 745 is configured to receive and support various components of the power train assembly 730 and the access aperture 746 allows the fluid tube 142 to be connected to the power train assembly 730 and fluidly connect to the brush tip. In some embodiments a brace 748 may extend across a width of the access aperture 746 to provide support for the power train components received within the power train cavity 745, while still allowing the fluid tube to be inserted through the rear chassis 704 and connect to the power train assembly 730. The position and size of the brace 748 may be varied as desired.

With reference to FIG. 23B, similar to the front chassis 702, the rear chassis 704 may include two engagement walls 735a, 735b positioned on a longitudinal edge of the power train cavity 745. The engagement walls 735a, 735b are recessed from the interior surface 744 and may be recessed at a taper, such as that a top end of the engagement walls 735as, 735b is closer to the interior surface 744 as compared to a bottom end of the engagement walls 735a, 735b. The depth of the recess for the engagement walls 735a, 735b defines, in part, a slot that the conservation features (as discussed below) are received within and helps to define the degrees of movement for the conservation features. As such, the recess depth may be varied as desired.

Angled walls 737a, 737b connect the interior edge of the engagement walls 735a, 735b to the edge of the sidewalls of the power train cavity 745. The slope of the angled walls 737a, 737b may vary based on the size and configuration of the conservation features.

Figure 24A:
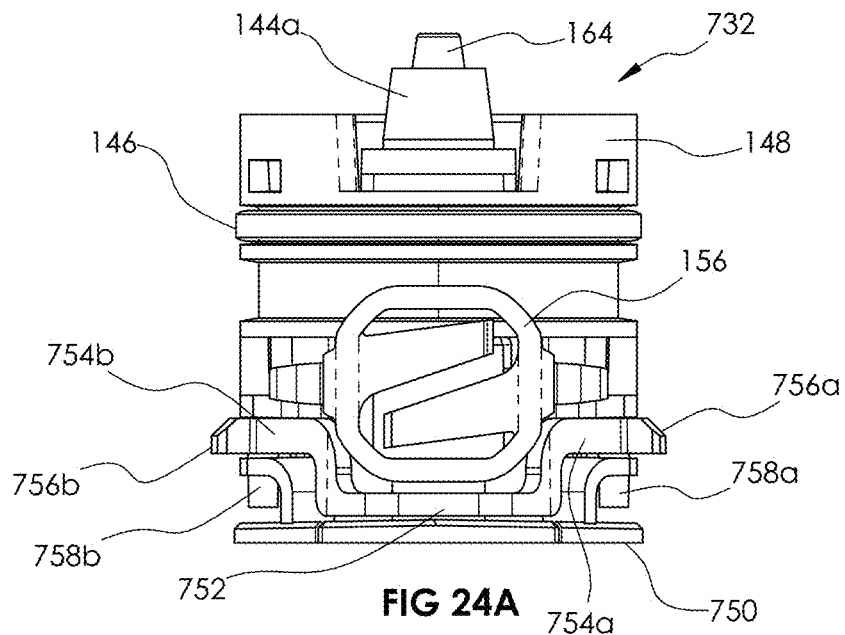
FIG. 24A is an isometric view of an end cap assembly for the irrigating toothbrush of FIG. 20A.
Figure 24B:
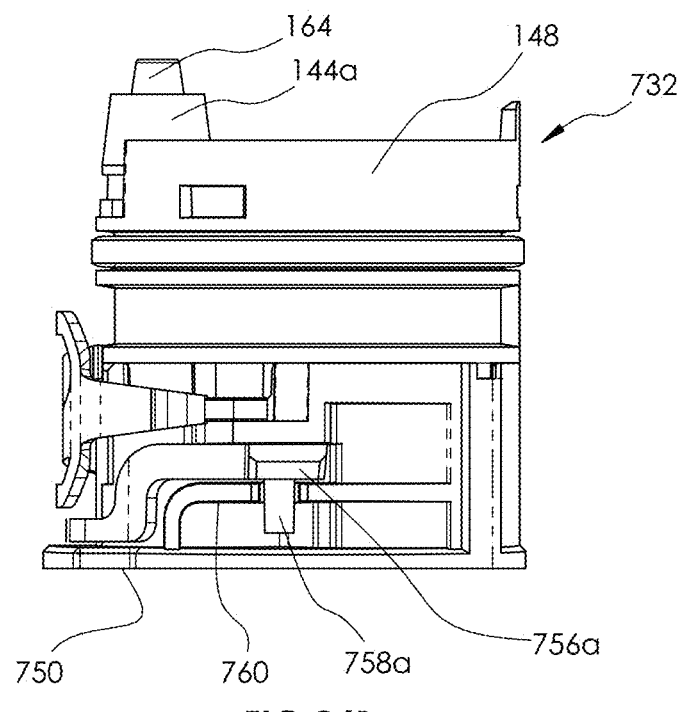
FIG. 24B is a left side elevation view of the end cap assembly of FIG. 24A.

The end cap assembly 732 will now be discussed. FIGS. 24A and 24B illustrate various views of the end cap assembly 732. The end cap assembly 732 may be substantially similar to the end cap assembly 132 and may connect to the chassis 702, 704 and fluid connector in a similar manner as described above. With reference to FIGS. 24A and 24B, the end cap assembly 732 in this example may include a different configuration for a retainer 752. The retainer 752 connects the end cap assembly 752 to the outer housing 103 of the irrigating brush 700. In one embodiment, the retainer 752 includes two arms 754a, 754b that extend first perpendicular from a main section of the retainer 752 and then second are extend parallel to the main section such that the arms 754a, 754b curve around the outer surface of a lower end cap 750. In this manner, a dip is defined in the retainer 752 which allows the bottom edge of the fluid connector latch 156 to be fit around the lower end cap 750 and be able to move relative to the end cap 750 without interference from the retainer 752.

Each of the arms 754a, 754b include retainer numbs 756a, 756b that extend outwards from the terminal end of the arms 754a, 754b. The retainer nubs 756a, 756b may include a top beveled surface that transitions to a planar surface parallel to the outer surface of the arms 754a, 754b. The nubs 756a, 756b are configured to engage with the interior of the housing similar to the retainer numbs 235a, 235b shown in FIG. 3C.

With reference to FIG. 24B, the retainer 752 may also include posts 758a, 758b that extend downwards from the arms 754a,754b below the nubs 756a, 756b. The posts 758a, 758b connect to receiving brackets defined by a shelf 760 in the lower end cap 750. The posts 758a, 758b allow the arms 754a, 754b to pivot relative to the lower end cap and define the pivot axis for the arms 754a, 754b as the retainer 752 engages and disengages from the housing 103. In other examples, such as retainer 233, the posts may be defined on the lower end cap 150, rather than the retainer, but the functionality is similar.

With the change to the retainer 752, the lower end cap 750 is slightly different from the lower end cap 150. In particular, a shelf 760 that defines a cutout to define a bracket for receiving the posts 758a, 758b of the retainer 752 is defined on two sides of the lower end cap 750. Accordingly, rather than the retainer being received in the arm compartments 202 as in the lower end cap 150, the retainer 752 is positioned on the top surface of the shelf 760 and the posts inserted into the cutouts defined by the shelf 760.

Figure 25A:
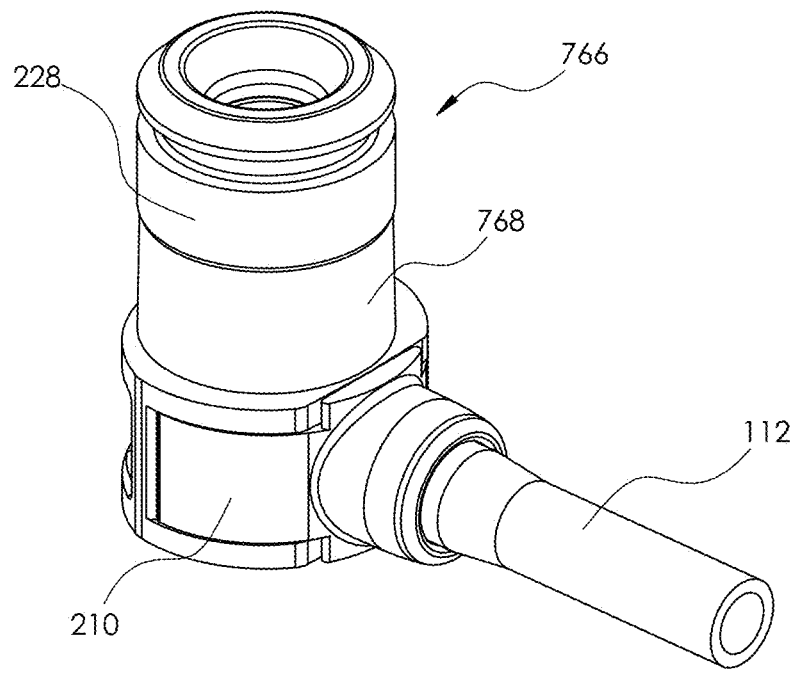
FIG. 25A is a rear isometric view of a fluid connector for the irrigating toothbrush of FIG. 20A.
Figure 25B:
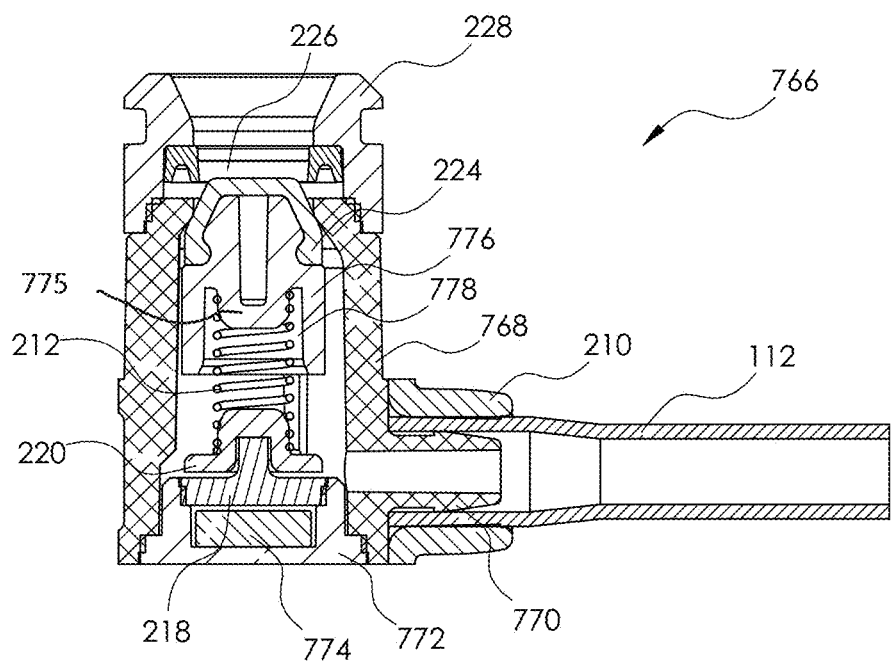
FIG. 25B is a cross-section view of the fluid connector of FIG. 25A taken along line 25B-25B in FIG. 25A.
Figures 26A, 26B:
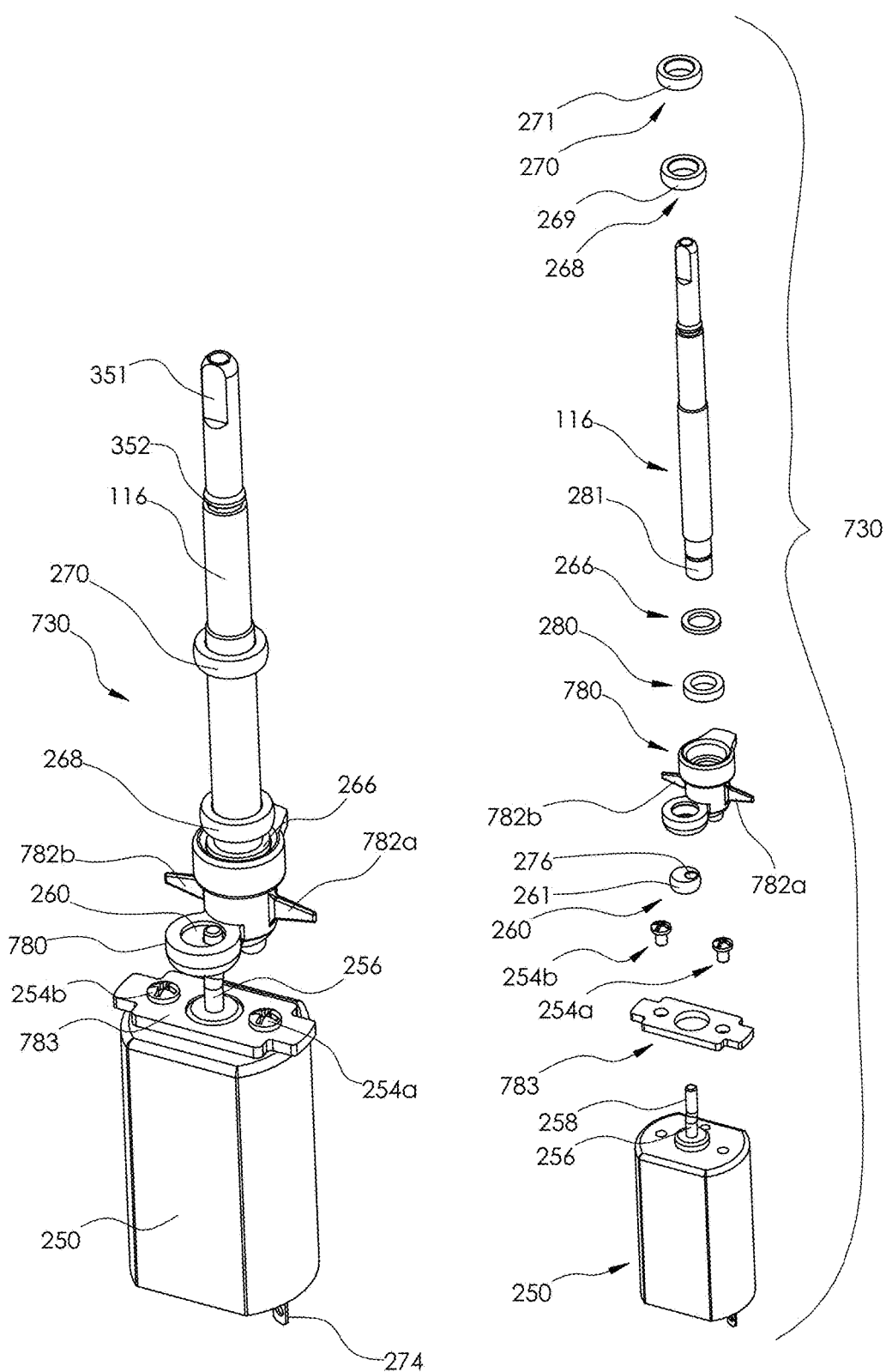
FIG. 26A is an isometric view of a power train assembly for the irrigating toothbrush of FIG. 20A.
FIG. 26B is an exploded view of the power train assembly of FIG. 26A.

In some embodiments, a modified fluid connector 766 having a shorter height may be connected to the irrigating toothbrush. FIGS. 25A and 25B illustrate various views another example of a fluid connector 766 that connects to the irrigating brush. With reference to FIGS. 25A and 25B, the fluid connector 766 may be substantially similar to the fluid connector 110, but include an alternate valve assembly that allows the height of the fluid connector 776 to be reduced. The reduced height allows the irrigating toothbrush 700 to more easily connect to the base unit and be positioned in an upright manner. The fluid connector 766 may include a fitting 768 that is similar to the fitting 206 of the fluid connector 110 but may have a shorter overall height. The fitting 768 includes a tube connector 770

With reference to FIG. 25B, the valve assembly of the fluid connector 766 is similar to the valve assembly of the fluid connector 110 but includes a modified poppet 776, pin 774, and bottom cap 772. The poppet 776 includes a head portion and a sleeve 778 that extends downwards from the outer perimeter of the head portion. The sleeve 776 may be a cylindrical shape and defines a cavity that receives the spring 212 for the valve assembly. The spring 212 seats on a post 775 extending downward from a center of the head portion of the poppet 766. The poppet 776 operates similar to the poppet 222 in the fluid connector 110 but includes the sleeve 776 that at least partially encloses the spring 212. This enclosure provides additional rigidity to the poppet 776 to help prevent the poppet from twisting or binding up during use.

With continued reference to FIG. 25B, the fluid connector 766 may also include a pin 774, which may be a magnetic element, that has a reduced height as compared to the pin 216 in the fluid connector 110. In particular, in this example, the pin 774 may be shaped as a circular disc as compared to the elongated cylindrical shape of the pin 216. The increased width of the pin 774 may be configured to provide a similar magnetic force to connect the fluid connector 766 to the base unit as the elongated pin 216. Alternatively, the magnetic force of the pin 774 may be configured to exert an increased or decreased magnetic force.

The power train assembly 730 for the irrigating toothbrush 700 will now be discussed in more detail. FIGS. 26A-27D illustrate the power train assembly 730. The power train assembly 730 may be substantially similar to the power train assembly 130. However, the power train assembly 730 may include an integrally formed conservation component or feature and a reduced width motor bracket. In particular, a rocker arm 780 for the power train assembly 130 may include wings 782a, 782b or spindles integrally formed with the main body of the rocker arm. The wings are configured to deform and spring back to an original shape and thus the deformable elements (e.g., O-rings) or the rocker arm 262 may be omitted. The rocker arm 780 will be discussed in more detail below.

With respect to the motor bracket 783, in this embodiment, the bracket may have a reduced size to allow a thinner housing 103 for the irrigating toothbrush 700. In one embodiment, motor bracket 783 forms a generally rectangular body having a width that is smaller than a width of the motor 250. Additionally, the bracket 783 tapers at the two ends to define tabs that extend from either end of the bracket

783. The tabs provide additional structure to secure motor and the bracket 783 to the interior of the front chassis 702 and the rear chassis 704 in a similar manner as the motor bracket 252, but allow the housing to have a decreased width as compared to other embodiments.

Figure 28A:
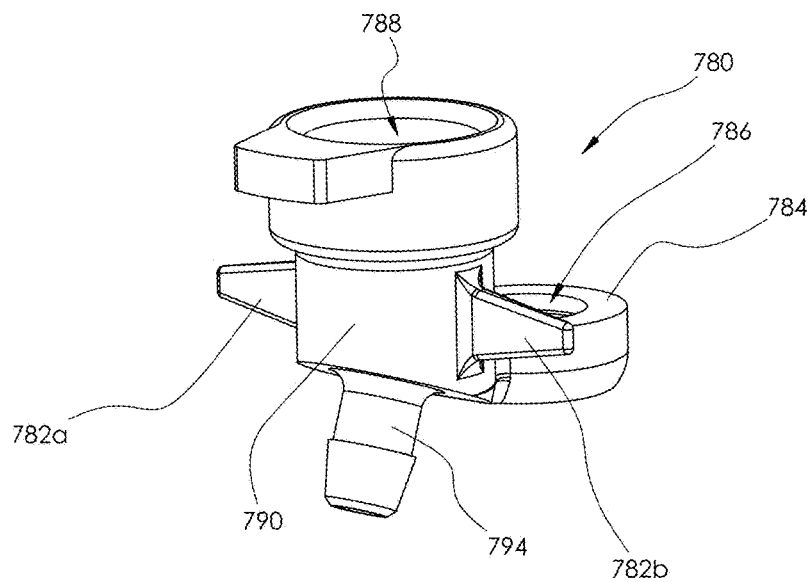
FIG. 28A is a rear isometric view of a rocker arm for the power train assembly of FIG. 26A.
Figures 28B, 28C:
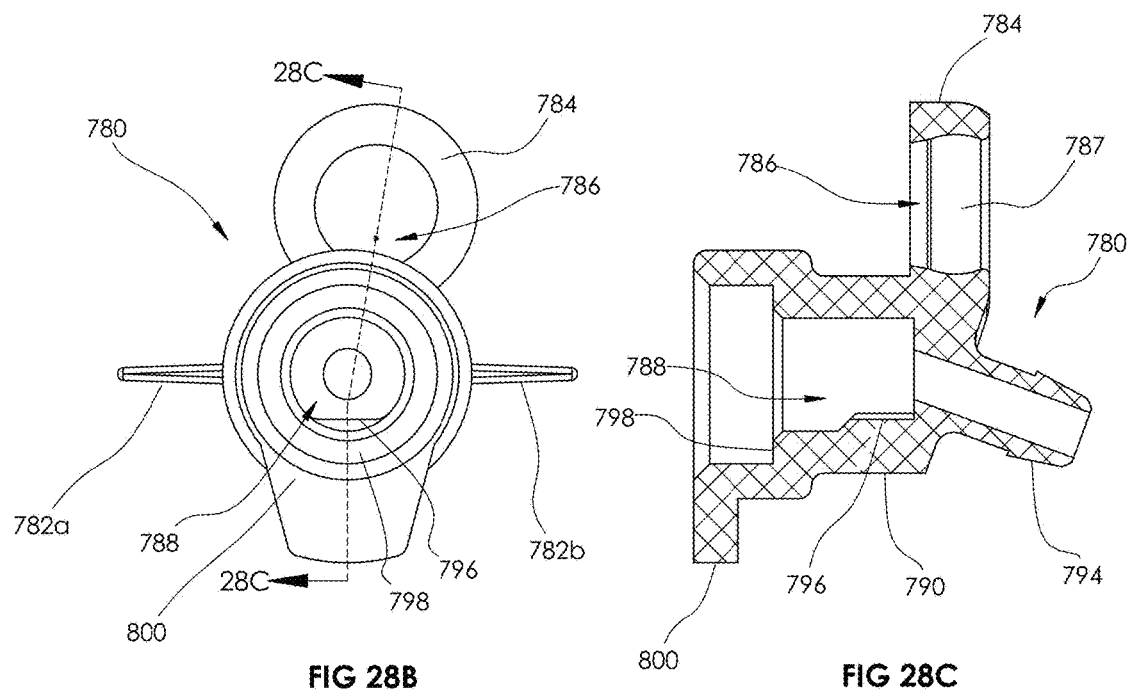
FIG. 28B is a top plan view of the rocker arm of FIG. 9A.
FIG. 28C is a cross-section view of the rocker arm of FIG. 28B taken along line 28C-28C in FIG. 20B.
Figure 29A:
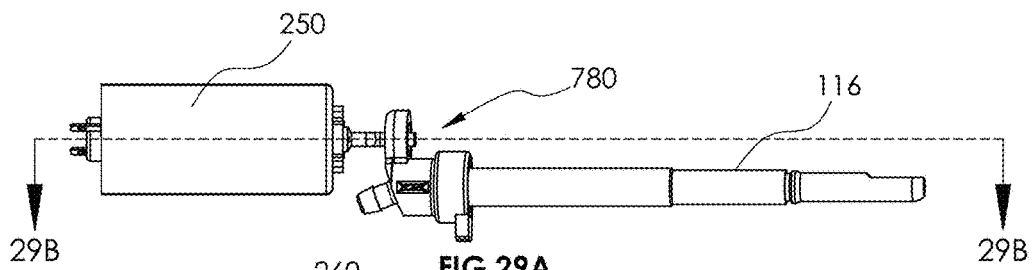
FIG. 29A is a side view of the power train assembly of FIG. 26A illustrating a misaligned output shaft axis in the front plane.
Figure 29B:
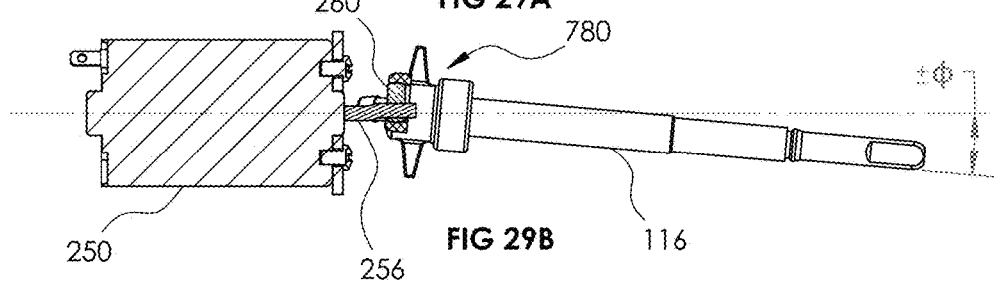
FIG. 29B is a cross-section view of the power train assembly of FIG. 26A illustrating a misaligned output shaft axis in the front plane taken along line 29B-29B in FIG. 10A.
Figure 29C:
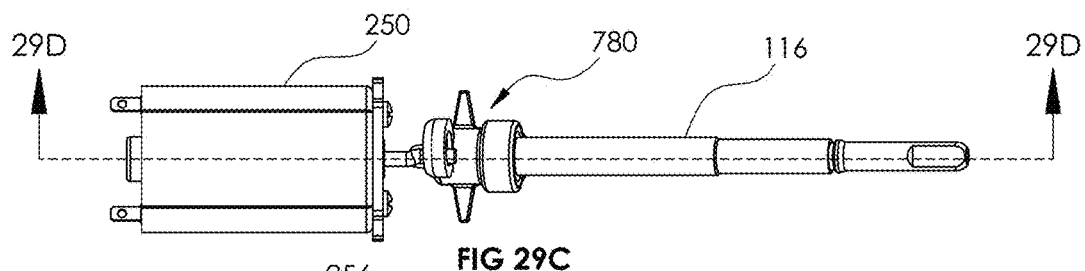
FIG. 29C is a front view of the power train assembly of FIG. 26A illustrating a misaligned output shaft axis in the side plane.
Figure 29D:
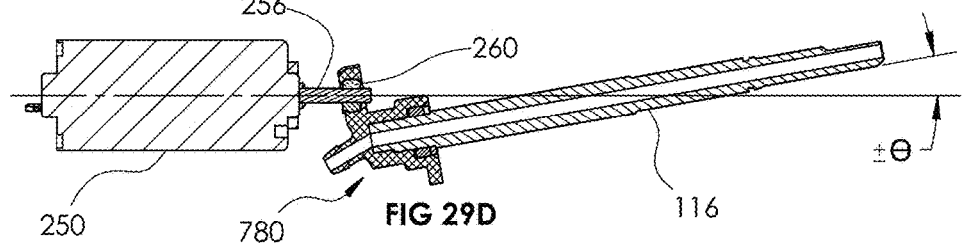
FIG. 29D is a cross-section view of the power train assembly of FIG. 26A illustrating a misaligned output shaft axis in the side plane taken along line 29D-29D in FIG. 29C.
Figure 29E:
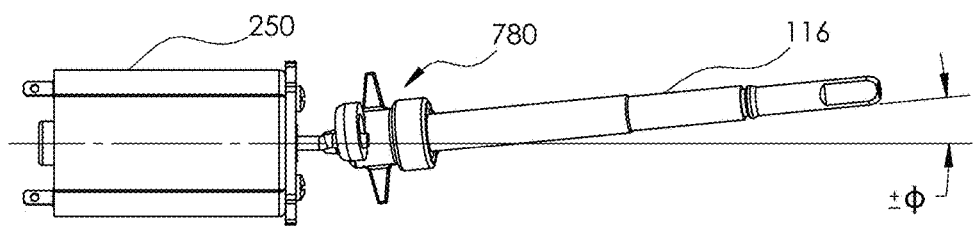
FIG. 29E is a front view of the power train assembly of FIG. 26A illustrating a misaligned output shaft axis in both the front and the side plane.
Figure 29F:
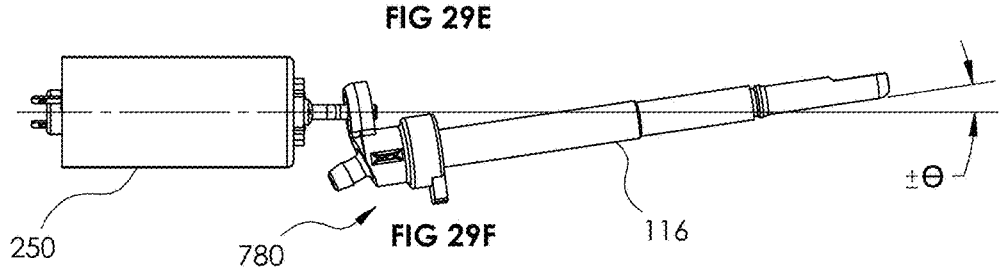
FIG. 29F is a side view of the power train assembly of FIG. 26A illustrating a misaligned output shaft axis in both the front and the side plane.

With reference to FIGS. 28A-28C, the rocker arm 780 will be discussed in more detail. The rocker arm 780 is substantially similar to the rocker arm 262 includes sufficiently flexible spindles or wings that deform, eliminating the separate deformable members (O-rings 264a, 264b). The rocker arm 780 includes a main body 790 including two wings 782a, 782b or arms extending laterally outward from a right side and a left side, respectively, of the main body 790. The two wings 782a, 782b are axially aligned with each other and as shown in FIGS. 28A and 28B taper in two directions, in their width and their thickness as they extend from the main body 790 outwards. In this manner, the terminal end of each of the wings 782a, 782b is narrower both in width and thickness as compared to the connected end of the wings 782a, 782b. This dual taper helps to distribute stresses evenly across the wings 782a, 782b, reducing stress concentrations in the wings 782a, 782b. It should be noted that in other embodiments, the taper may be along a single axis only, e.g., only the width (Y axis) or the thickness (Z axis), or as shown in FIGS. 28A and 28B along two lengths.

The rocker arm 780 also includes a fluid connector 794 extending downward from the main body 790. The fluid connector 794 is configured to connect to a fluid tube and may include a male or female connector, and in one embodiment includes a barb as shown in FIG. 28A. Depending on the configuration of the housing and size of the irrigating toothbrush 700, the fluid connector 794 may be arranged at various angles relative to the main body 790. For example, as shown in FIG. 28A, the fluid connector 794 may extend downward at an angle relative to the main body 790, rather than being perpendicularly oriented relative to the wings 782a, 782b. However, in other embodiments, the fluid connector 794 can be otherwise arranged.

With continued reference to FIGS. 28A-28B, a cylindrical outer wall 800 extends upwards from the top end of the main body 790. The outer wall 800 defines a shaft cavity 788 formed on the top end of the main body 790. The shaft cavity 788 is in fluid communication with the fluid connector 794 via a fluid passage defined through the main body 790. The diameter of the shaft cavity 788 may be varied to assist in retaining the output shaft 116 and other components. For example, the rocker arm 780 may include a locking feature 796 extending into the shaft cavity 788 from an interior surface and optionally an annular shelf 798 extending into the shaft cavity 788 from an interior surface arranged closer to the top end of the outer wall 800 from the locking feature 796. The shaft cavity 788 includes interior surfaces that contact the seal 280. The seal retainer 266 helps to secure the seal 280 within the shaft cavity 788 and provides support on the outside portion of the seal 280. In other configurations the seal retainer 266 can be integrated into the output shaft 116 in a one-piece design. In some embodiments, the rocker arm 780 can be overmolded onto the output shaft 116 to form a watertight seal without additional seal elements. Other features and configurations are also envisioned.

The rocker arm 780 also includes a cam follower 784 that extends from a front surface of the main body 790. The cam follower 784 is a hollow bracket structure that defines an eccentric cavity 786. With reference to FIG. 28C, the eccentric cavity 786 may have a socket 787 to receive the outer surface 261 of the eccentric 260. In embodiments where the outer surface of the eccentric 260 is spherically shaped, the socket 787 may be correspondingly spherically shaped. The socket 787 of the cam follower 784 allows the axis of the eccentric 260 to rotate such that the axis of the motor drive shaft 256 and the axis of the output shaft 116 can have an angular misalignment in one of two planes or both planes simultaneously as shown in FIGS. 29A-29F. Due to the angular misalignment allowed between the axis of the motor drive shaft 256 and the axis of the output shaft 116, when the handle 102 experiences an impact event that causes the chassis 702, 704 to flex, the motor 250 can move with respect to the output shaft 116, allowing the power train assembly 730 to be less susceptible to damage. In addition, less precise motor mounting tolerances can be used because parallel mounting of the motor drive shaft 256 and the output shaft 116 is not required. Further, the position of the motor 250 can be angled in the handle 102 to optimize space for other components, while maintaining the desired orientation of the output shaft 116. The rocker arm 780 of the irrigating toothbrush 700 connects to the output shaft 116 and eccentric 260 in the same manner as the rocker arm 262. See, e.g., FIGS. 30A-30E.

Figure 31A:
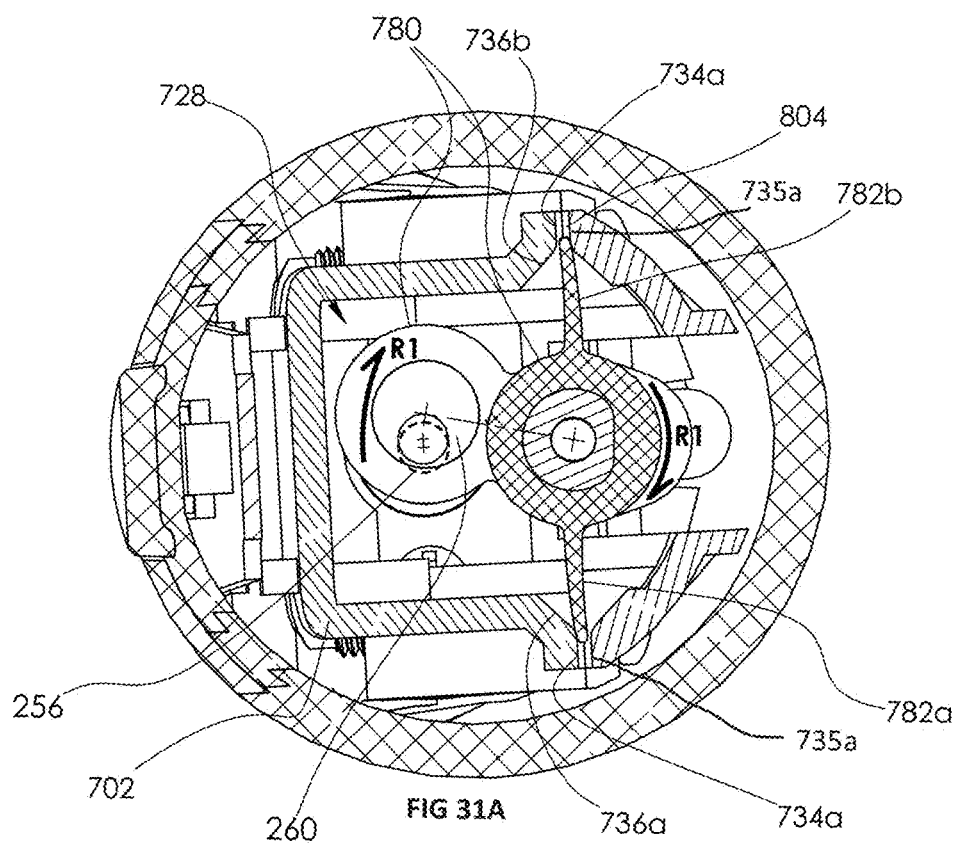
FIG. 31A is a cross-section view of the irrigating toothbrush of FIG. 20A illustrating the power train at a first position.

With reference to FIGS. 21 and 22B, to assemble the rocker arm 780 within the chassis 702, 704, the rocker arm 780 is positioned within the power train cavity 728 and the wings 782a, 782b are aligned with the engagement surfaces 734a, 734b of the front chassis 702. The rear chassis 704 is then connected to the front chassis 704 with the engagement surfaces 735a, 735b aligning with the engagement surfaces 734a, 734b. With reference to FIG. 31A, the alignment of the engagement surfaces 734a, 734b, 735a, 735b defines a slot 804 between the front chassis 702 and the rear chassis 704. The terminal end of the wings 782a, 782b are positioned within this slot 804. In some embodiments, the slot 804 may have a width that substantially matches the thickness of the wings 782a, 782b to prevent any movement of the wings 782a, 782b relative to the chassis 702, 704. In other embodiments, such as the one shown in FIGS. 31A and 31B, the slot 804 is slight larger than the width of the wings 782a, 782b to allow easier assembly, prevent breaking of the wings, while still restraining large movements of the wings 782a,278b. In this configuration, the wings 782a, 782b of the rocker arm 780 are pinched or restrained to the chassis 702, 704 on opposite sides of the output shaft 112. However, the width of the slot 804 may be varied as desired.

Figure 31B:
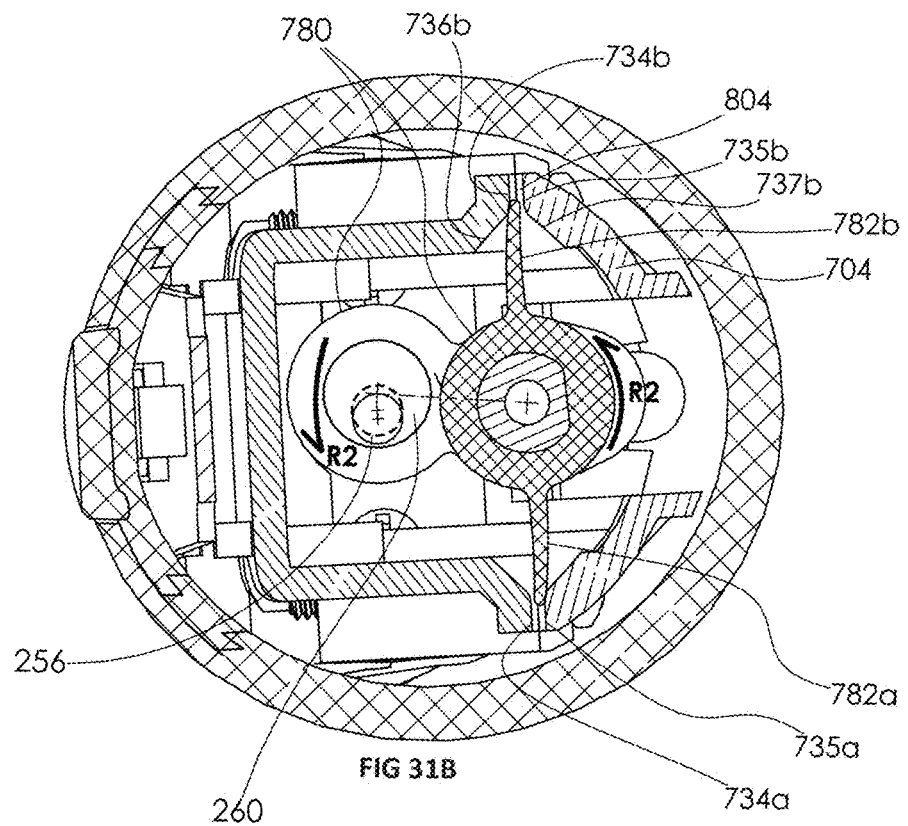
FIG. 31B is a cross-section view of the irrigating toothbrush of FIG. 20A illustrating the power train at a second position.

Operation of the power drive train 730 of the irrigating toothbrush 700 will now be discussed in more detail. FIG. 31A illustrates the output shaft 116 and the rocker arm 780 in a first position and FIG. 31B illustrates the output shaft 116 and the rocker 780 in a second position. With reference to FIG. 31A, as the motor 250 rotates the drive shaft 256, the eccentric 260 rotates within the rocker arm 780, which causes the cam follower 784 of the rocker arm 780 to rotate in direction R1. This causes the output shaft 116 and wings 782a, 782b to pivot along the arc of rotation R1. At the end of the rotation arc R1, the terminal end of the first wing 782a engages the first engagement surface 734a of the front chassis 702 and is prevented from moving further in the rotation direction R1. This causes the wing 782a to deflect or deform as the rocker arm 780 continues to rotate. Simultaneously, the second wing 782b engages the engagement surface 735b of the rear chassis 704 and deforms in an opposite direction. The flexibility of the wings 782a, 782b allows them to deform without shearing or breaking. This deformation absorbs momentum from the motor.

With reference to FIG. 31B, as the motor continues to rotate the drive shaft 256, the movement of the eccentric 260 is constrained by the rocker arm 780 and the rocker arm 780 pivots in a second rotation direction R2. This change in direction, causes the output shaft 112 to rotate along the second rotation arc in direction R2. At the beginning of this directional change, each of the wings 782*a*, 782*b* elastically return to their original shape, provide momentum back to the output shaft 116 via the rocker arm 780, reducing drag and enhancing efficiency of power train assembly 730. Then, as the rocker arm 780 continues to rotate towards the end of the second arc rotation R2, the terminal ends of the wings 782*a*, 782*b* engage the opposite engagement surfaces, e.g., wing 782*a* engages the engagement surface 735*a* of the rear chassis 704 and wing 782*b* engages the engagement surface 734*b* of the front chassis 702. During this engagement, the wings 782*a*, 782*b* are prevented from further rotation and begin to deform as they absorb energy. When the rocker arm 780 pivots to rotate in the first direction R1 again, the wings 782*a*, 782*b* will apply the absorbed energy to the rocker arm 780 as described above. Due to the orientation of the wings and the position on opposite sides of the output shaft, the wings may provide forces at substantially the same time to the output shaft.

Depending on the width of the slot 804, as well as the thickness of the wings 782*a*, 782*b*, the wings 782*a*, 782*b* may be configured to provide or absorb energy to the rocker arm 780 at only the ends of the rotation arcs. However, in other embodiments, the wings may be configured to apply energy along the entirety of a particular rotation direction.

CONCLUSION

Although the above description is discussed with respect to a dual-function device, in some embodiments, the features of the power train and other components of the handle 102 may be incorporated as a standalone brushing device. In other words, although an irrigation function is disclosed, the toothbrush may be used without the irrigating. In these embodiments, the components including a fluid path may be omitted or modified, e.g., the output shaft may be solid rather than hollow.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A brushing device comprising:
   a motor including an eccentric drive shaft;
   an output shaft operably connected to the motor; and
   a power train assembly coupled between the eccentric drive shaft and the output shaft,
   wherein:
      the power train assembly converts rotation of the eccentric drive shaft into an oscillating movement of the output shaft;
      the power train assembly comprises a rocker arm coupled to the eccentric drive shaft and the output shaft; and
      the rocker arm comprises a cam follower and an eccentric received in the cam follower, the eccentric drive shaft received in the eccentric.

2. The brushing device of claim 1, further comprising:
   a chassis assembly, wherein the motor and the power train assembly are at least partially received within the chassis assembly; and
   a housing, wherein the chassis assembly is received within the housing.

3. The brushing device of claim 2, wherein the power train assembly comprises at least one conservation feature that engages one or more surfaces of the chassis assembly to absorb momentum and apply the momentum to the output shaft.

4. The brushing device of claim 1, wherein movement of the rocker arm is constrained to output the oscillating movement in response to the rotation of the eccentric drive shaft.

5. The brushing device of claim 4, further comprising a first wing extending from a first side of the rocker arm and a second wing extending from a second side of the rocker arm to absorb momentum and apply the momentum to the output shaft.

6. The brushing device of claim 5, further comprising a chassis assembly defining a first slot and a second slot, wherein an end of the first wing is received within the first slot and an end of the second wing is received within the second slot.

7. The brushing device of claim 1, wherein the rocker arm further comprises a main body to which the output shaft is coupled, wherein the cam follower comprises a hollow bracket structure that extends from a front surface of the main body.

8. The brushing device of claim 7, wherein the rocker arm further comprises a fluid connector extending downward from the main body.

9. The brushing device of claim 1, wherein movement of the eccentric drive shaft in a single rotational direction causes the eccentric to rotate in an oscillating rotary motion within the cam follower and causes the rocker arm to move correspondingly.

10. The brushing device of claim 1, wherein the eccentric comprises an outer spherical surface received in a spherical socket of the cam follower.

11. The brushing device of claim 1, further comprising one or more sleeve bearings received around an outer surface of the output shaft, wherein the one or more sleeve bearings support and constrain the output shaft.

12. The brushing device of claim 11, further comprising a chassis defining a mounting feature, wherein the chassis at least partially surrounds the output shaft and the one or more bearings are received in the mounting feature.

13. The brushing device of claim 12, wherein the one or more bearings each comprise an outer spherical surface.

14. The brushing device of claim 1, further comprising a brush head removably connected to the output shaft, wherein the oscillating movement of the output shaft causes the brush head to oscillate correspondingly.

15. The brushing device of claim 13, further comprising a fluid passage configured to transport fluid from a fluid source to a fluid conduit in the brush head, wherein a portion of the fluid passage is formed within the power train assembly.

16. The brushing device of claim 15, further comprising:
a handle enclosing the motor and the power train assembly; and
a fluid connector removably coupled to the handle and fluidly connected to the fluid passage formed within the power train assembly.

17. The brushing device of claim 16, wherein the fluid connector is rotatable relative to the handle when secured thereto.

18. The brushing device of claim 1, wherein the eccentric drive shaft is an integrally formed component.

19. The brushing device of claim 1, further comprising:
a chassis assembly; and
a fluid connector operably coupled to the chassis assembly and fluidly coupled to the output shaft via the power train assembly, wherein the fluid connector rotates 360 degrees relative to the chassis assembly.

20. The brushing device of claim 19, wherein the rocker arm includes a first arm extending from a first side and a second arm extending from a second side, wherein during operation the first arm and the second arm are configured to engage directly or indirectly one or more surfaces of the chassis assembly to absorb and reapply momentum to the output shaft.

* * * * *